(12) United States Patent
Ramamurthy et al.

(10) Patent No.: US 10,907,956 B2
(45) Date of Patent: *Feb. 2, 2021

(54) INSTRUMENT SYSTEMS AND METHODS UTILIZING OPTICAL FIBER SENSOR

(75) Inventors: Bhaskar S. Ramamurthy, Los Altos, CA (US); Neal A. Tanner, Mountain View, CA (US); Robert G. Younge, Portola Valley, CA (US); Randall L. Schlesinger, San Mateo, CA (US)

(73) Assignee: KONINKLIJKE PHILIPS ELECTRONICS NV, Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,921

(22) Filed: Sep. 4, 2012

(65) Prior Publication Data
US 2013/0090528 A1 Apr. 11, 2013

Related U.S. Application Data

(62) Division of application No. 12/192,033, filed on Aug. 14, 2008, now Pat. No. 9,186,046.
(Continued)

(51) Int. Cl.
*A61B 5/00* (2006.01)
*G01B 11/16* (2006.01)
(Continued)

(52) U.S. Cl.
CPC .......... *G01B 11/16* (2013.01); *A61B 1/00004* (2013.01); *A61B 1/00013* (2013.01);
(Continued)

(58) Field of Classification Search
CPC ....... A61B 5/06; A61B 5/0059; A61B 5/7285; A61B 1/00165; A61B 8/00;
(Continued)

(56) References Cited

U.S. PATENT DOCUMENTS 3,807,390 A 4/1974 Ostrowski et al.
4,387,722 A 6/1983 Kearns
(Continued)

FOREIGN PATENT DOCUMENTS

EP 0665696 A2 8/1995
EP 1384437 1/2004
(Continued)

OTHER PUBLICATIONS

Eric Udd, "Good Sense", Spie's OE Magazine, Aug. 2002, pp. 27-30.
(Continued)

*Primary Examiner* — May A Abouelela
(74) *Attorney, Agent, or Firm* — Pillsbury Winthrop Shaw Pittman, LLP

(57) ABSTRACT

A method for mapping an internal structure of a patient with an elongate body is provided. The method includes detecting, at a plurality of instances, contact between a distal portion of an elongate body and an internal structure of the patient; determining a plurality of geometric configurations of the distal portion, the plurality of geometric configurations corresponding to the plurality of instances of contact between the distal portion and the internal structure; determining a plurality of positions of the distal portion, the plurality of positions corresponding to the plurality of geometric configurations; and generating a map of the internal structure based on the plurality of positions of the distal portion.

4 Claims, 64 Drawing Sheets

Related U.S. Application Data

(60) Provisional application No. 60/964,773, filed on Aug. 14, 2007.

(51) Int. Cl.
| | | |
|---|---|---|
| *A61B 6/12* | (2006.01) | |
| *A61B 5/06* | (2006.01) | |
| *A61B 90/96* | (2016.01) | |
| *A61B 34/00* | (2016.01) | |
| *A61B 34/30* | (2016.01) | |
| *A61B 34/37* | (2016.01) | |
| *A61B 90/98* | (2016.01) | |
| *A61B 90/00* | (2016.01) | |
| *A61B 1/00* | (2006.01) | |
| *G01L 1/24* | (2006.01) | |
| *A61B 8/08* | (2006.01) | |
| *A61B 18/08* | (2006.01) | |
| *A61B 8/00* | (2006.01) | |
| *A61B 17/00* | (2006.01) | |
| *A61B 34/20* | (2016.01) | |
| *A61M 25/01* | (2006.01) | |

(52) U.S. Cl.
CPC ........ *A61B 1/0017* (2013.01); *A61B 1/00045* (2013.01); *A61B 1/00057* (2013.01); *A61B 1/00165* (2013.01); *A61B 5/0059* (2013.01); *A61B 5/0064* (2013.01); *A61B 5/06* (2013.01); *A61B 5/065* (2013.01); *A61B 5/066* (2013.01); *A61B 5/4887* (2013.01); *A61B 6/12* (2013.01); *A61B 8/00* (2013.01); *A61B 8/48* (2013.01); *A61B 18/082* (2013.01); *A61B 34/30* (2016.02); *A61B 34/37* (2016.02); *A61B 34/71* (2016.02); *A61B 34/77* (2016.02); *A61B 90/39* (2016.02); *A61B 90/96* (2016.02); *A61B 90/98* (2016.02); *G01B 11/165* (2013.01); *G01L 1/242* (2013.01); *A61B 5/7285* (2013.01); *A61B 34/20* (2016.02); *A61B 2017/00725* (2013.01); *A61B 2034/2061* (2016.02); *A61B 2034/301* (2016.02); *A61B 2034/715* (2016.02); *A61B 2034/741* (2016.02); *A61B 2090/374* (2016.02); *A61B 2090/376* (2016.02); *A61B 2090/378* (2016.02); *A61M 2025/0166* (2013.01)

(58) Field of Classification Search
CPC ........ A61B 19/2203; A61B 2019/2211; A61B 34/30; A61B 8/12; A61B 1/07; A61B 17/00234; A61B 34/71; A61B 1/04; A61B 2034/2061; A61B 2034/301; A61B 5/4836; A61B 17/3478; A61B 18/1492; A61B 18/22; A61B 1/00149; A61B 1/0016; A61B 1/2736; A61B 1/313; A61B 1/3132; A61B 5/0077; G01B 11/16; A61N 5/0601; A61N 2005/063; A61N 2005/067
USPC .............. 600/104, 300, 587; 385/12, 13
See application file for complete search history.

(56) References Cited

U.S. PATENT DOCUMENTS

| | | |
|---|---|---|
| 4,443,698 A | 4/1984 | Schiffner |
| 4,761,073 A | 8/1988 | Meltz et al. |
| 4,960,410 A | 10/1990 | Pinchuk |
| 4,996,419 A | 2/1991 | Morey |
| 5,007,705 A | 4/1991 | Morey et al. |
| 5,066,133 A | 11/1991 | Brienza |
| 5,088,501 A | 2/1992 | Niewisch |
| 5,118,931 A | 6/1992 | Udd et al. |
| 5,144,960 A | 9/1992 | Domash |
| 5,146,206 A | 9/1992 | Callaway |
| 5,267,339 A | 11/1993 | Yamauchi et al. |
| 5,380,995 A | 1/1995 | Udd et al. |
| 5,397,891 A | 3/1995 | Udd et al. |
| 5,401,956 A | 3/1995 | Dunphy et al. |
| 5,492,131 A | 2/1996 | Galel |
| 5,563,967 A | 10/1996 | Haake |
| 5,591,965 A | 1/1997 | Udd |
| 5,627,927 A | 5/1997 | Udd |
| 5,630,783 A | 5/1997 | Steinberg |
| 5,798,521 A | 8/1998 | Froggatt |
| 5,828,059 A | 10/1998 | Udd |
| 5,917,978 A | 6/1999 | Rutterman |
| 6,035,082 A | 3/2000 | Murphy et al. |
| 6,069,420 A | 5/2000 | Mizzi et al. |
| 6,144,026 A | 11/2000 | Udd et al. |
| 6,215,943 B1 | 4/2001 | Crotts et al. |
| 6,256,090 B1 | 7/2001 | Chen et al. |
| 6,275,511 B1 | 8/2001 | Pan et al. |
| 6,275,628 B1 | 8/2001 | Jones et al. |
| 6,278,811 B1 | 8/2001 | Hay et al. |
| 6,301,420 B1 | 10/2001 | Greenaway |
| 6,366,722 B1 | 4/2002 | Murphy et al. |
| 6,389,187 B1 | 5/2002 | Greenaway et al. |
| 6,404,956 B1 | 6/2002 | Brennan, III et al. |
| 6,426,796 B1 | 7/2002 | Pulliam et al. |
| 6,471,710 B1 | 10/2002 | Bucholtz |
| 6,545,760 B1 | 4/2003 | Froggatt et al. |
| 6,554,771 B1 | 4/2003 | Buil et al. |
| 6,571,639 B1 | 6/2003 | May et al. |
| 6,611,700 B1 * | 8/2003 | Vilsmeier et al. ............ 600/407 |
| 6,671,055 B1 | 12/2003 | Wavering et al. |
| 6,716,178 B1 * | 4/2004 | Kilpatrick et al. ........... 600/504 |
| 6,796,963 B2 | 9/2004 | Carpenter et al. |
| 6,816,266 B2 | 11/2004 | Varshneya et al. |
| 6,826,343 B2 | 11/2004 | Davis et al. |
| 6,868,195 B2 | 3/2005 | Fujita |
| 6,876,786 B2 | 4/2005 | Chliaguine |
| 6,888,623 B2 | 5/2005 | Clements |
| 6,892,090 B2 * | 5/2005 | Verard et al. ................ 600/424 |
| 6,898,337 B2 | 5/2005 | Averett et al. |
| 6,923,048 B2 | 8/2005 | Willsch et al. |
| 6,939,313 B2 * | 9/2005 | Saadat ................. A61B 5/015 600/587 |
| 6,965,708 B2 | 11/2005 | Luo et al. |
| 6,987,897 B2 | 1/2006 | Elster et al. |
| 7,010,182 B2 | 3/2006 | Pennington |
| 7,038,190 B2 | 5/2006 | Udd et al. |
| 7,042,573 B2 | 5/2006 | Froggatt |
| 7,046,866 B2 | 5/2006 | Sahlgren et al. |
| 7,154,081 B1 | 12/2006 | Friedersdorf et al. |
| 7,196,317 B1 | 3/2007 | Meissner, II et al. |
| 7,258,674 B2 | 8/2007 | Hillstead et al. |
| 7,330,245 B2 | 2/2008 | Froggatt |
| 7,538,883 B2 | 5/2009 | Froggatt et al. |
| 7,561,276 B2 | 7/2009 | Boyd |
| 7,742,805 B2 | 6/2010 | Furnish et al. |
| 7,772,541 B2 | 8/2010 | Childers et al. |
| 7,781,724 B2 | 8/2010 | Childers |
| 7,789,875 B2 | 9/2010 | Brock et al. |
| 7,824,328 B2 | 11/2010 | Gattani et al. |
| 8,050,523 B2 * | 11/2011 | Younge et al. ................ 385/13 |
| 8,190,238 B2 | 5/2012 | Moll et al. |
| 9,186,047 B2 | 11/2015 | Ramamurthy et al. |
| 2001/0021843 A1 * | 9/2001 | Bosselmann et al. .......... 606/2 |
| 2003/0095263 A1 | 5/2003 | Varshneya et al. |
| 2003/0195502 A1 | 10/2003 | Garabedian et al. |
| 2003/0236474 A1 | 12/2003 | Singh |
| 2004/0034300 A1 * | 2/2004 | Verard et al. ................ 600/424 |
| 2004/0039312 A1 | 2/2004 | Hillstead et al. |
| 2004/0165810 A1 * | 8/2004 | Fujita ........................... 385/12 |
| 2005/0036140 A1 | 2/2005 | Elster et al. |
| 2005/0075704 A1 | 4/2005 | Tu et al. |
| 2005/0137478 A1 | 6/2005 | Younge et al. |
| 2005/0197530 A1 | 9/2005 | Wallace et al. |
| 2005/0201664 A1 | 9/2005 | Udd et al. |

(56) References Cited

U.S. PATENT DOCUMENTS

| | | | |
|---|---|---|---|
| 2005/0222554 | A1 | 10/2005 | Wallace et al. |
| 2006/0013523 | A1* | 1/2006 | Childlers et al. ............... 385/12 |
| 2006/0036164 | A1 | 2/2006 | Wilson et al. |
| 2006/0036213 | A1 | 2/2006 | Viswanathan |
| 2006/0057560 | A1 | 3/2006 | Hlavka et al. |
| 2006/0084945 | A1 | 4/2006 | Moll et al. |
| 2006/0095022 | A1 | 5/2006 | Moll et al. |
| 2006/0100610 | A1 | 5/2006 | Wallace et al. |
| 2006/0111692 | A1 | 5/2006 | Hlavka et al. |
| 2006/0200026 | A1 | 9/2006 | Wallace et al. |
| 2006/0200049 | A1 | 9/2006 | Leo et al. |
| 2006/0253107 | A1* | 11/2006 | Hashimshony ...... A61B 5/0084 606/1 |
| 2006/0253108 | A1 | 11/2006 | Yu et al. |
| 2006/0276775 | A1 | 12/2006 | Rosenberg et al. |
| 2007/0043338 | A1 | 2/2007 | Moll et al. |
| 2007/0060847 | A1* | 3/2007 | Leo ...................... A61B 5/0084 600/587 |
| 2007/0135803 | A1 | 6/2007 | Belson |
| 2007/0156019 | A1* | 7/2007 | Larkin et al. ................. 600/104 |
| 2007/0156123 | A1 | 7/2007 | Moll et al. |
| 2007/0161857 | A1 | 7/2007 | Durant et al. |
| 2007/0179485 | A1 | 8/2007 | Yeik et al. |
| 2007/0185397 | A1 | 8/2007 | Govari et al. |
| 2007/0197896 | A1 | 8/2007 | Moll et al. |
| 2007/0197939 | A1 | 8/2007 | Wallace et al. |
| 2007/0233044 | A1 | 10/2007 | Wallace et al. |
| 2007/0265503 | A1 | 11/2007 | Schlesinger et al. |
| 2008/0009750 | A1 | 1/2008 | Nicolas |
| 2008/0218770 | A1 | 9/2008 | Moll |
| 2008/0243064 | A1 | 10/2008 | Stahler et al. |
| 2008/0249536 | A1 | 10/2008 | Stahler et al. |
| 2008/0262480 | A1 | 10/2008 | Stahler et al. |
| 2008/0262513 | A1 | 10/2008 | Stahler et al. |
| 2008/0285909 | A1 | 11/2008 | Younge et al. |
| 2009/0123111 | A1 | 5/2009 | Udd |
| 2009/0137952 | A1 | 5/2009 | Ramamurthy et al. |
| 2009/0138025 | A1 | 5/2009 | Stahler et al. |

FOREIGN PATENT DOCUMENTS

| | | |
|---|---|---|
| EP | 1413258 | 4/2004 |
| WO | WO 92/02276 | 2/1992 |
| WO | 01/13060 | 2/2001 |
| WO | WO 01/33165 | 5/2001 |
| WO | WO 0133165 A1 * | 5/2001 |
| WO | WO 02/47751 | 6/2002 |
| WO | WO 03/065095 | 8/2003 |
| WO | WO 2004/001469 | 12/2003 |
| WO | WO 2005/087128 | 9/2005 |
| WO | WO 2005087128 A1 * | 9/2005 |
| WO | 2005/113068 A1 | 12/2005 |
| WO | WO 2006/092707 | 9/2006 |
| WO | WO 2006/099056 | 9/2006 |
| WO | WO 2008/094949 | 8/2008 |
| WO | WO 2008/131303 | 10/2008 |

OTHER PUBLICATIONS

Roger Duncan, "Sensing Shape: Fiber-Bragg-grating sensor arrays monitor shape at a high resolution", Spie's OE Magazine, Sep. 2005, pp. 18-21.
G.M.H. Flockhart et al., "Two-axis bend measurement with Bragg gratings in multicore optical fiber", Optics Letters, Mar. 15, 2003, pp. 387-389, vol. 28 No. 6, Optical Society of America.
File history of U.S. Pat. No. 6,256,090, (U.S. Appl. No. 09/127,083), issued on Jul. 3, 2001.
File history of U.S. Pat. No. 6,470,205, (U.S. Appl. No. 09/804,804), issued on Oct. 22, 2002.
File History of U.S. Pat. No. 5,798,521, (U.S. Appl. No. 08/086732) issued on Aug. 25, 1998.
Alan D. Kersey et al., "Fiber Grating Sensors", Journal of Lightwave Technology, Aug. 1997, pp. 1442-1463 vol. 15 No. 8.
Mark Froggatt et al., "Distributed measurement of static strain in an optical fiber with multiple Bragg gratings at nominally equal wavelengths", Applied Optics, Apr. 1, 1998, pp. 1741-1746, vol. 37 No. 10.
Raymond M. Measures, "Fiber Optic Strain Sensing", Fiber Optic Smart Structures, 1995, pp. 171-247, John Wiley & Sons Inc.
C.M. Lawrence et al., "A Fiber Optic Sensor for Transverse Strain Measurement", Experimental Mechanics, Sep. 1999, pp. 202-209, vol. 39 No. 3.
File history of U.S. Appl. No. 11/450,072, filed Jun. 9 2006, published as 2008-0009750, on Jan. 10, 2008.
Meng-Chou Wu et al., "Fabrication of self-apodized short-length fiber Bragg gratings", Applied Optics, Sep. 1, 2003, pp. 5017-5023, vol. 42, No. 25.
Kenneth O. Hill et al., "Fiber Bragg Grating Technology Fundamentals and Overview", Journal of Lightwave Technology, Aug. 1997, pp. 1263-1276, vol. 15, No. 8.
Yan Zhang et al., "Fiber-Bragg-grating-based seismic geophone for oil/gas prospecting", Optical Engineering, Aug. 2006, pp. 84404-1-84404-4, vol. 45 No. 8.
Matthew T. Raum, "Error Analysis of Three Dimensional Shape Sensing Algorithm", Virginia Tech, Apr. 26, 2005.
Mark E. Froggatt et al., "Distributed Fiber-Optic Strain and Temperature Sensors Using Photoinduced Bragg Gratings", Feb. 1995, pp. 1741-1746, Blacksburg Virginia.
Claire Davis, "Strain Survey of an F/A-18 Stabilator Spindle Using High Density Bragg Grating Arrays", Feb. 2005, Australia.
Zhang Lun-Wei, "Novel shape detection systems based on FBG sensor net for intelligent endoscope", Journal of Shanghai University (English Edition), Apr. 2006, pp. 154-155, vol. 10 No. 2.
V.V. Wong et al., "Distributed Bragg grating integrated-optical filters: Synthesis and fabrication", American Vacuum Society, Nov./Dec. 1995, pp. 2859-2864, vol. 13 No. 6.
Youngmin Kim et al., "Micromachined Fabry-Perot Cavity Pressure Transducer", IEEE Photonics Technology Letters, Dec. 1995, pp. 1471-1473, vol. 7 No. 12.
John W. Berthold III, "Historical Review of Microbend Fiber-Optic Sensors", Journal of Lightwave Technology, Jul. 1995, pp. 1193-1199, vol. 13 No. 7.
R. Posey Jr. et al., "Strain sensing based on coherent Rayleigh scattering in an optical fibre", Electronics Letters, Sep. 28, 2000, pp. 1688-1689, vol. 36 No. 20.
Kazuo Hotate et al., "Proposal and experimental verification of Bragg wavelength distribution measurement within a long-length FBG by synthesis of optical coherence function" Optics Express, May 26, 2008, pp. 7881-7887, vol. 16 No. 11.
M.M. Ohn et al., "Arbitrary strain profile measurement within fibre gratings using interferometric Fourier transform technique", Electronics Letters, Jul. 3, 1997, pp. 1242-1243, vol. 33 No. 14.
Zhang Lunwei et al., "FBG Sensor Devices for Spatial Shape Detection of Intelligent Colonscope", Apr. 2004, pp. 835-840, New Orleans Louisiana.
Craig M. Lopatin et al., "Distributed Measurement of Strain in Smart Materials Using Rayleigh Scattering", 32 International SAMPE Technical Conference, Nov. 2000, pp. 231-241.
X.G. Tian et al., "Torsion Measurement Using Fiber Bragg Grating Sensors", Experimental Mechanics, Sep. 2001, pp. 248-253, vol. 41 No. 3.
Garret Lee et al., "Intraoperative Use of Duel Fiberoptic Catheter for Simultaneous In Vivo Visualization and Laser Vaporization of Peripheral Atherosclerotic Obstructive Disease", Catheterization and Cardiovascular Diagnosis, 1984, pp. 11-16.
Mark Froggatt et al., "High-spatial-resolution distributed strain measurement in optical fiber with Rayleigh scatter", Applied Optics, Apr. 1, 1998, pp. 1735-1740, vol. 37 No. 10.
Gary A. Miller et al., "Shape Sensing Using Distributed Fiber Optic Strain Measurements", Second European Workshop on Optical Fibre Sensors, Proceedings of the SPIE, Jun. 2004, pp. 528-531, vol. 5502.
M. J. Gander et al., "Measurement of bending in two dimensions using multicore optical fibre", European Workshop on Optical Fibre Sensors, Jun. 1998, p. 64-68, Proc. SPIE vol. 3483.

(56) References Cited

OTHER PUBLICATIONS

Ad A. M. Maas, "Shape measurement using phase shifting speckle interferomentry", Laser Interferometry IV: Computer-Aided Interferometry, Jan. 1, 1992, pp. 558-568, Proceedings SPIE vol. 1553.

Roger R. Duncan et al., "Use of high spatial resolution fiber-optic shape sensors to monitor the shape of deployable space structures" Space Technology and Applications Int.Forum—STAIF 2005: Conf. Thermophys in Micrograv;Conf Comm/Civil Next Gen.Space Transp; 22nd Symp Space Nucl.Powr Propuls.;Conf.Human/Robotic Techn. Nat'l Vision Space Expl.; 3rd Symp Space Colon.; 2nd Symp.New Frontiers. AIP Conference Proceedings, Feb. 2005, pp. 880-886, vol. 746.

Joeseph R. Blandino et al., "Three-dimensional shape sensing for inflatable booms", 46th AIAA/ASME/ASCE/AHS/ASC Structures, Structural Dynamics & Materials Conference, Austin, Texas, Conference Dates : Apr. 18-21, 2005, pp. 1-10.

Roger R. Duncan et al., "Characterization of a fiber optic shape and position sensor" Conference Title: Smart Structures and Materials 2006: Smart Sensor Monitoring Systems and Applications; San Diego, CA, Conference Date: Monday Feb. 27, 2006, Published in: Proc. SPIE, vol. 6167, 616704 (2006); doi:10.1117/12.658535, Online Publication Date: Mar. 30, 2006.

A. F. Abouraddy et al., "Towards multimaterial multifunctional fibres that see, hear, sense, and communicate", Nature Materials 6, Publication date: May 2007, pp. 336-347.

Roger R. Duncan et al., "High-accuracy fiber-optic shape sensing" Conference Title: Sensor Systems and Networks: Phenomena, Technology, and Applications for NDE and Health Monitoring 2007, San Diego, California, USA, Conference Date: Monday Mar. 19, 2007, Published in: Proc. SPIE, vol. 6530, 65301S (2007); doi:10.1117/12.720914, Online Publication Date: Apr. 10, 2007.

Eric Udd et al., "Progress on developing a multiaxis fiber optic strain sensor" Third Pacific Northwest Fiber Optic Sensor Workshop, Publication Date: Sep. 2, 1997, pp. 50-56, Proceedings SPIE vol. 3180.

Eric Udd et al., "Multidimensional strain field measurements using fiber optic grating sensors", Smart Structures and Materials 2000: Sensory Phenomena and Measurement Instrumentation for Smart Structures and Materials, Publication Date: Jun. 12, 2000, pp. 254-262, Proceedings SPIE vol. 3986.

Juncheng Xu et al., "Miniature fiber optic pressure and temperature sensors", Fiber Optic Sensor Technology and Applications IV, Publication Date: Nov. 10, 2005, pp. 600403-1-600403-6, Proceedings SPIE vol. 6004.

M. Lequime et al., "Fiber optic pressure and temperature sensor for down-hole applications", , Fiber Optic Sensors: Engineering and Applications, Publication Date: Aug. 1, 1991, pp. 244-249, Proceedings SPIE vol. 1511.

T. Sato et al., "Ground strain measuring system using optical fiber sensors", Smart Structures and Materials 2000: Sensory Phenomena and Measurement Instrumentation for Smart Structures and Materials, Publication Date: Jun. 12, 2000, pp. 180-190, Proceedings SPIE vol. 3986.

Sandra M. Klute et al., "Fiber-optic shape sensing and distributed strain measurements on a morphing chevron", 44th AIAA Aerospace Sciences Meeting and Exhibit, Conference dates: Jan. 9-12, 2006, pp. 1-25, Reno Nevada,.

Roger R. Duncan et al., "Fiber-optic shape and position sensing", Proceedings of the 5th International Conference on Structural Health Monitoring (2005), Structural Health Monitoring, 2005: Advancements and Challenges for Implementation, Copyright 2005.

Mark Froggatt, Intracore and extracore examination of fiber gratings with coherent, Thesis (PhD). The University of Rochester, Jun. 2001, pp. 6540, Source DAI-B 61/12.

Brooks A. Childers et al., "Recent development in the application of optical frequency domain reflectometry to distributed Bragg grating sensing", Fiber Optic Sensor Technology and Applications, pp. 19-31, Feb. 2002, Proc. SPIE vol. 4578.

J. Grant et al., "Investigation of structural properties of carbon-epoxy composites using fiber-bragg gratings", Applications of Photonic Technology 5, Publication Date: Feb. 17, 2003, pp. 191-199, Proceedings SPIE vol. 4833.

Roger R. Duncan et al., "A distributed sensing technique for aerospace applications", 42nd AIAA Aerospace Sciences Meeting and Exhibit, Conference dates: Jan. 5-8, 2004, Reno, Nevada.

S. Huang et al., "Continuous arbitrary strain profile measurements with fiber bragg gratings", Smart Materials and Structures, Publication Date: Apr. 1998, pp. 248-256, vol. 7, No. 2.

Youngmin Kim et al., "Design for manufacture of micromachined Fabry-Perot cavity-based sensors", Sensors and actuators. A, Physical, ISSN 0924-4247, 1995, pp. 141-146 [(article)], vol. 50, n°1-2.

Eric Pinet et al., "True challenges of disposable optic fiber sensors for clinical environment", Third European Workshop on Optical Fibre Sensors, Antonello Cutolo; Brian Culshaw; José Miguel López-Higuera, Editors, 66191Q, Publication Date: Jul. 2, 2007, pp. 66191Q-1-66191Q-4, Proceedings SPIE vol. 6619.

Brian J. Soller et al., "Optical frequency domain reflectometry for single- and multi-mode avionics fiber-optics applications", Avionics Fiber-Optics and Photonics, Publication Date: Sep. 12-14, 2006, pp. 38-39, IEEE Conference.

Jin-Seok Heo et al., "Design of TR-EFPI fiber optic pressure sensor for the medical application", International Journal of Human-friendly Welfare Robotic Systems, Published : 2002, pp. 2-7, vol. 3, No. 2.

Matt Raum et al "Performance Analysis of a Fiber-Optic Shape Sensing Systems" cited as reference of 'Fiber-optic shape sensing and distributed strain measurements on a morphing chevron', Collection of Technical papers—44$^{th}$ AIAA, vol. 10, 2006, pp. 7460-7482.

Kirby et al, "Optimal sensor layout for shape estimation form strain sensors", Smart Structures and Materials, Mar. 1995, pp. 367-376, Proc. SPIE vol. 2444.

Maas, "Shape Measurement using phase shifting speckle interferometry", Laser Interferometry IV, Jan. 1992, pp. 558-568, SPIE vol. 1553.

Davis et al, "Fiber-optic bragg grating array for shape and vibration mode sensing", May 1994, pp. 94-102, Proceedings SPIE vol. 2191.

Gander et al, "Bend Measurement using multicore optical fiber", Proceedings of OFS-12, Oct. 1997, pp. 166-169.

Kreger et al, "Distributed strain and temperature sensing in plastic optical fiber using Rayleigh scattering", Apr. 2009, pp. 73160A-1-73160A-8, Proc. of SPIE 7316.

Kreger et al, "High-resolution extended distance distributed fiber-optic sensing using Rayleigh backscatter", Apr. 2007, pp. 65301R-1-65301R-30, Proc. of SPIE vol. 6530.

Danisch et al, "Spatially continuous six degree of freedom position and orientation sensor", Sensor Review, 1999, pp. 106-112, vol. 19.

Gifford et al, "Swept-wavelength interferometric interrogation of fiber Rayleigh scatter for distributed sensing applications", 2007, pp. 67700F-1-67700E-9, Proc. of SPIE col. 6770.

Miller et al, "Fiber-optic shape sensing for flexible structures", Feb. 1989, pp. 399-404, SPIE 1170.

Morey, "Fiber-optic bragg grating sensors", 1989, pp. 98-107, SPIEL col. 1169.

Trimble, "Successful fiber sensor for medical applications", May 1993, pp. 147-150, Proceedings SPIE vol. 1886.

Grossman et al, "Development of microbend sensors for pressure, load, displacement measurements in civil engineering", May 1994, pp. 112-125, Proceedings SPIE vol. 2191.

Lawrence et al, "Multi-parameter sensing with fiber bragg gratings", 1996, pp. 24-31, Proceedings of SPIE vol. 2872.

Schulz et al, "Health monitoring of adhesive joints using multi-axis fiber grating strain sensor system", Jan. 1999, pp. 41-52, Proceedings of SPIE vol. 3586.

Katsuki et al, "The Experimental Research on the Health Monitoring of the Concrete Structures Using Optical Fiber Sensor", BAM International Symposium (NDT-CE 2003), Non-destructive Testing in Civil Engineering, Sep. 16-19, 2003.

Ye et al., "A Polarization-maintaining Fiber Bragg Grating Interrogation System for Multi-Axis Strain Sensing", Measurement Science and Technology, Aug. 7, 2002, pp. 1446-1449.

(56) References Cited

OTHER PUBLICATIONS

Wippich et al., "Tunable Lasers and Fiber-Bragg-Grating Sensors", The Industrial Physicist, Jun./Jul. 2003, pp. 24-27.
Sorin, W.V. "Survey of Different Techniques", Optical Reflectometry for Component Characterization, Fiber Optic Test and Measurement, Dennis Derickson (editor), 1997, , Chapter 10, Section 10.5, pp. 424-429.
Schulz et al., "Advanced Fiber Grating Strain Sensor Systems for Bridges, Structures, and Highways", Proceedings of SPIE 3325, 212 (1998).
Schreiber et al., "Stress-induced Birefringence in Large-mode-area Micro-structured Optical Fibers", Optics Express, May 16, 2005, pp. 3637-3646, vol. 13 No. 10.
Capouilliet et al., "A Fiber Bragg Grating Measurement System for Monitoring Optical Fiber Strain", IWCS/FOCUS Internat conference Nov. 12-15, 2001, pp. 240-248.
Xue et al., "Simultaneous Measurement of Stress and Temperature with a Fiber Bragg Grating Based on Loop Thin-Wall Section Beam", Mar. 2, 2006, pp. 1-16.
Soller et al., "High Resolution Optical Frequency Domain Reflectometry for Characterization of Components and Assemblies", Optics Express, Jan. 24, 2005, pp. 666-674, vol. 13 No. 2.
Satava, "How the Future of Surgery is Changing: Robotics, Telesurgery, Surgical Simulators and Other Advanced Technologies", May 2006, pp. 2-21.
Janssen et al., "Signal Averaging in the Undergraduate Laboratory", Europe Journal of Physics, 9 (1988), pp. 131-134.
Danisch et al., "Bend Enhanced Fiber Optic Sensors in a Teleoperation Application", Fiber Optic and Laser Sensors XI, 1993, pp. 73-85, SPIE vol. 2070.
MacDonald et al., "Frequency domain optical reflectometer", Applied Optics, vol. 20, No. 10, May 15, 1981, pp. 1840-1844.
Notification of the First Office Action as issued for Chinese Patent Application No. 2007800099556.6, dated Feb. 5, 2010.
Notification of the Second Office Action as issued for Chinese Patent Application No. 2007800099556.6, dated Dec. 14, 2010.
PCT International Search Report for PCT/US2007/064728, Applicant: Hansen Medical, Inc., Forms PCT/ISA/210 and 220, dated Jul. 31, 2007 (7 pages).
PCT Written Opinion of the International Search Authority for PCT/US2007/064728, Applicant: Hansen Medical, Inc., Form PCT/ISA/237, dated Jul. 31, 2007 (9 pages).
Kunzler et al., "Damage Evaluation and Analysis of Composite Pressure Vessels Using Fiber Bragg Gratings to Determine Structural Health", Proceedings of SPIE, vol. 5758, p. 168, 2005 (9 pages).
Udd et al., "Usage of Multi-Axis Fiber Grating Strain Sensors to Support Nondestructive Evaluation of Composite Parts and Adhesive Bond Lines", Structural Health Monitoring Workshop, Stanford University, p. 972, DEStech Publications, 2003 (9 pages).
Grobnic et al., "Localized High Birefringence Induced in SMF-28 Fiber by Femtosecond IR Laser Exposure of the Cladding", Journal of Lightwave Technology, vol. 25, No. 8, Aug. 2007, pp. 1996-2001.
Walker et al., "Shaping the radiation field of tilted fiber Bragg gratings", J. Opt. Soc. Am. B, vol. 22, No. 5, May 2005, pp. 962-975.
Ivanoff et al., "Tunable PDL of Twisted-Tilted Fiber Gratings", IEEE Photonics Technology Letters, vol. 15, No. 6, Jun. 2003, pp. 828-830.
Mihailov et al., "UV-induced polarization-dependent loss (PDL) in tilted fibre Bragg gratings: application of a PDL equaliser", IEE Proc.-Optoelectron., vol. 149, No. 5/6, Oct./Dec. 2002, pp. 211-216.
U.S. Appl. No. 60/898,200, filed Jan. 29, 2007, 16 pages.
Office Action from related application EP 08797926.6, Applicant Hansen Medical, Inc., dated Jan. 17, 2011 (5 pages).
PCT International Search Report and Written Opinion of the International Searching Authority for PCT/US2008/073215 dated Jan. 21, 2009, Applicant Hansen Medical, Inc., Forms PCT/ISA/210, 220, and 237 (15 pages).
U.S. Office Action dated Mar. 29, 2013 for U.S. Appl. No. 13/603,068.

"Fiber Optic Interferometer Fabry-Perot",physics-animations.com/sensors/English/interf.htm, pp. 1-5; Dec. 9, 2010.
Brooks A. Childers et al., "Recent development in the application of optical frequency domain reflectometry to distributed Bragg grating sensing", Luna Innovations and NASA Langley Research Center joint PowerPoint presentation; Fiber Optic Sensor Technology and Applications 2001; SPIE vol. 4578; pp. 19-31; 2002.
Hayano et al., "Structural Health Monitoring System Using FBG Sensor Simultaneous Detection of Acceleration and Strain", Department of System Design Engineering, Keio University, pp. 1-14; Mar. 27, 2006.
Office Action issued in U.S. Appl. No. 13/603,015, dated Dec. 4, 2014.
Office Action issued in U.S. Appl. No. 13/603,048, dated Jan. 2, 2015.
Office Action issued in U.S. Appl. No. 13/602,893, dated Jan. 5, 2015.
Office Action issued in U.S. Appl. No. 13/602,853, dated Jan. 5, 2015.
Davis et al., "A new sensor for monitoring chest wall motion during high-frequency oscillatory ventilation," Medial Engineering & Physics 21 (1999), pp. 619-623.
Augousti et al., "Improved fibre optic respiratory monitoring using a figure-of-eight coil," Physiological Measurement 26 (2005), pp. 585-590.
Allsop et al., "Embedded progressive-three-layered fiber long-period gratings for respiratory monitoring," Journal of Biomedical Optics 8(3), pp. 552-558 (Jul. 2003).
Final Office Action issued in U.S. Appl. No. 13/602,893, dated Jun. 24, 2015.
Non-Final Office Action issued in U.S. Appl. No. 13/603,095, dated Jun. 26, 2015.
Final Office Action issued in U.S. Appl. No. 13/603,048, dated Jul. 10, 2015.
Final Office Action issued in U.S. Appl. No. 13/603,068, dated Jul. 20, 2015.
Office Action issued in U.S. Appl. No. 13/603,068, dated Mar. 6, 2015.
Office Action issued in U.S. Appl. No. 13/602,853, dated Mar. 18, 2015.
Office Action issued in U.S. Appl. No. 13/603,015, dated Apr. 1, 2015.
Office Action issued in U.S. Appl. No. 13/602,990, dated Apr. 23, 2015.
Office Action issued in U.S. Appl. No. 13/603,114, dated Apr. 24, 2015.
Final Office Action dated Nov. 27, 2015 in corresponding U.S. Appl. No. 13/603,095 (9 pages).
Office Action European Patent Application No. EP 13151247.7 dated Jul. 23, 2018.
Office Action European Patent Application No. EP 13151245.1 dated Jul. 23, 2018.
Office Action European Patent Application No. 13151246.9 dated Jul. 23, 2018.
G. Murtaza et al., "Referencing strategies for intensity modulated optical fibre sensors: a review", Optics and Laser Technology, Elsevier Science Publishers BV., Amsterdam, NL, vol. 25, No. 4, Aug. 1, 1993, pp. 235-246.
Communication pursuant to Article 94(3) EPC dated Nov. 11, 2019 issued in corresponding EP Application No. EP 13151396.2.
Communication pursuant to Article 94(3) EPC dated Nov. 11, 2019 issued in corresponding EP Application No. EP 13151401.0.
Non-final Office Action dated Nov. 13, 2019 issued in corresponding U.S. Appl. No. 14/942,244.
Final Office Action dated Apr. 16, 2020 issued in corresponding U.S. Appl. No. 14/942,244.
Communication pursuant to Article 94(3) EPC dated Jun. 5, 2020 issued in corresponding European Patent Application No. 13 151 394.7.
Non-Final Office Action dated Sep. 9, 2016 in corresponding U.S. Appl. No. 13/603,048 (13 pages).
Non-Final Office Action dated Sep. 28, 2016 in corresponding U.S. Appl. No. 14/942,244 (15 pages).

(56) References Cited

OTHER PUBLICATIONS

Final Office Action U.S. Appl. No. 14/942,244 dated Apr. 10, 2017.
Extended European Search Report dated Jan. 12, 2017 in corresponding European Application No. 13151247.7.
Extended European Search Report dated Jan. 12, 2017 in corresponding European Application No. 13151245.1.
Extended European Search Report dated Jan. 18, 2017 in corresponding European Application No. 13151246.9.
Partial European Search Report dated Jan. 30, 2017 in corresponding European Application No. 13151394.7.
Extended European Search Report dated Feb. 2, 2017 in corresponding European Application No. 13151396.2.
Extended European Search Report dated Feb. 3, 2017 in corresponding European Application No. 13151401.0.
Final Office Action dated Mar. 24, 2016 in corresponding U.S. Appl. No. 13/603,048 (12 pages).
Final Office Action dated Mar. 24, 2016 in corresponding U.S. Appl. No. 13/603,015 (10 pages).
Final Office Action dated Mar. 24, 2016 in corresponding U.S. Appl. No. 13/602,893 (23 pages).
Non-final Office Action dated Dec. 8, 2020 issued in corresponding U.S. Appl. No. 14/942,244 (33 pgs.).

* cited by examiner

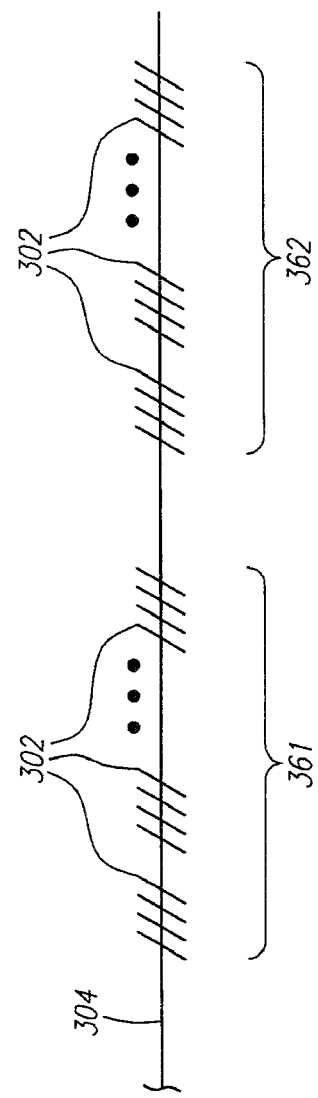

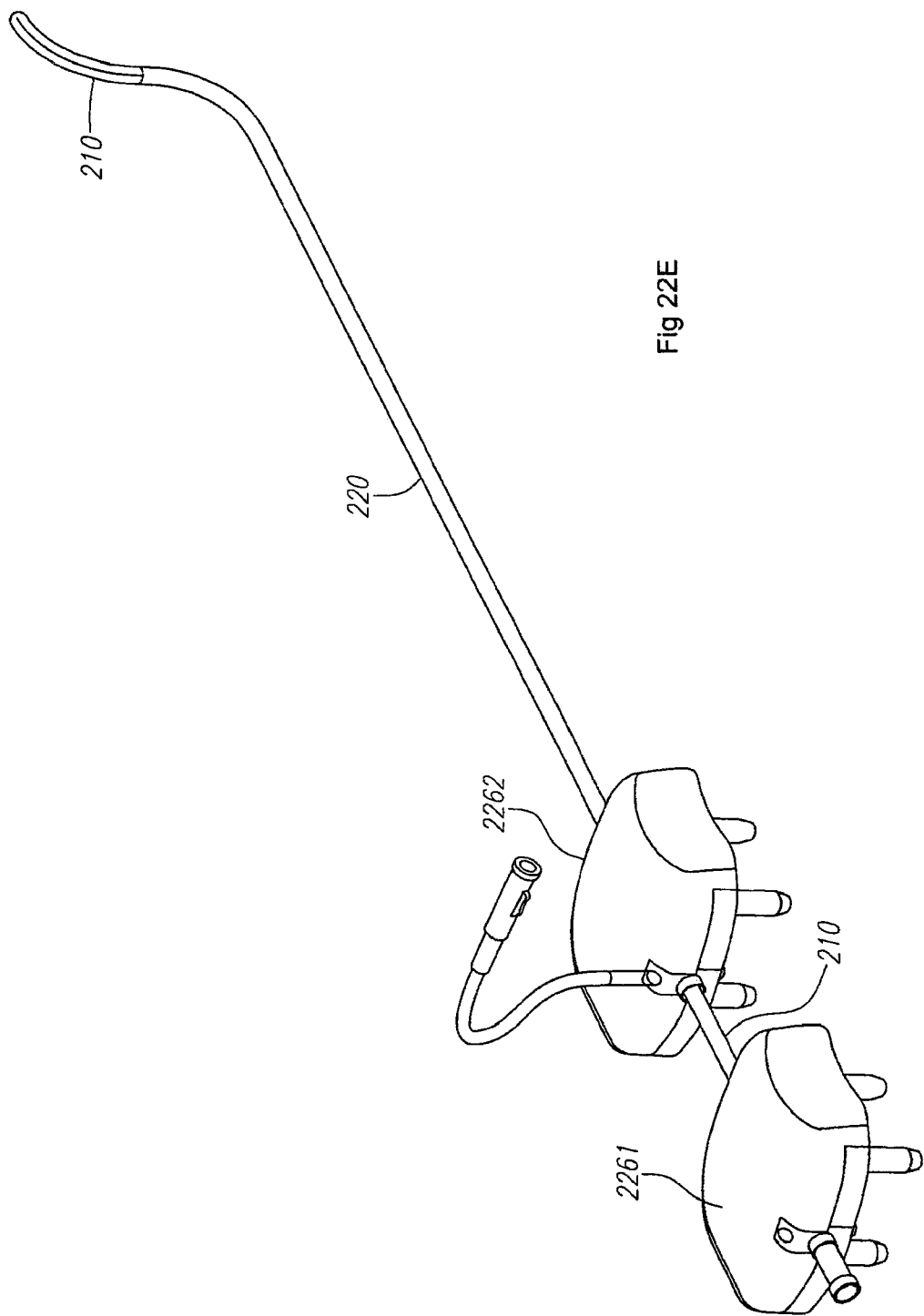

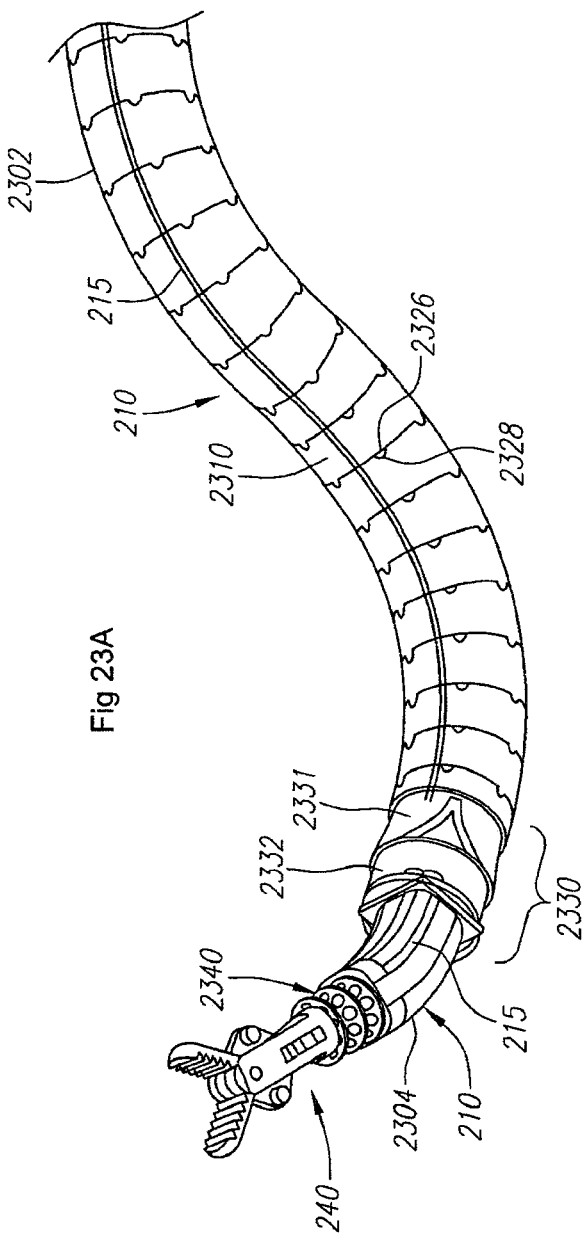

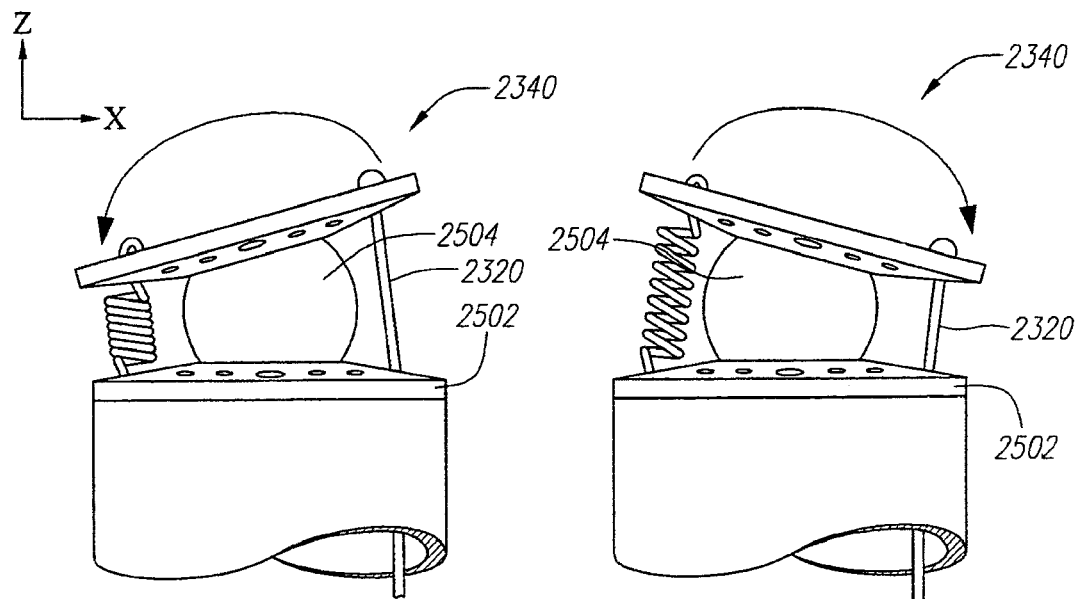
Fig 25C
Fig 25E
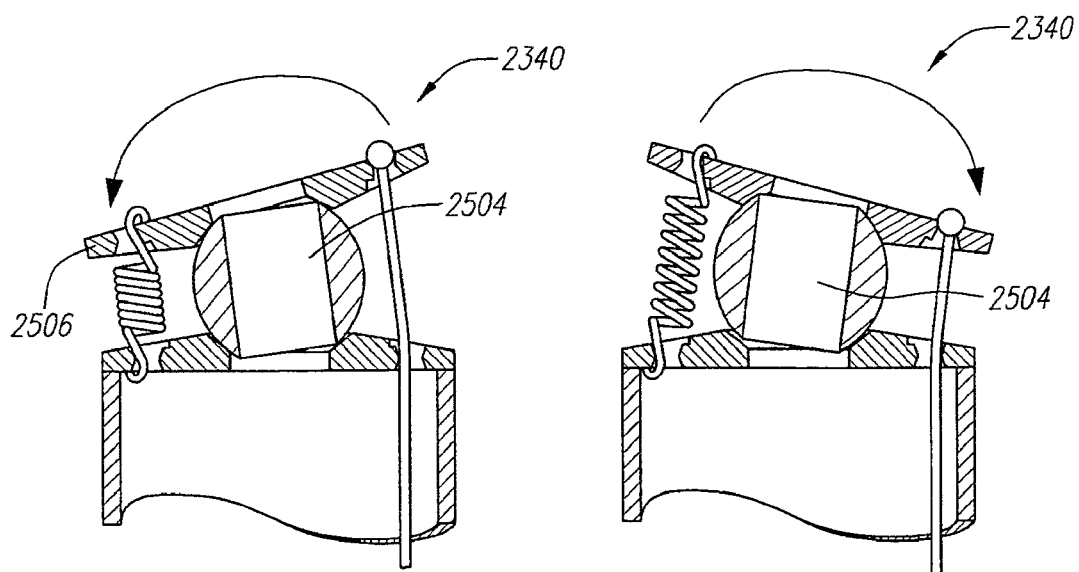
Fig 25D
Fig 25F

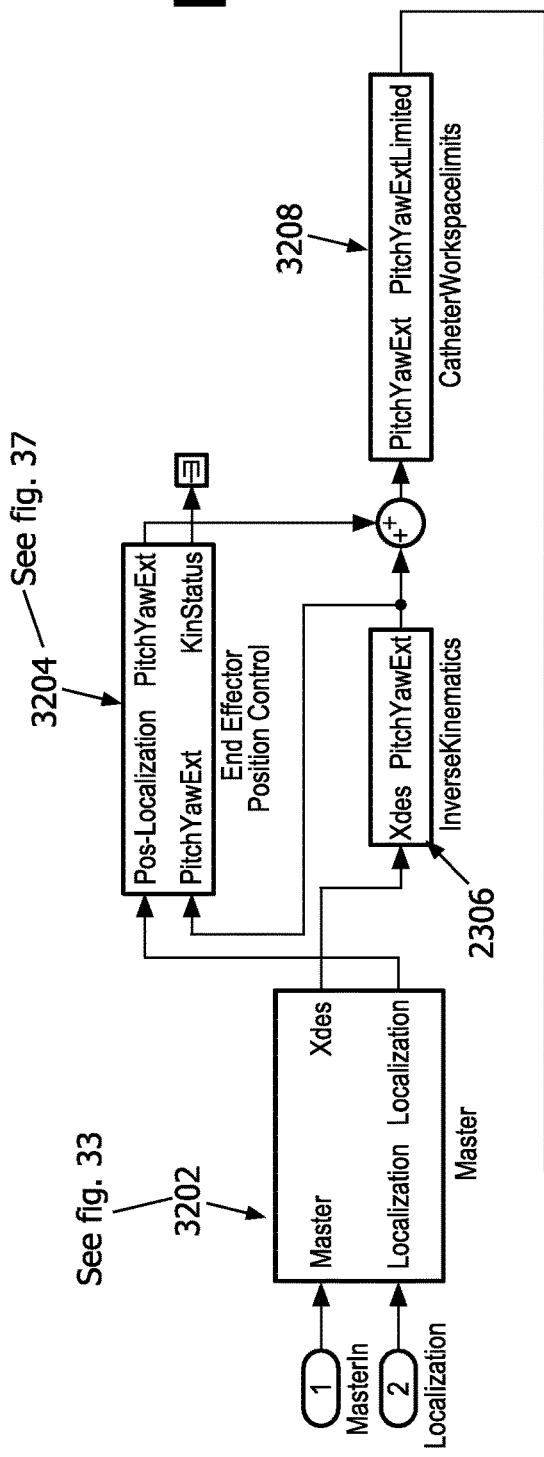
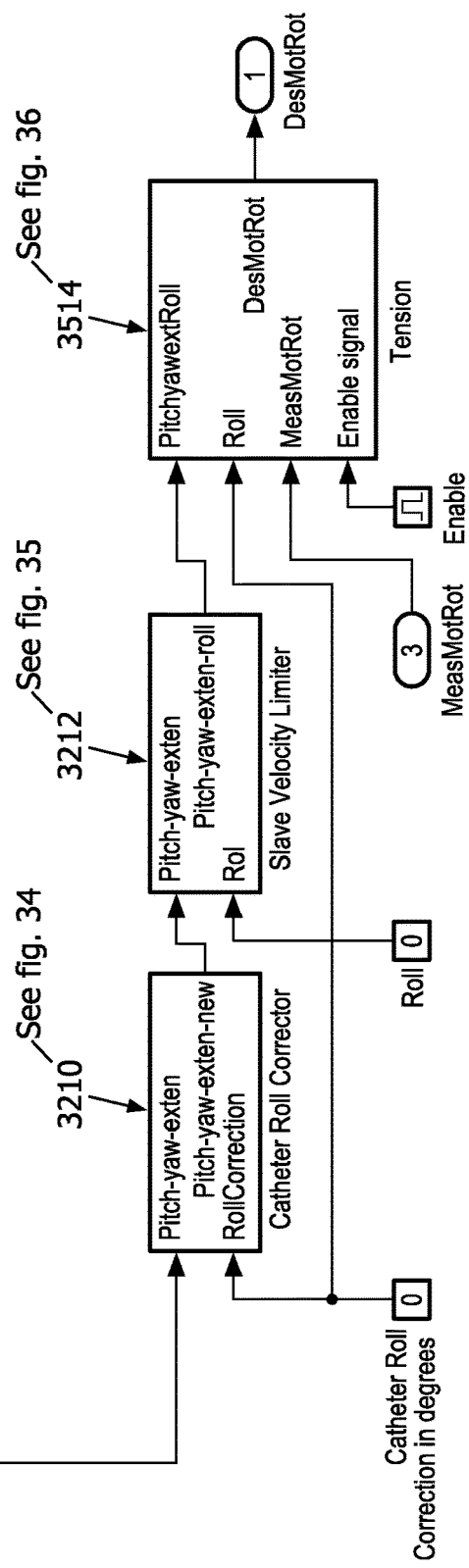
FIG. 32

Forward Kinematics:
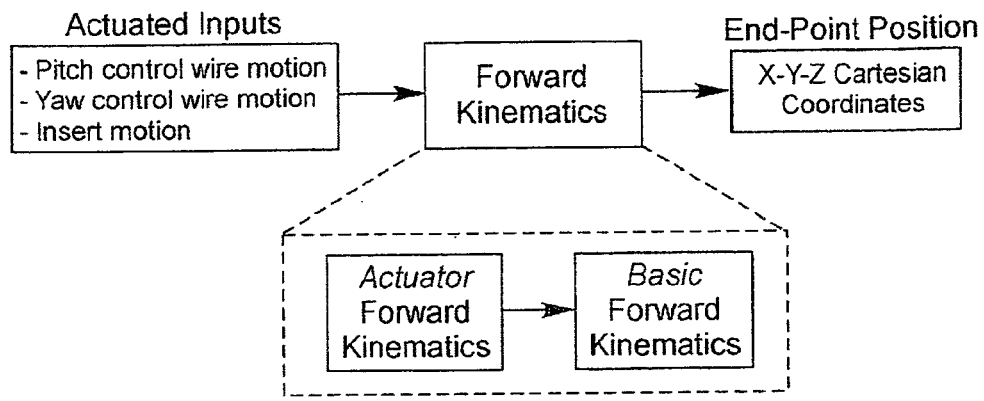
Inverse Kinematics:
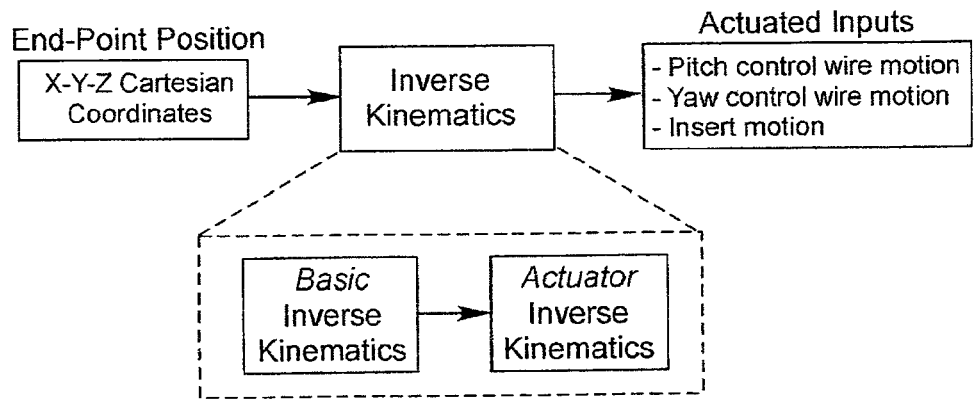
Fig 38

INSTRUMENT SYSTEMS AND METHODS UTILIZING OPTICAL FIBER SENSOR

CROSS-REFERENCE TO RELATED APPLICATION

The present application is a divisional of U.S. patent application Ser. No. 12/192,033 filed on Aug. 14, 2008, which claims the benefit under 35 U.S.C. § 119 to U.S. Provisional Application No. 60/964,773, filed on Aug. 14, 2007, the contents of which is incorporated herein by reference as though set forth in full.

The present application may also be related to subject matter disclosed in the following applications, the contents of which are also incorporated herein by reference as though set forth in full: U.S. patent application Ser. No. 10/923,660, entitled "System and Method for 3-D Imaging", filed Aug. 20, 2004; U.S. patent application Ser. No. 10/949,032, entitled "Balloon Visualization for Transversing a Tissue Wall", filed Sep. 24, 2005; U.S. patent application Ser. No. 11/073,363, entitled "Robotic Catheter System", filed Mar. 4, 2005; U.S. patent application Ser. No. 11/173,812, entitled "Support Assembly for Robotic Catheter Assembly", filed Jul. 1, 2005; U.S. patent application Ser. No. 11/176,954, entitled "Instrument Driver for Robotic Catheter System", filed Jul. 6, 2005; U.S. patent application Ser. No. 11/179,007, entitled "Methods Using A Robotic Catheter System", filed Jul. 6, 2005; U.S. patent application Ser. No. 11/185,432, entitled "System and method for denaturing and fixing collagenous tissue", filed Jul. 19, 2005; U.S. patent application Ser. No. 11/202,925, entitled "Robotically Controlled Intravascular Tissue Injection System", filed Aug. 12, 2005; U.S. patent application Ser. No. 11/331,576, entitled "Robotic Catheter System", filed Jan. 13, 2006; U.S. patent application Ser. No. 11/418,398, entitled "Robotic Catheter System", filed May 3, 2006; U.S. patent application Ser. No. 11/481,433, entitled "Robotic Catheter System and Methods", filed Jul. 3, 2006; U.S. patent application Ser. No. 11/637,951, entitled "Robotic Catheter System and Methods", filed Dec. 11, 2006; U.S. patent application Ser. No. 11/640,099, entitled "Robotic Catheter System and Methods", filed Dec. 14, 2006; U.S. patent application Ser. No. 11/678,001, entitled Apparatus for Measuring Distal Forces on a Working Instrument, filed Feb. 22, 2007; U.S. patent application Ser. No. 11/678,016, entitled Method of Sensing Forces on a Working Instrument, filed Feb. 22, 2007; U.S. patent application Ser. No. 11/690,116, entitled Fiber Optic Instrument Sensing System, filed Mar. 22, 2007; U.S. patent application Ser. No. 12/032,622, entitled Instrument Driver Having Independently Rotatable Carriages, filed Feb. 15, 2008; U.S. patent application Ser. No. 12/032,634, entitled Support Structure for Robotic Medical Instrument filed Feb. 15, 2008; U.S. patent application Ser. No. 12/032,626, entitled Instrument Assembly for Robotic Instrument System, filed Feb. 15, 2008; U.S. patent application Ser. No. 12/032,639, entitled Flexible Catheter instruments and Methods, filed Feb. 15, 2008; U.S. application Ser. No. 12/106,254, entitled Optical Fiber Shape Sensing Systems, filed on Apr. 18, 2008; and U.S. application Ser. No. 12/114,720, entitled Apparatus, Systems and Methods for Forming a Working Platform of a Robotic Instrument System by Manipulation of Components Having Controllable Rigidity," filed on May 2, 2008.

The present application may also be related to subject matter disclosed in the following provisional applications, the contents of which are also incorporated herein by reference as though set forth in full: U.S. Provisional Patent Application No. 60/550,961, entitled "Robotic Catheter System," filed Mar. 5, 2004; U.S. Provisional Patent Application No. 60/750,590, entitled "Robotic Catheter System and Methods", filed Dec. 14, 2005; U.S. Provisional Patent Application No. 60/756,136, entitled "Robotic Catheter System and Methods", filed Jan. 3, 2006; U.S. Provisional Patent Application No. 60/776,065, entitled "Force Sensing for Medical Instruments", filed Feb. 22, 2006; U.S. Provisional Patent Application No. 60/785,001, entitled "Fiberoptic Bragg Grating Medical Instrument", filed Mar. 22, 2006; U.S. Provisional Patent Application No. 60/788,176, entitled "Fiberoptic Bragg Grating Medical Instrument", filed Mar. 31, 2006; U.S. Provisional Patent Application No. 60/801,355, entitled "Sheath and Guide Catheter Apparatuses For A Robotic Catheter System With Force Sensing", filed May 17, 2006; U.S. Provisional Patent Application No. 60/801,546, entitled "Robotic Catheter System and Methods", filed May 17, 2006; U.S. Provisional Patent Application No 60/801,945, entitled "Robotic Catheter System and Methods", filed May 18, 2006; U.S. Provisional Patent Application No. 60/833,624, entitled "Robotic Catheter System and Methods", filed Jul. 26, 2006; U.S. Provisional Patent Application No. 60/835,592, entitled "Robotic Catheter System and Methods", filed Aug. 3, 2006; U.S. Provisional Patent Application No. 60/838,075, entitled "Robotic Catheter System and Methods", filed Aug. 15, 2006; U.S. Provisional Patent Application No. 60/840,331, entitled "Robotic Catheter System and Methods", filed Aug. 24, 2006; U.S. Provisional Patent Application No. 60/843,274, entitled "Robotic Catheter System and Methods", filed Sep. 8, 2006; U.S. Provisional Patent Application No, 60/873,901, entitled "Robotic Catheter System and Methods", filed Dec. 8, 2006; U.S. Provisional Patent Application No. 60/879,911, entitled "Robotic Catheter System and Methods", filed Jan. 10, 2007; U.S. Provisional Patent Application No, 60/899,048, entitled "Robotic Catheter System", filed Feb. 8, 2007; U.S. Provisional Patent Application No. 60/900,584, entitled "Robotic Catheter System and Methods", filed Feb. 8, 2007; U.S. Provisional Patent Application No. 60/902,144, entitled, Flexible Catheter Instruments and Methods, filed on Feb. 15, 2007; U.S. Provisional Patent Application No. 60/925,449, entitled Optical Fiber Shape Sensing Systems, filed Apr. 20, 2007; and U.S. Provisional Patent Application No. 60/925,472, entitled Systems and Methods for Processing Shape Sensing Data, filed Apr. 20, 2007.

FIELD OF INVENTION

The invention relates generally to robotically controlled systems such as telerobotic surgical systems.

BACKGROUND

Robotic interventional systems and devices are well suited for use in performing minimally invasive medical procedures as opposed to conventional procedures that involve opening the patient's body to permit the surgeon's hands to access internal organs. Traditionally, surgery utilizing conventional procedures meant significant pain, long recovery times, lengthy work absences, and visible scarring. However, advances in technology have led to significant changes in the field of medical surgery such that less invasive surgical procedures are increasingly popular, in particular, minimally invasive surgery (MIS). A "minimally invasive medical procedure" is generally considered a procedure that is performed by entering the body through the skin, a body cavity, or an anatomical opening utilizing small incisions rather than larger, more invasive open incisions in the body.

Various medical procedures are considered to be minimally invasive including, for example, mitral and tricuspid valve procedures, patent formen ovale, atrial septal defect surgery, colon and rectal surgery, laparoscopic appendectomy, laparoscopic esophagectomy, laparoscopic hysterectomies, carotid angioplasty, vertebroplasty, endoscopic sinus surgery, thoracic surgery, donor nephrectomy, hypodermic injection, air-pressure injection, subdermal implants, endoscopy, percutaneous surgery, laparoscopic surgery, arthroscopic surgery, cryosurgery, microsurgery, biopsies, videoscope procedures, keyhole surgery, endovascular surgery, coronary catheterization, permanent spinal and brain electrodes, stereotactic surgery, and radioactivity-based medical imaging methods. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. Images of the body interior are transmitted to an external video monitor to allow a surgeon to analyze the images, make a diagnosis, visually identify internal features, and perform surgical procedures based on the images presented on the monitor.

MIS procedures may involve minor surgery as well as more complex operations. Such operations may involve robotic and computer technologies, which have led to improved visual magnification, electromechanical stabilization and reduced number of incisions. The integration of robotic technologies with surgeon skill into surgical robotics enables surgeons to perform surgical procedures in new and more effective ways.

Although MIS techniques have advanced, physical limitations of certain types of medical equipment still have shortcomings and can be improved. For example, during a MIS procedure, catheters (e.g., a sheath catheter, a guide catheter, an ablation catheter, etc.), endoscopes or laparoscopes may be inserted into a body cavity duct or vessel. A catheter is an elongated tube that may, for example, allow for drainage or injection of fluids or provide a path for delivery of working or surgical instruments to a surgical or treatment site. In known robotic instrument systems, however, the ability to control and manipulate system components such as catheters and associated working instruments may be limited due, in part, to a surgeon not having direct access to the target site and not being able to directly handle or control the working instrument at the target site.

More particularly, MIS diagnostic and interventional operations require the surgeon to remotely approach and address the operation or target site by using instruments that are guided, manipulated and advanced through a natural body orifice such as a blood vessel, esophagus, trachea, small intestine, large intestine, urethra, or a small incision in the body of the patient. In some situations, the surgeon may approach the target site through both a natural body orifice as well as a small incision in the body.

For example, one or more catheters and other surgical instruments used to treat cardiac arrhythmias such as atrial fibrillation (AF), are inserted through an incision at the femoral vein near the thigh or pelvic region of the patient, which is at some distance away from the operation or target site. In this example, the operation or target site for performing cardiac ablation is in the left atrium of the heart. Catheters are guided (e.g., by a guide wire, etc.) manipulated, and advanced toward the target site by way of the femoral vein to the inferior vena cava into the right atrium through the interatrial septum to the left atrium of the heart. The catheters may be used to apply cardiac ablation therapy to the left atrium of the heart to restore normal heart function.

However, controlling one or more catheters that are advanced through naturally-occurring pathways such as blood vessels or other lumens via surgically-created wounds of minimal size, or both, can be a difficult task. Remotely controlling distal portions of one or more catheters to precisely position system components to treat tissue that may lie deep within a patient, e.g., the left atrium of the heart, can also be difficult. These difficulties are due in part to limited control of movement and articulation of system components, associated limitations on imaging and diagnosis of target tissue, and limited abilities and difficulties of accurately determining the shape and/or position of system components and distal portions thereof within the patient. These limitations can complicate or limit the effectiveness of surgical procedures performed using minimally invasive robotic instrument systems.

For example, referring to FIG. 1, a typical field of view or display 10 of a catheter includes a representation 12 of a catheter and an image 14 of a catheter. The catheter representation 12 is in the form of "cartoon object" that is created based on a position of the catheter determined according to a kinematics model. The image 14 is generated using an imaging modality such as fluoroscopy.

A kinematics model is related to the motion and shape of an instrument, without consideration of forces on the instrument that bring about that motion. In other words, a kinematics model is based on geometric parameters and how a position of the instrument changes relative to a pre-determined or reference position or set of coordinates. One example of a kinematics model that may be used in non-invasive robotic applications receives as an input a desired or selected position of the instrument, e.g., a position of a distal portion of the instrument within a portion of the heart, and outputs a corresponding shape or configuration of the instrument, e.g., with reference to a current or known shape or configuration, that results in positioning of the instrument according to the input.

A fluoroscopic system may be utilized to image, or "visualize", the elongate instrument or a portion thereof. A drawback of known fluoroscopic imaging systems is that it they are projection based such that depth information is lost. As a result, true three-dimensional location of objects such as an elongate instrument in the field of view of the fluoroscope is lost as a result of generating a two-dimensional fluoroscopic image. Thus, even if it is possible to obtain. accurate x-y or two-dimensional data, it may be difficult or impossible to accurately determine the location of a catheter in three-dimensional space. Examples of fluoroscopy instruments and associated methods are described in further detail in U.S. application Ser. No. 11/637,951, the contents of which were previously incorporated by reference.

In the example illustrated in FIG. 1, the shapes of the representation 12 and image 14 are generally consistent, but in some applications, the position and/or shape of a catheter or elongate instrument may differ and inaccurately reflect the shape and/or position of the instrument, which may result in complications during surgical procedures. Such mismatches may be interpreted as a problem associated with the kinematics model or controls or sensing algorithms, or as a result of contact between the subject instrument and a nearby object, such as tissue or another instrument.

A process called "registration" may be performed to spatially associate the two coordinate systems in three dimensions. Registration involves moving the elongate instrument to one or more positions, imaging the instrument with one or more positions of the fluoroscopic imaging device (e the C-arm), and analyzing the images to deduce the coordinate system of the elongate instrument in relation to the coordinate system of the fluoroscopic imaging device. This process, however, can be tedious, and it is relatively easy for the elongate instrument to go out of alignment relative to the other pertinent coordinate systems.

BRIEF DESCRIPTION OF THE DRAWINGS

The present disclosure will be readily understood by the following detailed description, taken in conjunction with accompanying drawings, illustrating by way of examples the principles of the present disclosure. The drawings illustrate the design and utility of preferred embodiments of the present disclosure, in which like elements are referred to by like reference symbols or numerals. The objects and elements in the drawings are not necessarily drawn to scale, proportion or precise positional relationship; instead emphasis is focused on illustrating the principles of the present disclosure.

FIG. 3C illustrates a core of an optical fiber sensor constructed according to another embodiment that includes sets of Fiber Bragg Gratings having different reflectivities;

FIGS. 22A-F illustrate a robotic instrument or surgical system in which embodiments of the invention may be implemented wherein FIG. 22A illustrates a robotic medical instrument system, FIG. 22B illustrates an operator workstation including a master input device and data gloves, FIG. 22C is a block diagram of a system architecture of a robotic medical instrument system in which embodiments may be implemented or with which embodiments may be utilized, FIG. 22D illustrates a setup joint or support assembly of a robotic instrument system with which embodiments may be utilized, FIG. 22E is a rear perspective view of a flexible catheter assembly of a robotic instrument system with which embodiments may be utilized, and FIG. 22F illustrates an instrument driver to which the flexible catheter assembly illustrated in FIG. 22E may be attached and to which an optical fiber sensor may be coupled;

FIGS. 23A-C are different views of a multi-a sheath catheter having an optical fiber sensor coupled thereto according to on embodiment;

FIGS. 25A-F are different views of an orientation platform or interface for a working instrument with which rotational apparatus embodiments as shown in FIGS. 24A-D can be utilized;

FIGS. 26A-B illustrate other configurations of a robotic instrument system in which embodiments may be utilized, wherein FIG. 26A illustrates an embodiment including three multi-segment sheath catheters, each of which has an optical fiber sensor coupled thereto, and FIG. 26B shows the configuration shown in FIG. 26A with an additional optical fiber sensor coupled to an image capture device that extends through the master sheath;

FIGS. 27-43 illustrate aspects of a control schema, kinematics, actuation coordinates for kinematics, and a block diagram of a system with which embodiments may be implemented or utilized, a sample flowchart of transforming a position vector to a haptic signal, and a block diagram of a system including haptics capability of robotic surgical systems in which embodiments of the invention may be implemented.

SUMMARY OF THE INVENTION

Figure 1:
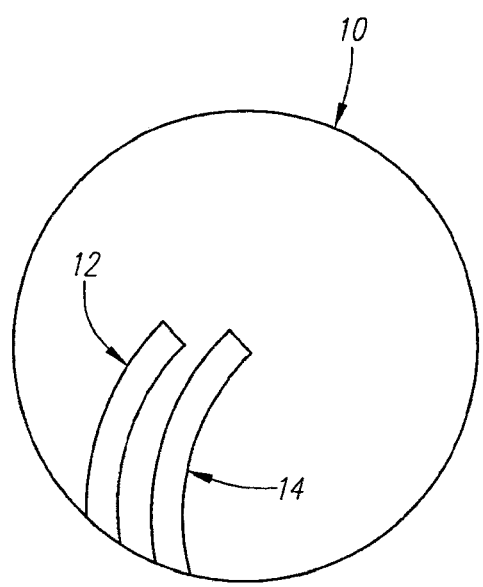
FIG. 1 generally illustrates a field of view or display that includes a representation of a catheter generated using a kinematics model and an image of a catheter.

In accordance with one embodiment, a method for mapping an internal structure of a patient with an elongate body is provided. The method includes detecting, at a plurality of instances, contact between a distal portion of an elongate body and an internal structure of the patient; determining a plurality of geometric configurations of the distal portion, the plurality of geometric configurations corresponding to the plurality of instances of contact between the distal portion and the internal structure; determining a plurality of positions of the distal portion, the plurality of positions corresponding to the plurality of geometric configurations; and generating a map of the internal structure based on the plurality of positions of the distal portion.

According to another embodiment, an instrument system that includes an elongate body having a distal portion and a controller is provided. The controller is operatively coupled to the elongate body and adapted to: detect, at a plurality of instances, contact between the distal portion and an internal structure of the patient; determine a plurality of geometric configurations of the distal portion, the plurality of geometric configurations corresponding to the plurality of instances of contact between the distal portion and the internal structure; determine a plurality of positions of the distal portion, the plurality of positions corresponding to the plurality of geometric configurations; and generate a map of the internal structure based on the plurality of positions of the distal portion.

According to yet another embodiment, an instrument system that includes an elongate sheath having a lumen, a plurality of working instruments positioned in the sheath lumen and a controller is provided. Each working instrument includes an elongate instrument body having a distal end portion that may be extended out of a distal end opening of the sheath in communication with the lumen. Each instrument body distal end portion is coupled to an optical fiber. The controller is configured to determine one or more position and/or orientation variables of the distal end portions of the respective instrument bodies based upon signals received from the optical fiber.

According to yet another embodiment, a medical instrument system that includes a controller, an elongate instrument, an optical fiber and a detector is provided. The controller is configured to control actuation of at least one servo motor. The elongate instrument is configured to move in response to actuation of the at least one servo motor. The optical fiber has a distal portion coupled to a distal portion of the instrument. The detector is operatively coupled to a proximal end of the optical fiber and is configured to detect respective signals from the optical fiber. The controller controls movement of the instrument based at least in part upon a geometric configuration of the distal portion of the instrument determined based upon an analysis of the detected portions of the signals.

According to yet another embodiment, an instrument system that includes a controller, an elongate instrument, an optical fiber, and a detector is provided. The controller is configured to control actuation of at least one servo motor. The elongate instrument has one or more control elements operatively coupled to the at least one servo motor such that the instrument moves in response to actuation of the at least one servo motor. The optical fiber has a distal portion coupled to a distal portion of the instrument. The detector is operatively coupled to a proximal end of the optical fiber and configured to detect respective signals from the optical fiber. The controller controls movement of the instrument based at least in part on spatial position data of the distal portion of the instrument determined based upon an analysis of the detected portions of the signals.

These and other aspects of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated can be considered are drawn to scale. It is to be expressly understood, however, that the drawings are for the purpose of illustration and description only and are not intended as a definition of the limits of the present disclosure. It shall also be appreciated that the features of one embodiment disclosed herein can be used in other embodiments disclosed herein. As used in the specification and in the claims, the singular form of "a", "an", and "the" include plural referents unless the context clearly dictates otherwise.

DETAILED DESCRIPTION OF THE ILLUSTRATED EMBODIMENTS

Embodiments of the invention are related to systems, apparatus and methods including or involving the use of optical fiber sensors, e.g., Fiber-Bragg sensors, which may be used to provide accurate shape and/or position data of an elongate instrument.

Figure 2A:
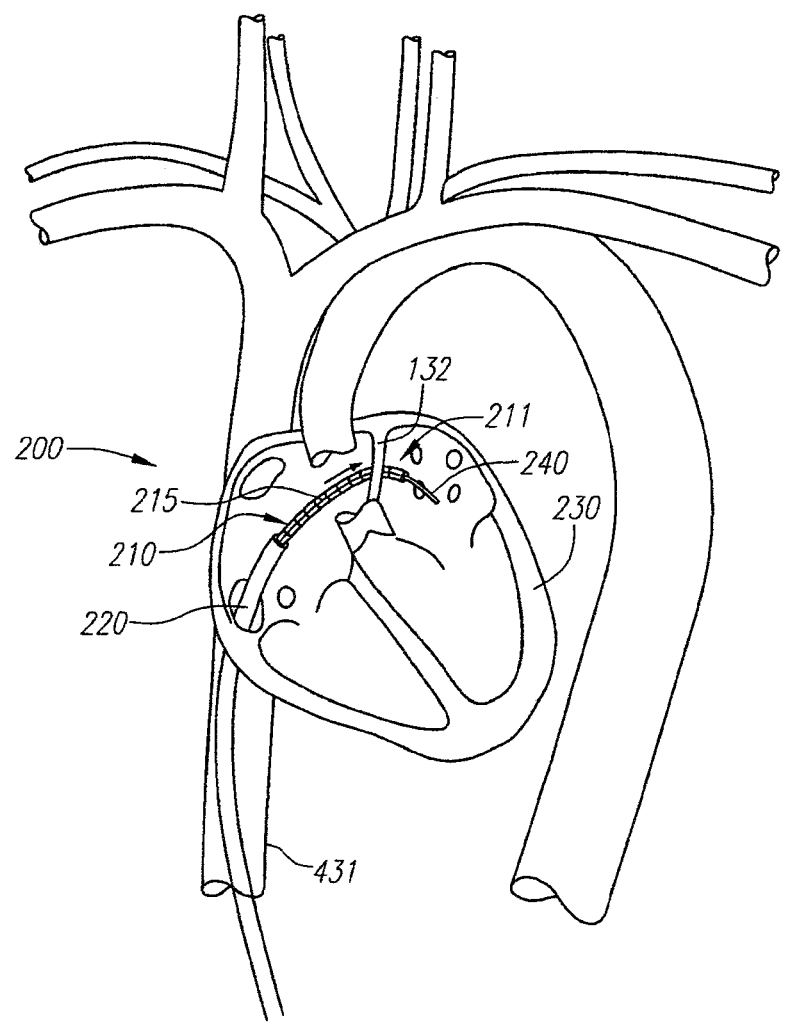
FIG. 2A illustrates a surgical apparatus constructed according to one embodiment that includes an optical fiber sensor attached to or integral with an elongate surgical instrument.

Referring to FIG. 2A, according to one embodiment, one or more components of a robotically controlled instrument 200 of a robotic surgical system include an optical fiber or fiber sensor 215 (referred to as optical fiber sensor or fiber 215), Which is coupled to, or an integral part of, an elongate instrument body 210. Data based on light reflected by gratings of the fiber 215 may be used to determine the shape and/or position of the elongate instrument, which may be a catheter, such as a guide catheter. In the illustrated embodiment, the elongate instrument or catheter 210 is a part of a robotically controlled instrument 200 that it utilized to position a bendable distal end portion 211 of the catheter 210 and one or more working instruments 240 at a target site within a patient. The particular working instrument 240 employed may depend on the target tissue and manner in which the instrument 200 is inserted or advanced into the patient.

Figure 2B:
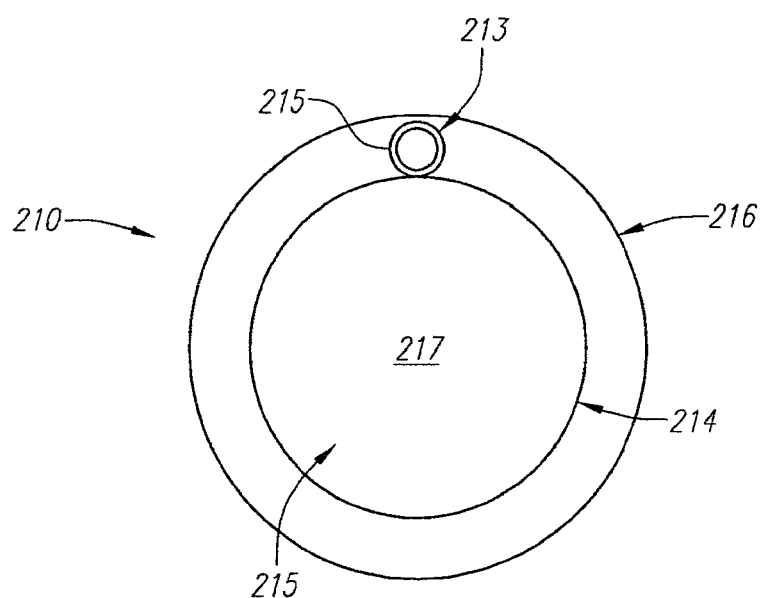
FIG. 2B is a cross-sectional view of an elongate instrument constructed according to one embodiment and that defines a central lumen and a lumen defined through a wall of the catheter in which an optical fiber sensor may be positioned.

The optical fiber sensor 215 can be attached or coupled to an elongate instrument or catheter 210 in various ways. Referring to FIG. 2B, in one embodiment, the optical fiber sensor 215 extends through a central or other lumen 217 defined by the catheter 210. According to another embodiment, the optical fiber sensor 215 extends through a lumen 213 defined through a wall of the catheter 210, i.e., through a lumen 213 defined between an inner wall 214 and an outer wall 216 of the catheter 210. FIG. 2B illustrates a single lumen 213 defined within a catheter 210 wall to accommodate a single optical fiber sensor 215 and a single lumen 217, but in other embodiments, multiple lumens 213, 217 may be defined, and an optical fiber sensor 215 may extend through some or all of the multiple lumens 213, 217. In other embodiments, the optical fiber sensors 215 can be coupled, bonded or attached to the inner wall 214 or to the outer wall 215 as appropriate. The inner wall 214 may also define a groove in which a fiber 215 may be positioned. In yet other embodiments, an optical fiber sensor 215 can be coupled to or integral with an outer surface 216 using, for example, a suitable adhesive or bonding agent and/or the fiber 215 may be positioned within an aperture or groove that is formed within the outer wall 216. Further, the optical fiber 215 can be coupled to a catheter or other instrument 210 in such a manner that a portion of the optical fiber 215 is coupled at a known reference location on the proximal potion of the instrument 210.

For ease of explanation, this specification refers to an optical fiber sensor 215 that is coupled to or integral with a catheter 210 or other system component in a non-limiting manner. Thus, while certain figures may illustrate an optical fiber sensor 215 extending along a surface of a catheter 210 for ease of illustration, it should be understood that in practice, one or multiple optical fiber sensors 215 may extend through one or more lumens 213, 217 of one or more instruments depending on the configuration employed.

Referring again to FIG. 2A, one manner in which robotic intravascular systems including an elongate instrument 210 having an optical fiber sensor 215 coupled thereto or integral therewith may be utilized is to position the catheter 210 or other working instrument 240 within the heart 230, e.g., to diagnose, treat or ablate endocardial tissue. In the illustrated application, a robotically controlled instrument 200 including a catheter or guide instrument 210 and a sheath instrument 220 is positioned within the heart 230. FIG. 2A depicts delivery of the instrument 200 utilizing a standard atrial approach in which the robotically controlled catheter 210 and sheath 220 pass through the inferior vena cava and into the right atrium. An image capture device (not illustrated in FIG. 2), such as an endoscope or intracardiac echo ("ICE") sonography catheter (not shown in FIG. 1), may be advanced into the right atrium to provide a field of view upon the interatrial septum. The catheter 210 may be driven to the septum wall 132, and the septum 132 may be crossed using a conventional technique of first puncturing the fossa ovalis location with a sharpened device, such as a needle or wire, passed through a working lumen of the catheter 110, then passing a dilator or other working instrument 240 over the sharpened device and withdrawing the sharpened device to leave the dilator 240, over which the catheter 210 may be advanced.

Various working instruments 240 (not shown in FIG. 1) may be delivered through the lumen of the catheter 210 as necessary and depending on the surgical application. For example, for treatment of atrial fibrillation, the working instrument 240 may be an ablation catheter that delivers targeted radio frequency (RF) energy to selected endocardial tissue. Further aspects of such systems, devices and applications are described in U.S. application Ser. No. 11/176, 598, the contents of which were previously incorporated herein by reference.

An optical fiber sensor 215 may be used in various applications and may be coupled to or integral with various instruments and surgical system components, and even a patient. For example, in one embodiment, the optical fiber sensor 215 serves as a localization sensor, which may be used to "localize" or monitor the position and/or orientation of various objects or system components involved in a surgical procedure. The optical fiber sensor 215 may also be utilized in other applications involving registration, calibration, force calculation and feedback, improved accuracy, mechanical interfacing or "connectorization," and fiber-based diagnostics. Further aspects of embodiments of the invention and systems in which embodiments may be utilized are described in further detail with reference to FIGS. 3A-49.

Figure 3A:
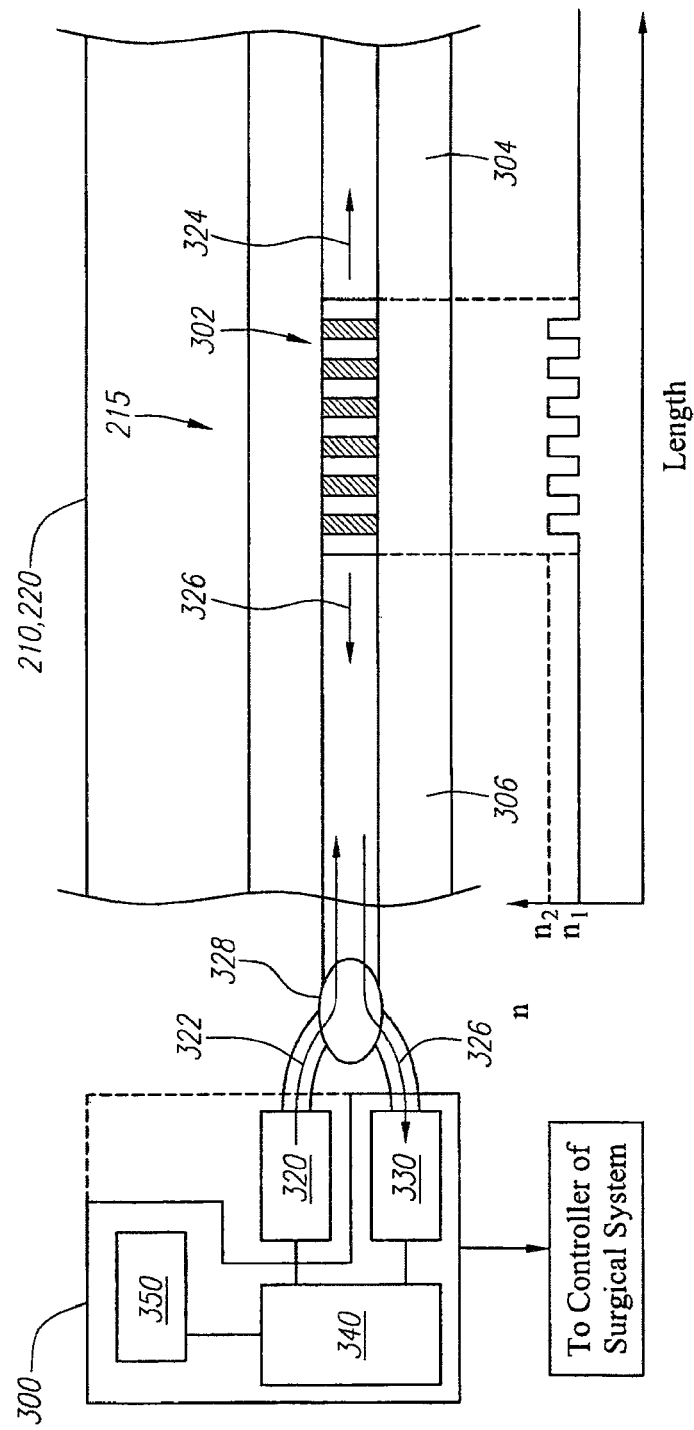
FIG. 3A schematically illustrates a system for use with optical fiber sensors having one or more Fiber Bragg Gratings written or formed therein and that are coupled to or integral with one or more components of a robotic surgical system.

Referring to FIG. 3A, an optical fiber sensor 215 constructed according to one embodiment includes a fiber core 304 surrounded by a cladding 306. The core 304 includes a distributed Bragg reflector, such as one or more Fiber Bragg gratings or FBGs 302 (generally referred to as FBGs or gratings 302), which are formed within or written into the core 304. FBGs 302 can be inscribed or written into the core 304 of a fiber 215, e.g., in a periodic manner, using various known methods and devices. For example, an ultraviolet (UV) laser may be used to "write" a periodic variation of refractive index (n) into the core 304 of a photosensitive germanium-doped silica fiber. Various types and arrangements of FBGs 302 may also be utilized in embodiments including, for example, uniform, chirped, tilted, superstructure, uniform positive-only, Gaussian-Apodized Index FBGs. For ease of explanation, this specification refers generally to one or ore FBGs 302 generally, but it should be understood that different numbers, types and arrangements of FBGs 302 may be utilized in embodiments, and that various system components may include fibers 215 so configured.

Figure 3B:
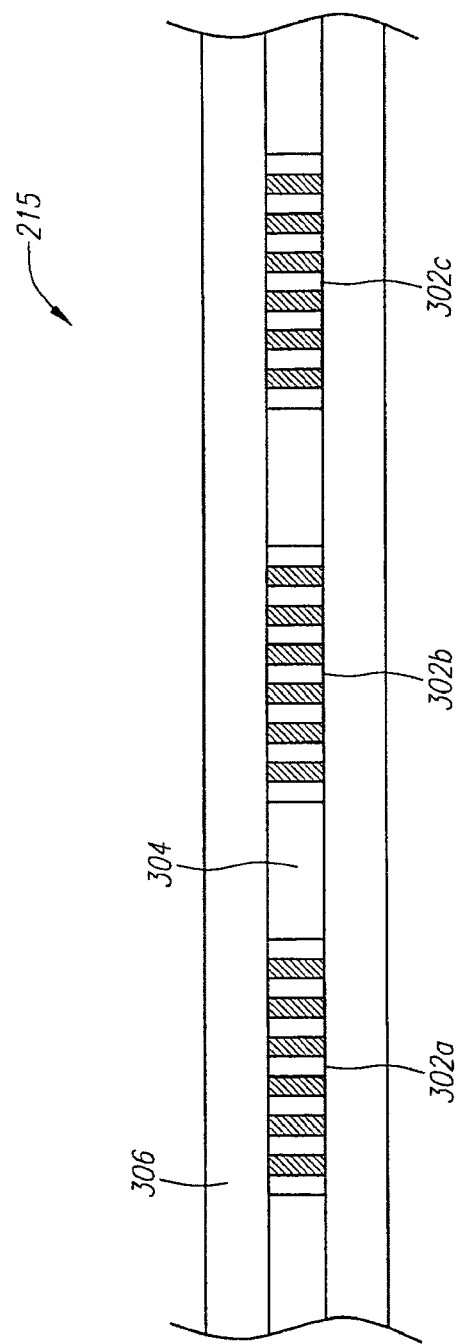
FIG. 3B illustrates a core of an optical fiber sensor constructed according to one embodiment including multiple, axially spaced Fiber Bragg Gratings.

FIG. 3A illustrates a single fiber 215 and a single FBG 302 written on or within the core 304. In other embodiments (e.g., as generally illustrated in FIGS. 3B-C), an optical fiber sensor 215 may have a fiber core 304 that includes multiple FBGs 302 or sets thereof that are axially distributed along the core 304. In certain embodiments, the FBGs 302 may be continuous, overlapping or partially overlapping.

In one embodiment, as illustrated in FIG. 3C, a core 304 may include different sets 361-362 of FBGs 302 that have different reflectivities. Although FIG. 3C illustrates sets 361, 362 having three FBGs 302 for purposes of illustration, it should be understood that different numbers of gratings may be utilized, and the number of gratings 302 in each set 361, 362 may be the same or different. For example, in the illustrated embodiment, the reflectivity of the first set 361 of FBGs 302 may be configured to have relatively low reflectivity, whereas another set 362 has slightly higher reflectivity. In one embodiment, a first fiber 215 may include gratings of a first reflectivity, and a second fiber 215 may include gratings of a second, different reflectivity.

In another embodiment, a single fiber 215 has FBGs 302 of different reflectivities, which may be suitable for use with both optical frequency domain reflectometry (ODFR) and wavelength division multiplexing (WDM) processors that are operably coupled to the same fiber 215. In this manner, embodiments combine the advantages of two different processing systems. OFDR is suited for low reflectively gratings 302 of the same wavelength and is beneficial since it may be able to handle a larger number of gratings per length of fiber 215 compared to WDM, whereas WDM is suited for high reflectivity gratings 302 of different wavelengths, and can achieve high signal-to-noise rations. Thus, embodiments may advantageously utilize both OFDR and WDM on the same fiber 215. Further aspects of OFDR and WDM processing are described in U.S. application Ser. No. 12/106,254, the contents of which were previously incorporated herein by reference.

Thus, various figures, including FIGS. 3A-C, are provided as examples of how FBGs 302 may be arranged, and it should be understood that various numbers and arrangements of FBGs 302 may be utilized, that the FBGs 302 may have the same or different reflectivities. Further, while FIG. 3A illustrates a fiber 215 having a cylindrical shape, other fiber 215 configurations and shapes can be utilized, and the outer surfaces of fibers 215 may be configured or have structural attributes (e.g., shapes or other structural features) to interface with an inner surface or corresponding structural attribute of a catheter 210 or other instrument to form a key-like arrangement that limits or prevents twisting or rotational movement of the fiber 215 within. the catheter 210.

Figure 4A:
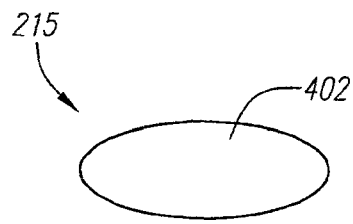
FIGS. 4A-D illustrate different optical fiber configurations or shapes that may interface with a portion of an elongate instrument or catheter to prevent twisting of the fiber.
Figure 4B:
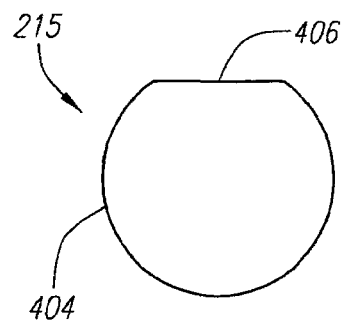
Figure 4C:
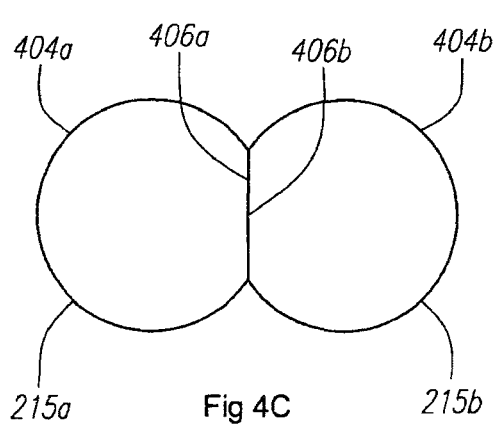
Figure 4D:
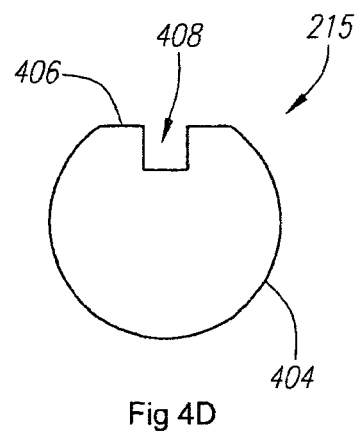
Figure 4E:
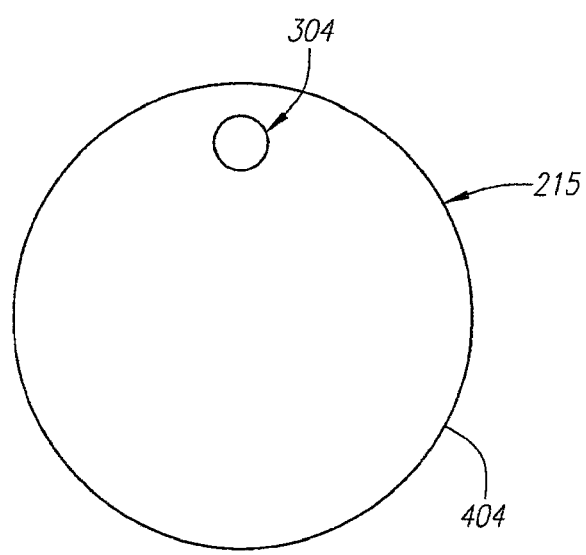
FIG. 4E illustrates another configuration of an optical fiber sensor that includes off-center core.

For example, referring to FIG. 4A, in one embodiment, an optical fiber sensor 215 has an oval-shaped outer surface 402. An inner surface of a catheter 210 may have a corresponding oval shape to mechanically limit or prevent twisting of the fiber sensor 215 within the catheter 210. According to another embodiment, referring to FIG. 4B, a fiber sensor 215 is configured such that it includes an arcuate or cylindrical outer surface 404 and a linear or flat outer surface, segment or beveled edge 406. Although one flat segment 406 is illustrated, a fiber sensor 215 may include other numbers of segments, which may be arranged symmetrically or asymmetrically. An inner surface of a catheter 210 may have a shape corresponding to the surface shown in FIG. 4B to limit or prevent rotation of the fiber sensor 215. Referring to FIG. 4C, in a further embodiment, an optical fiber sensor 215 may also comprise multiple fibers, e.g., two fibers 215a, 215b, which have mating faces 406a, 406b and respective cylindrical surfaces 404a, 404b to form a shape that resembles the number 8. Although FIG. 4C illustrates two fibers 215a, 215b, other numbers of fibers 215 may be configured to interface with each other with corresponding faces or edges 406 or other interfacing surfaces resulting in other shapes. An inner surface of a catheter 210 may have a shape corresponding to this outer surface to prevent or limit twisting or rotation of the fibers 215a, 215b. Referring to FIG. 4D, according to another embodiment, an optical fiber sensor 215 may have an edge 406 (as shown in FIG. 4B) and a deeper groove 408 formed therein. An inner surface of a catheter 210 may have a corresponding segment or protrusion configured to mate with the groove 408 to avoid twisting or rolling between the fiber 215 and the catheter 210. Although the groove 408 is shown as having a rectangular shape, other shapes may also be utilized, e.g., V-shaped grooves and other shaped grooves. Further, while embodiments are described with reference to an optical fiber 215 being disposed within an instrument such as a catheter 210, embodiments may also be applied to a fiber that is coupled to an outer surface of an instrument.

Additionally, each fiber 215 may contain a single core or comprise multiple sub-cores. In a further embodiment, referring to FIG. 4E, the optical fiber sensor 215 may include an "off-center" single core 304, which may be beneficial since the shape of the fiber 215 having one core 304 can be calculated under constrained conditions knowing the roll orientation axial strain on the catheter 210.

Further, while figures illustrate certain core 304 and FBG 302 configurations and arrangements, embodiments may utilize a single optical fiber 215 having one FBG 302, a single optical fiber 215 including a multiple FBGs 302 distributed along the core 304, multiple fibers 215, each of which includes one FBG 302, multiple fibers 215, each of which includes multiple FBGs 302 distributed along respective cores 304, or multiple fibers 215, some of which have only one FBG 302, and others that include multiple FBGs 302, and the FBGs may have the same or different reflectivities.

Certain fibers 215 may also be different sizes. According to one embodiment, the diameter of a fiber 215 configured for insertion into a patient is smaller than the diameter of a fiber 215 that is utilized externally of the patient. For example, the diameter of a fiber 215 intended for insertion into a patient may have a diameter of about 150 microns, and a diameter of a fiber 215 intended for use outside of the patient may have a diameter of about 200 microns or greater, e.g. about 500 microns.

Embodiments utilizing a fiber core 304 having a distribution of axially-spaced Bragg gratings 302, which may, for example, be continuous or substantially continuous FBGs 302 written on the at least one fiber core 304, provide for various control options. In one embodiment, a controller 340 of the output unit or readout system 300, or a controller or computer of the robotic surgical system, or combination thereof, is configured to sample the respective FBGs 302 while selected gratings 302 are sampled more frequently than others. For example, gratings 302 that are sampled more frequently may be located on a portion of the Bragg sensor optical fiber 325 coupled to a distal end portion of the instrument 210. Further, the controller 340 can be configured to actively change which Bragg gratings 302 are selected for more frequent sampling based upon, for example, movement of the instrument 210. In yet another embodiment, the controller 340 may be configured to identify a most proximal Bragg grating 302 that is selected for more frequent sampling based on a detected increase in signal amplitude from the respective grating 302 as compared to more proximal gratings 302.

Additionally, embodiments may involve instruments 210 having multiple optical fiber sensors 215, each of which has cores 304 having axially-spaced Bragg gratings 302. The controller 340 may be configured to sample respective sensor gratings 302 on the fiber cores 304, and to conduct common mode error analysis by comparing signals received from respective corresponding gratings 302 thereon. As an example of common mode analysis, first and second Bragg sensor optical fibers 215 may be attached to the same elongate instrument 210 in an identical manner except that the fibers 215 may be attached at different locations. For example, the first and second fibers 215 may be attached diametrically opposite each other of an elongate instrument 210 that has the shape of a cylinder. In this example, through analysis of the signals 236 reflected from each fiber 215, the location of the tip of the cylinder can be determined. The signals 236 from both fibers 215 can be averaged together taking into account that the fibers 215 are a known distance away from each other, and noise in the measurement can thus be reduced in this manner.

Referring again to FIG. 3A, in the illustrated system configuration, light emitted 322. by a light source 320, such a laser, is directed into the fiber core 304 through one or more suitable interfaces, couplers or connectors (generally illustrated as 328), and transmitted through the fiber core 304 to one or more FBGs 302. Light 322 may be partially transmitted 324 through the one or more FBGs 302, and partially reflected 326. Reflected light 326 propagates in the opposite direction through the core 304, through one or more suitable interfaces, couplers or connectors 328, and is detected by a detector 330 of an output or read out unit (generally identified as 300). The connectors 328 are configured to serve as interfaces between one or more fibers 215 and one or more output or read out units 300.

Figure 22A:
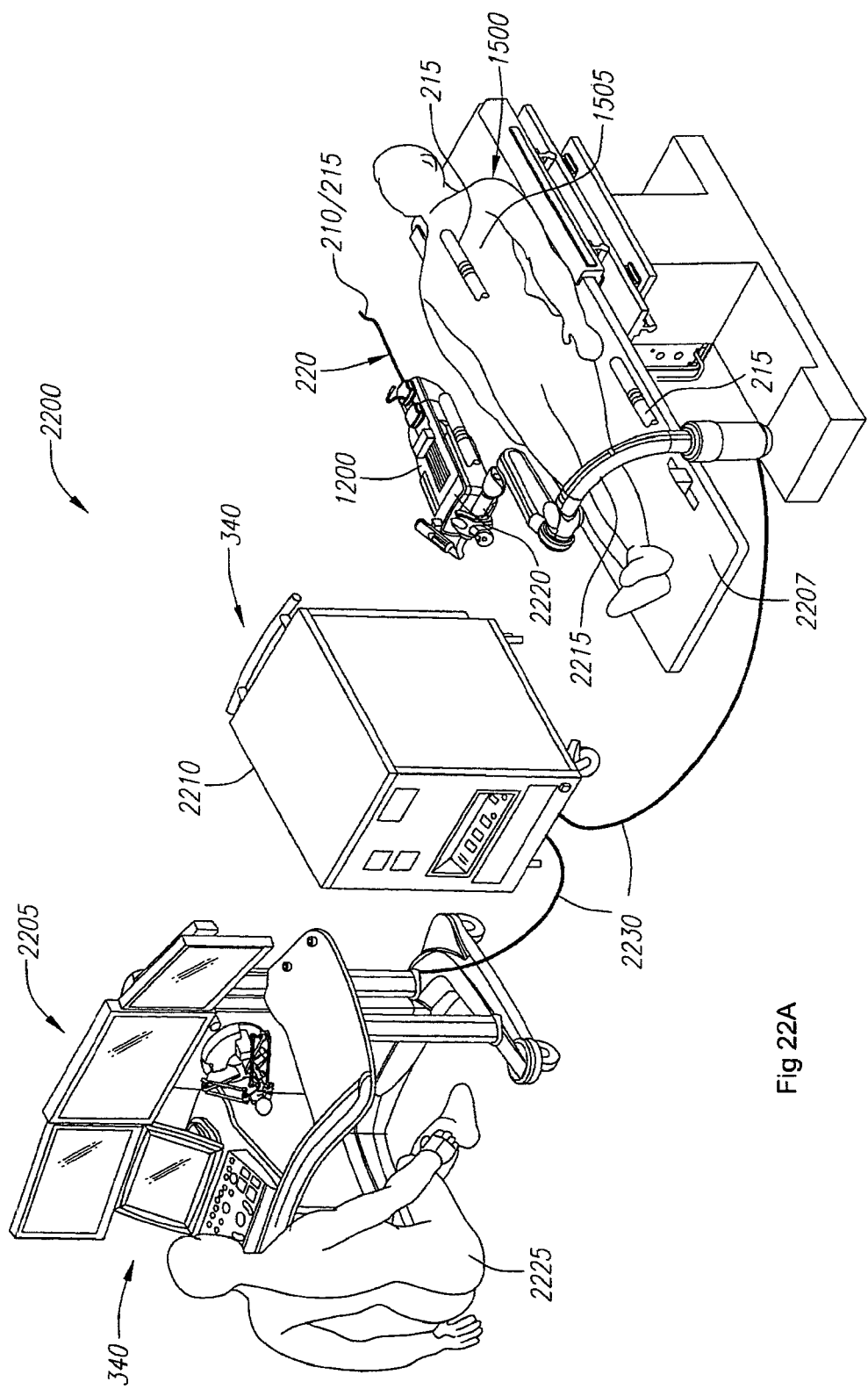
Figure 22B:
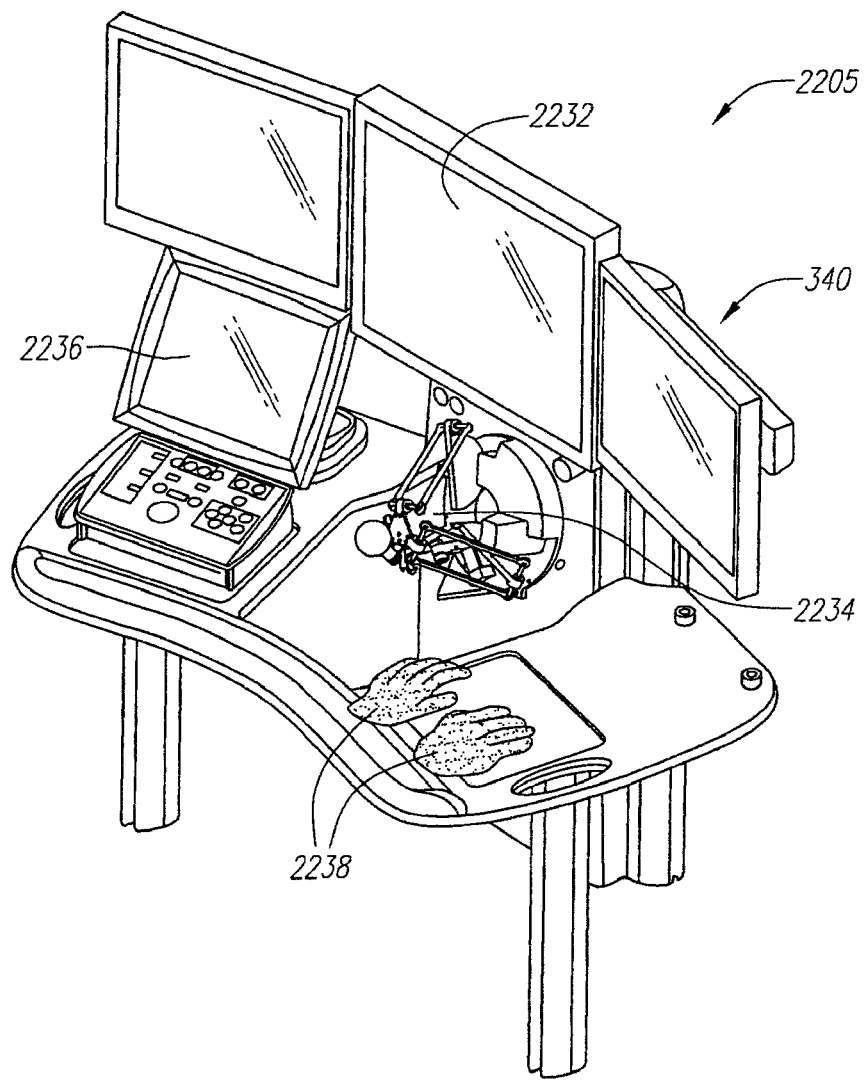
Figure 22C:
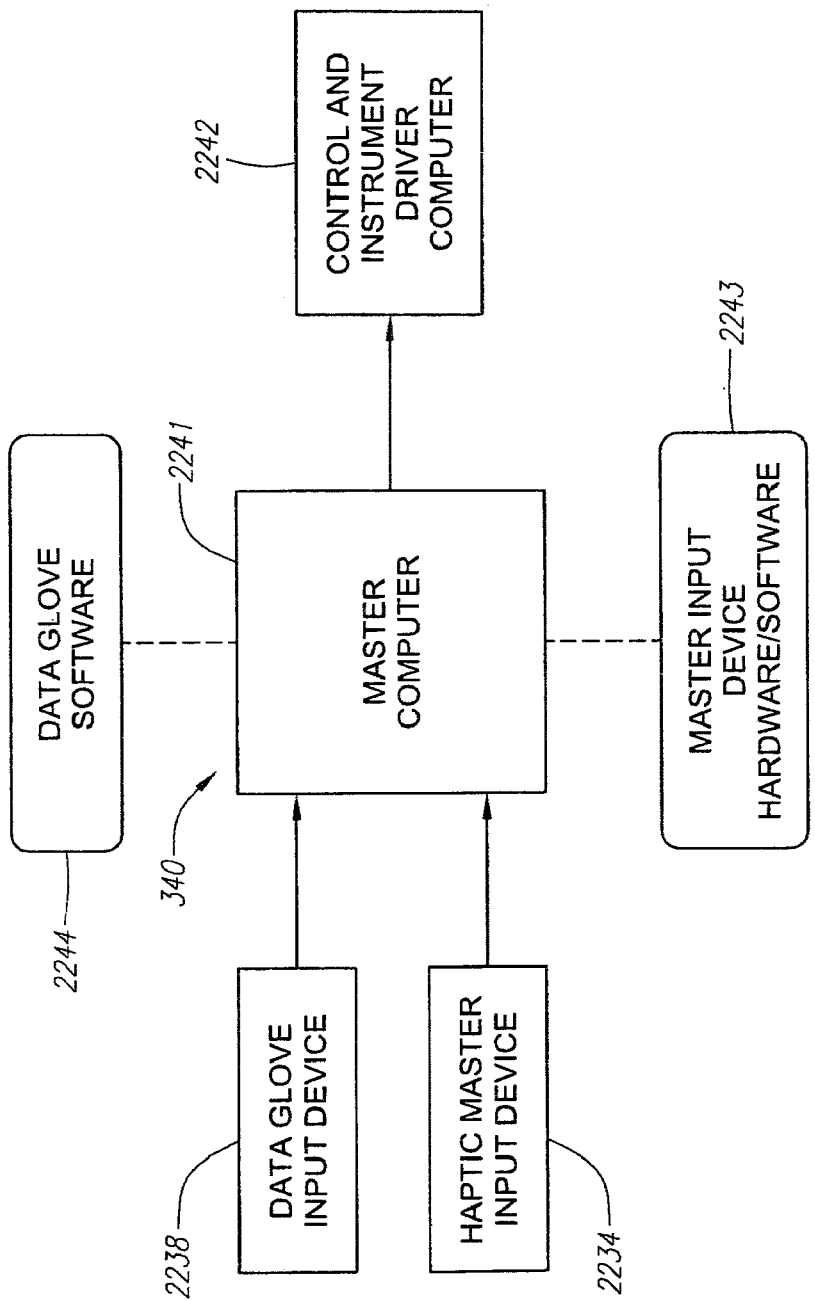

As shown in FIG. 3A, a control element 340 is located in the output unit 300. In another embodiment, a controller 340 is located in controller or computer of a robotic surgical system (e.g. as shown in FIGS. 22A-C). The output unit 300 may also be integrated within or a part of a controller or computer of a robotic surgical system. In a further embodiment, a controller 340 includes components of the output unit 300 and another computer or controller of a robotic surgical system that are operably coupled together. For ease of explanation, reference is made generally to a controller 340, but it should be understood that the controller may be a standalone component or multiple components that are operably coupled together.

In certain embodiments, the controller 340 is configured for applications involving shape, position and/or orientation of robotic surgical system components, calibration, therapeutic, diagnostic and localization procedures. The controller be implemented as hardware, software or a combination thereof, and may be a micro-controller, or a computer, which is part of, or associated with, the read out unit 300 or a robotic surgical system. The controller may process reflected light 326 and issue controls in response thereto, e.g., to adjust the shape or reposition of an instrument of a robotic surgical system (as generally illustrated in FIG. 3A), or generate representations of system components on a display.

It should be understood that the system configuration illustrated in FIG. 3A is provided to generally illustrate system components and how they may be generally configured, and that other components and configurations may be utilized. For example, although FIG. 3A illustrates a single fiber sensor 215, multiple fiber sensors 215 may also be utilized together with additional system components as necessary. Further, each fiber sensor 215 may have a dedicated detector or output unit 330 or fibers 215 may share a detector or output unit 330. Further, although FIG. 3A illustrates a separate light source 320 and output or read out unit 300, the light source 320 may also be a part of the output unit 300 (represented by dotted line). Other system configurations and/or components may be utilized, examples of which are described in further detail in U.S. patent application Ser. Nos. 11/678,001, 11/678,016 and 11/690,116 and U.S. Provisional Application Nos. 60/785,001 and. 60/788,176, the contents of which were previously incorporated by reference. Accordingly, FIG. 3A is provided to generally illustrate system components and how they may be implemented in a robotic surgical system, but other numbers and configurations and components may be utilized as necessary.

Figure 5:
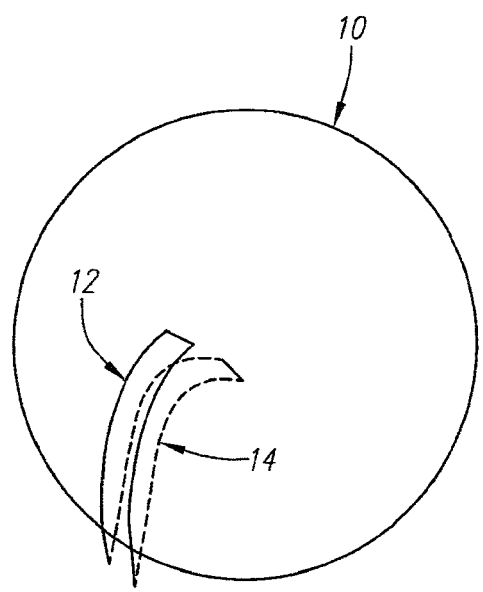
FIG. 5 generally depicts a mismatch between a shape of a representation of a catheter generated by a kinematics model and a shape of an image of a catheter acquired using an imaging modality that can be addressed or prevented with use of optical fiber sensor embodiments.

FIG. 5 illustrates one example of a situation that embodiments an optical fiber sensor 215 and related systems and methods are capable of addressing or preventing. As shown in FIG. 5, a mismatch between a shape of a representation 12 of a catheter 210, which may be generated using a kinematics model, and a shape of an image 14 of the catheter 210, which may be generated using fluoroscopy, is displayed 10. Embodiments of an optical fiber sensor 215 are coupled to or integral with a catheter 120 and address or prevent these types of mismatches by providing accurate catheter 210 shape data, thereby allowing for accurate manipulation and positioning of the distal portion 211 of the catheter 210. Embodiments may also be utilized to provide accurate position data.

Figure 6:
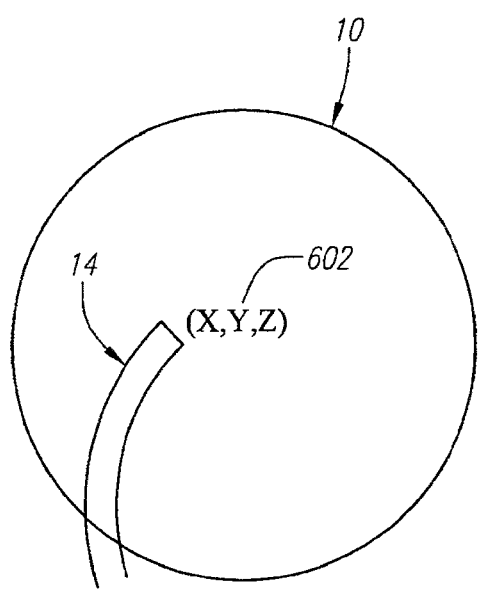
FIG. 6 generally depicts how optical fiber sensor embodiments may be utilized to provide a more accurate x-y-z position data of a two-dimensional image of a catheter.

For example, referring to FIG. 6, according to one embodiment, an optical fiber sensor 215 including one or more FBGs 302 as described previously is coupled to or integral with a catheter 210 and used as a localization sensing device to determine and display position of a given point upon an instrument 210 on a display 350. In the illustrated embodiment, a two-dimensional image 14 is generated using fluoroscopy and displayed 350. The image 14 may be shown independently (as shown in FIG. 6), or together with other representations and/or images. In one embodiment, the image 14 is displayed together with the virtual catheter representation 12 or "cartoon object" that is generated according to a kinematics model (as described with reference to FIG. 1).

As shown in FIG. 6, embodiments are used as a localization sensing device to generate three-dimensional position data or spatial coordinates (x-y-z) 602 of a given point on the catheter 210. In this manner, the image 14 is presented with more accurate x-y data, and z data is also generated such that a location of the catheter 210 or distal portion 211 thereof can be accurately determined or extracted from the optical fiber sensor 215 data. In this manner, a user or surgeon can know precisely where the distal portion 211 or tip of the catheter 210 relative to surrounding tissue.

Figure 7:
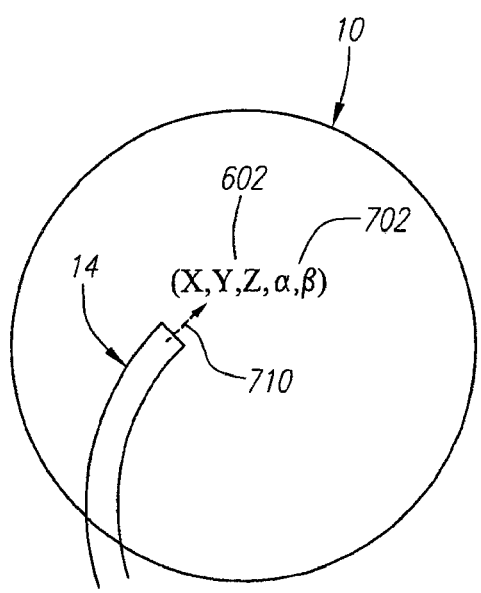
FIG. 7 generally depicts how optical fiber sensor embodiments may be utilized to provide more accurate x-y-z position data and orientation, roll or twist data of a two-dimensional image of a catheter.

Referring to FIG. 7, in another embodiment, in addition to the accurate x-y-z data 602. (as described with reference to FIG. 6), orientation, roll or "twist" angle data ($\alpha$, $\beta$) 702 may also be determined or extracted from the optical fiber sensor 215. In this manner, embodiments may be used to provide position (x, y, z) 602 and orientation ($\alpha,\beta$) data 702, which may be particularly beneficial when the distal tip of the instrument 210 is at or adjacent to a target area or tissue.

Figure 8:
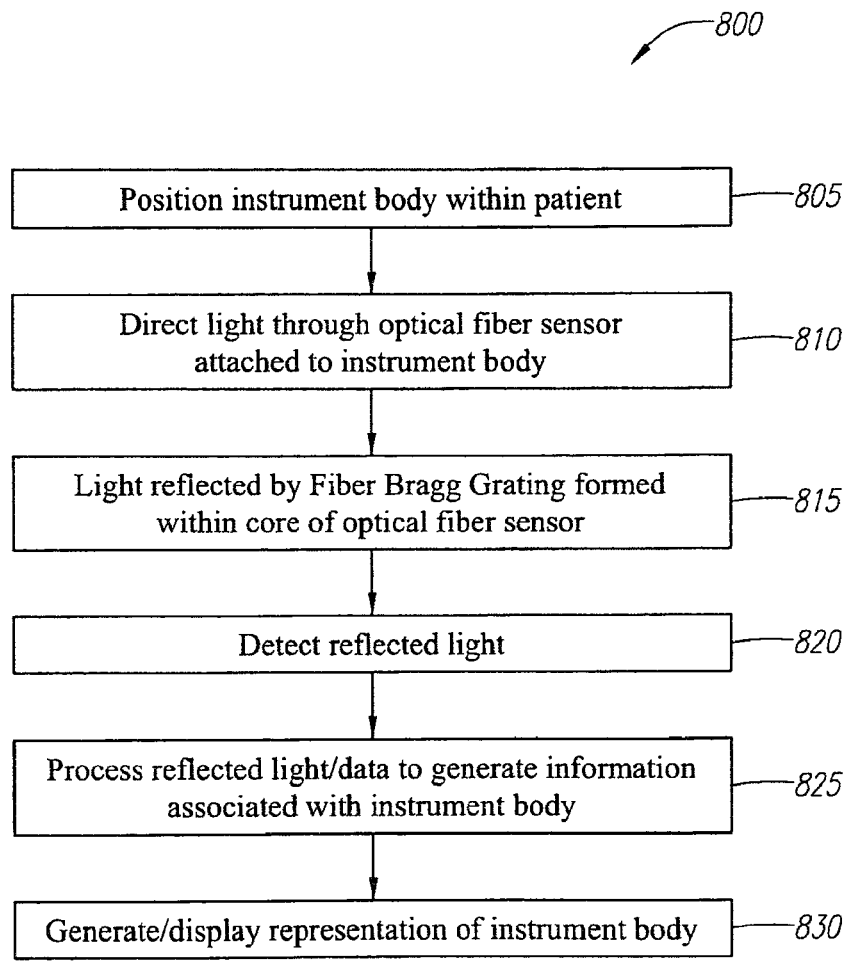
FIG. 8 is a flow chart of a method of generating and displaying a representation of an instrument body according to one embodiment.

Thus, referring to FIG. 8, one embodiment is directed to a method 800 of generating and displaying a representation of an instrument body 210 and includes positioning the instrument body 210 within the patient at stage 805, and directing light 322 through an optical fiber sensor 215 attached thereto or integral therewith at stage 810. At stage 815, light 326 is reflected by, e.g., a FBG 302, that is formed within a core 304 of the optical fiber sensor 215. At stage 820, reflected light 326 is sensed or detected by a detector 330, which may, for example, be a part of or operably coupled to a controller or output unit 300. At stage 825, a controller 340 or other suitable control element operably coupled to the detector 330 or read out unit 800 is configured to process data associated with the reflected light 326 to generate data such as spatial position and/or orientation data.

At stage 830, an image 14 and/or other representation 12 of the instrument body 210 is generated and displayed 350. The shape and/or position of the instrument 210 is accurately depicted in, for example, an image 14, based on data determined or derived from the light reflected 326 by FBGs 302 of the optical fiber sensor 215. Embodiments may also be utilized for other methods and may involve generating of an image 14 and another representation 12.

Given the number of points along a given instrument 210 that may be sensed with a Bragg grating fiber 215, embodiments advantageously allow for accurate sensing of the shape and/or position of the instrument 210. Shape recognition algorithms, which may be configured to detect the position of radioopaque markers positioned upon the elongate instrument 210, for example, may also be utilized to detect the position of the instrument 210 in space automatically. In the event of a mismatch between the Bragg grating fiber 215 based cartoon object 12 and the fluoroscopic images 14 (e.g., depending on the accuracy of the Bragg gating fiber 215 positioned along the elongate instrument 210 and the accuracy of shape recognition, or marker recognition algorithms), a procedure may be interpreted. For example, a robotic drive motor may be deactivated automatically, or subsequent to a notification (audible, visual, etc.) to the operator that a mismatch exists.

The position and/or orientation of other components may also be displayed, and they may be displayed 350 together with a representation 12 generated according to a kinematic model (as discussed above) and/or with other representations or images, e.g., together with an indicator of an orientation of an image capture device, such as an actual or virtual camera, ultrasound image capture device, optical or infrared imaging chip, etc. In the illustrated embodiment, the orientation of an image capture device is represented as an arrow object 710. The arrow object 710 indicates the origin position and vector of the orientation of the image capture device relative to other objects presented upon the same display in two or three dimensions. In other embodiments, the display element depicting roll can be a display of roll angle, or another arrow, a horizon indicator, etc. Thus, it should be understood that additional "cartoon" objects or representations showing the position and/or orientation of different types of system components can be displayed together with the representation 510 of an instrument 210 based upon localization information.

Further, other localization sensors can be used to determine the shape, position and/or orientation of one or more points of an elongate instrument, such as a catheter 210, in space—and such points may be utilized to construct and display a cartoon or representation of such instrument 210 relative to other images of the same object, generated based upon fluoroscopy, other models, etc. For example, other localization sensors may be coupled to an instrument body such as a catheter 210 and/or coupled to a fiber 215. Thus, a catheter 210 may include an attached fiber 215 and localization sensor, or the localization sensor may be coupled to the fiber 215 instead. Suitable localization sensor, that may be used for this purpose include, for example, electromagnetic coils (such as those available from Biosense Webster or Ascension Technology), potential difference sensing devices (such as those available from St. Jude Medical), and ultrasound sensors. Further aspects of such devices are described in further detail in U.S. application Ser. No. 11/637,951, the contents of which were previously incorporated by reference.

Thus, embodiments of optical fiber sensors 215 can be used to "localize" or monitor the positions and/or orientations of various objects or system components involved in a particular procedure. For example, not only is it useful to localize instruments, e.g., a catheter 210, configured and utilized for endocorporeal use in a given procedure, but also it is useful to localize other associated objects and components, such as structures utilized to present the operational instruments 210 into the body, structures utilized to stabilize the body, the body itself or portions thereof. Further, depending upon the capabilities (for example bus and processing capabilities; certain localization systems are only capable of sensing a small number of sensors in parallel; Bragg Grating sensors 215, on the other hand, may be utilized, to gather at least positional information regarding many points along a given structure or multiple structures, depending upon the particular signal processing configuration) of the localization system utilized, multiple mechanically-associated objects may be localized simultaneously. For example, the instrument 200 shown in FIG. 2A includes three coaxially associated instruments—an outer sheath catheter 220, an inner coaxially-associated catheter 210 such as a guide catheter, and a working instrument 240 such as a guidewire, a pusher wire, an ablation catheter, a laser ablation fiber, a grasper, a collapsible basket tool, etc., which is positioned within the working lumen defined by the inner catheter 210, and all of which may be localized simultaneously with embodiments for maximum operator feedback and system control.

An instrument or component of a robotic surgical system having an optical fiber sensor 215 can also be used in other methods, and with external structures, such as instrument driver structures, proximal instrument block structures, instrument driver setup structures, fluoroscopy gun and/or arm structures, etc. With embodiments, these other system components may also be localized and monitored.

Optical fiber sensors 215 can also be coupled or attached to a patient, e.g., to a patient's chest. With this configuration, the position of the patient's chest may be localized to provide the system and operator with the ability to understand changes in position and, for example, gate or pause activities during deep breaths or body movements, simply warn the operator with visual, audible, and/or haptic feedback, or facilitate recalibration of relative positioning between instruments and the patient, for example. Such techniques may be utilized to present an operator with pertinent information regarding the position and/or orientation of one or multiple instruments.

For example, it may be useful to present such information for two or more robotic arms or robotic catheters being utilized in a given operational theatre. Further, it may be useful to present such information for one or more imaging device, such as an ultrasound catheter. Further, such techniques are highly useful in not only electromechanically-driven instrument scenarios, such as with robotic arms or robotic catheters, but also in manually-actuated instrument scenarios, where handles and other components are utilized to operate instruments.

Figure 9:
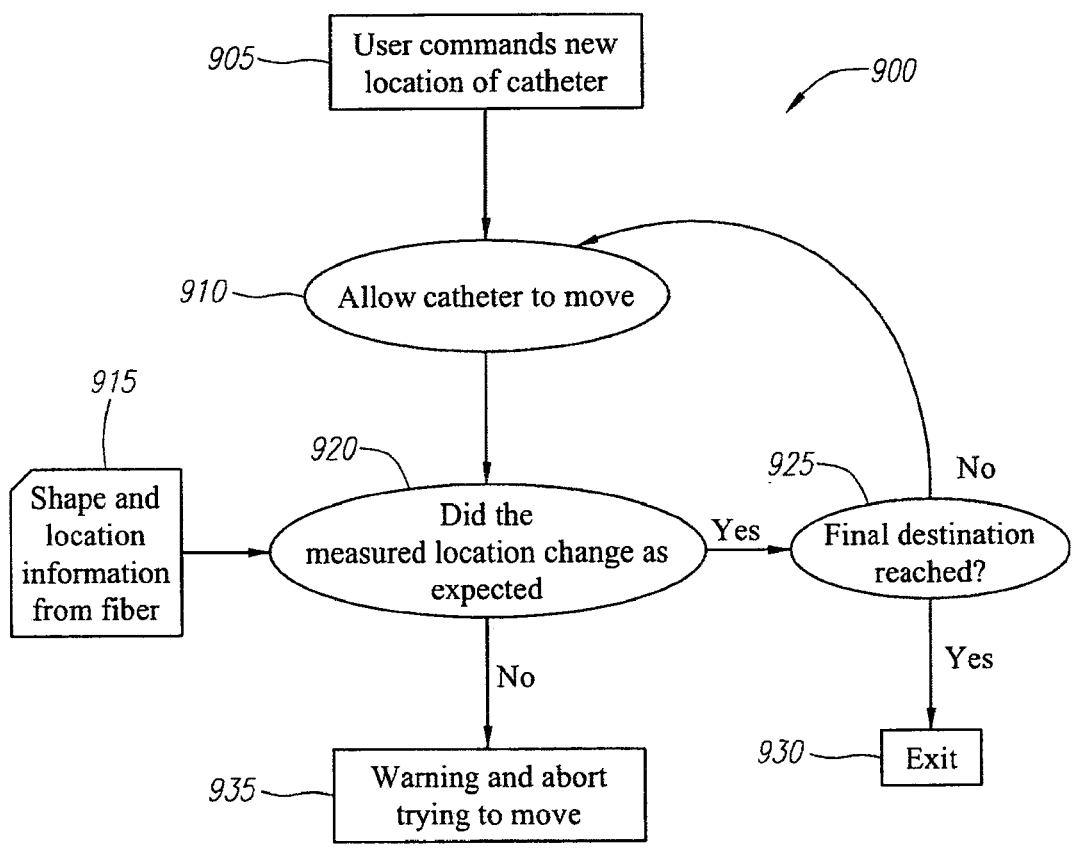
FIG. 9 is a flow chart of a method of controlling movement of a component of a robotic surgical system based on shape and location information received or derived from light reflected by an optical fiber sensor according to another embodiment.

Referring to FIG. 9, another embodiment is directed to a method 900 of controlling an instrument or elongate body, such as the catheter 210, based on the shape and/or orientation of the catheter 210 that is expected versus the shape and/or orientation actually achieved or measured using an optical fiber sensor 215. The method 900 includes receiving a user command associated with a new or desired location of the catheter 210 at stage 905, and allowing the catheter 210 to move at stage 910 according to the command issued or received at stage 905. At stage 915, a determination is made whether the measured location of the catheter 210 changed as expected based on the shape and location information received from the optical fiber sensor 215 coupled thereto or integrated therein at stage 920. If so, then at stage 925, a further determination is made whether the catheter 210 has reached or is positioned at the commanded or final destination, position or orientation. If so, the method is successful and complete at stage 930. Otherwise, the catheter 210 can be moved further at stage 915 and method steps can be repeated as necessary until the final destination has been reached. However, movement of the catheter 210 may also result in stage 920 resulting in a determination that the measured location changed in an unexpected way, in which case a warning may be issued and/or catheter 210 movement can be limited or aborted at stage 935.

Figure 10:
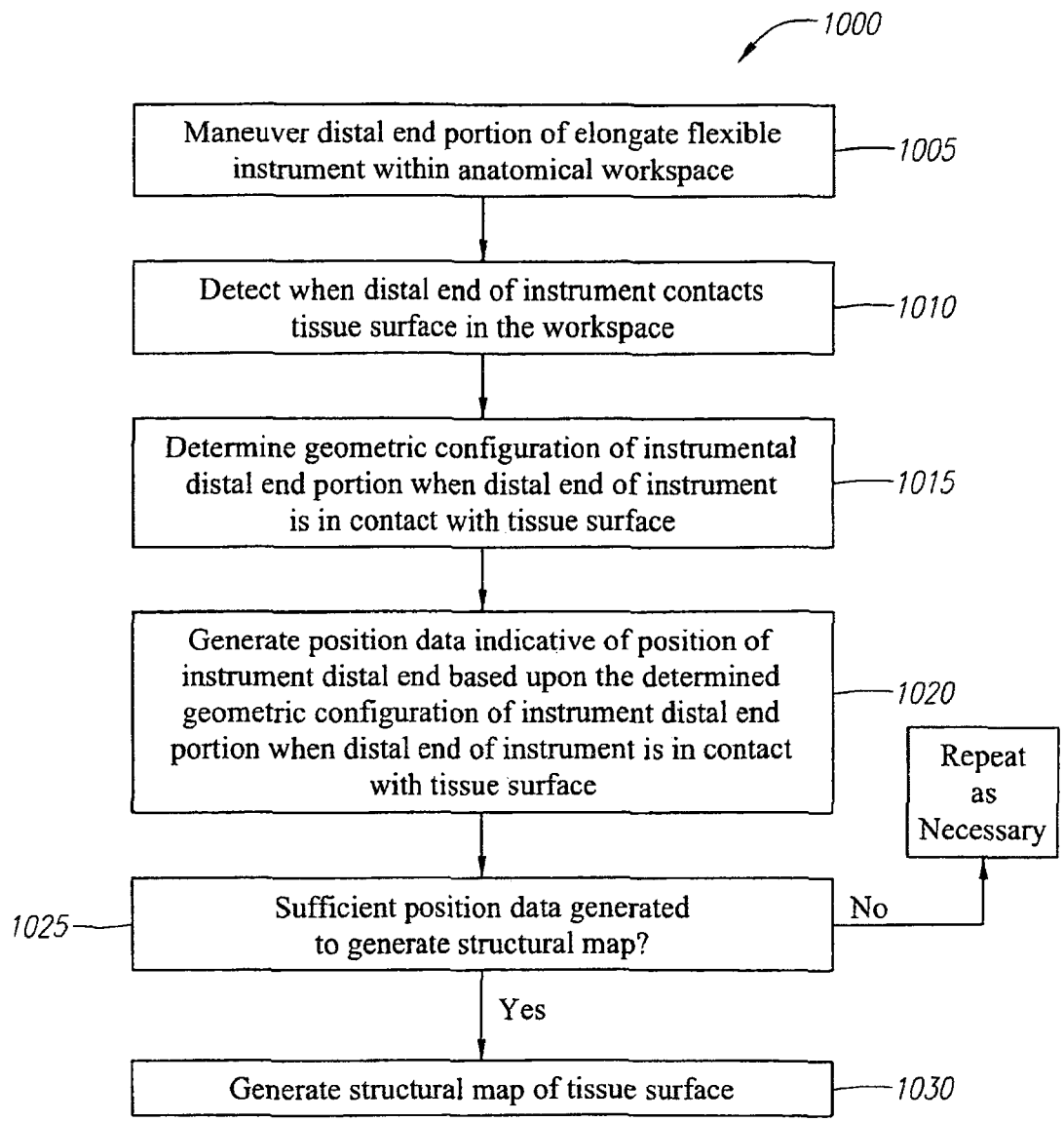
FIG. 10 is a flow chart of a method of generating a structural map of a tissue surface utilizing an optical fiber sensor according to another embodiment.

Referring to FIG. 10, other embodiments are directed to a method 1000 of generating a structural map of an internal body tissue, such as endocardial tissue. The method includes maneuvering a distal end portion 211 of an elongate flexible instrument or catheter 210, which includes an optical fiber sensor 215, within an anatomical workspace in a body at stage 1005, and detecting when a distal end 211 of the instrument 210 contacts a tissue surface in the workspace at stage 1010. At stage 1015, a geometric configuration of the distal end portion 211 of the instrument 210 is determined when the distal end 211 contacts the tissue surface, e.g., based on light reflected 226 by one or more FBGs 302. At stage 1020, position data is generated and indicative of a position of the instrument distal end portion 211 based upon the determined geometric configuration of the instrument distal end portion 211 when the distal end portion 211 of the instrument 210 contacts the tissue surface. At stage 1025, one or more or all of the previous stages can be repeated as necessary in order to generate sufficient position data to generate a structural map of the tissue surface.

Figure 11:
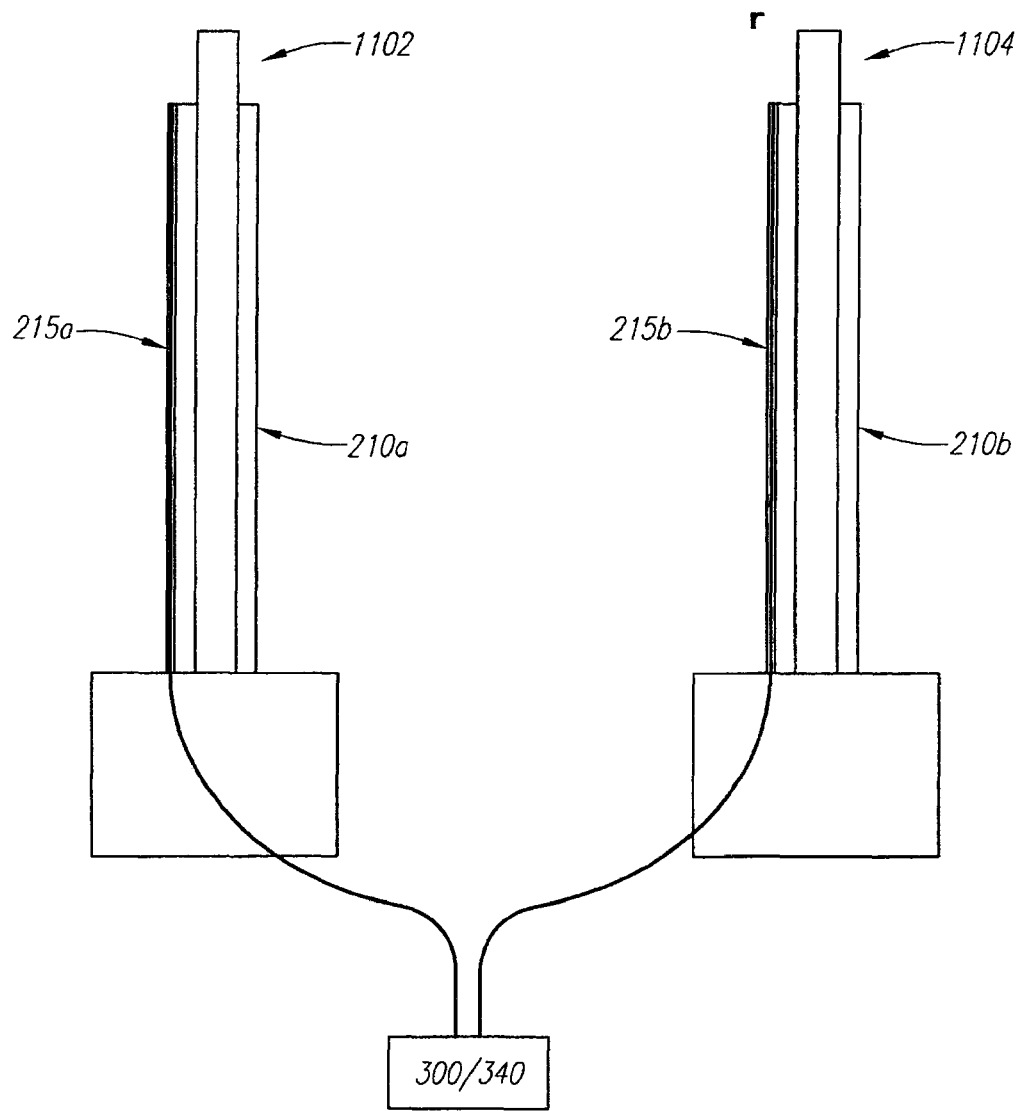
FIG. 11 illustrates an embodiment in which multiple fibers are coupled to or integral with respective robotically controllable catheters that carry different types of catheters.

Referring to FIG. 11, in another embodiment, multiple robotically controlled catheter instruments 210a,b may have respective optical fiber sensors 215a,b coupled thereto (e.g., extending through a lumen 213 or 217). In the illustrated embodiment, one robotically controllable catheter 210a has an optical fiber sensor 215a coupled thereto and carries or supports an imaging device or imaging catheter 1102. Another robotically controllable catheter 210b includes an optical fiber sensor 215b and carries or supports a mapping catheter 1104, which is used to map electrical signals within the heart 330. With this configuration, embodiments advantageously allow the shape and location of multiple catheters 210a,b that are used for different purposes to be determined by use of light reflected by FBGs 302 of respective optical fiber sensors 215a,b.

Figure 12:
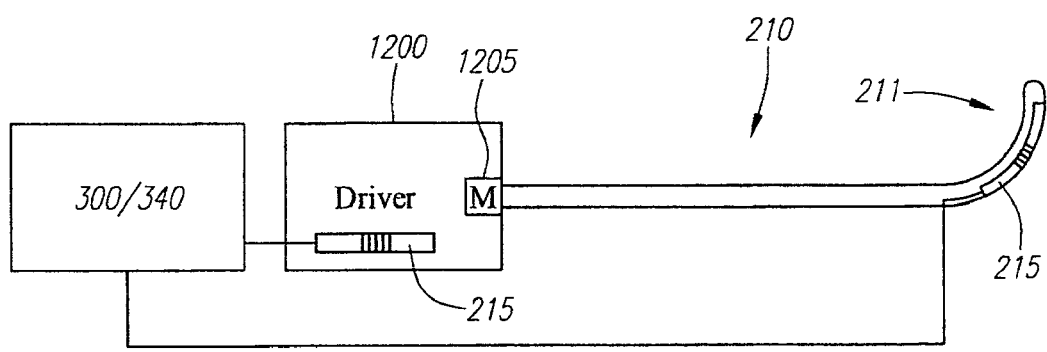
FIG. 12 illustrates another embodiment of a system in which an optical fiber sensor is coupled to or integral with a controller or instrument driver of an elongate instrument.

Yet other embodiments are directed to methods involving system components other than elongate instruments or catheters. For example, referring to FIG. 12, other systems and associated methods may involve determining one or more position and/or orientation variables of an instrument driver 1200 that includes one or more motors 1205 that can be actuated to controllably manipulate a bendable distal end portion 211 of an elongate instrument or catheter 210 (which may also have an optical fiber sensor 215 coupled thereto as illustrated) based on detected reflected light signals 326 received from the respective FBGs 302 on the optical fibers 215. FIG. 12 generally illustrates an output or readout unit/controller 300/340 for ease of illustration, but may include components such as a light source, detector, etc., as discussed with reference to FIG. 3A and FIGS. 22A-C.

Figure 13:
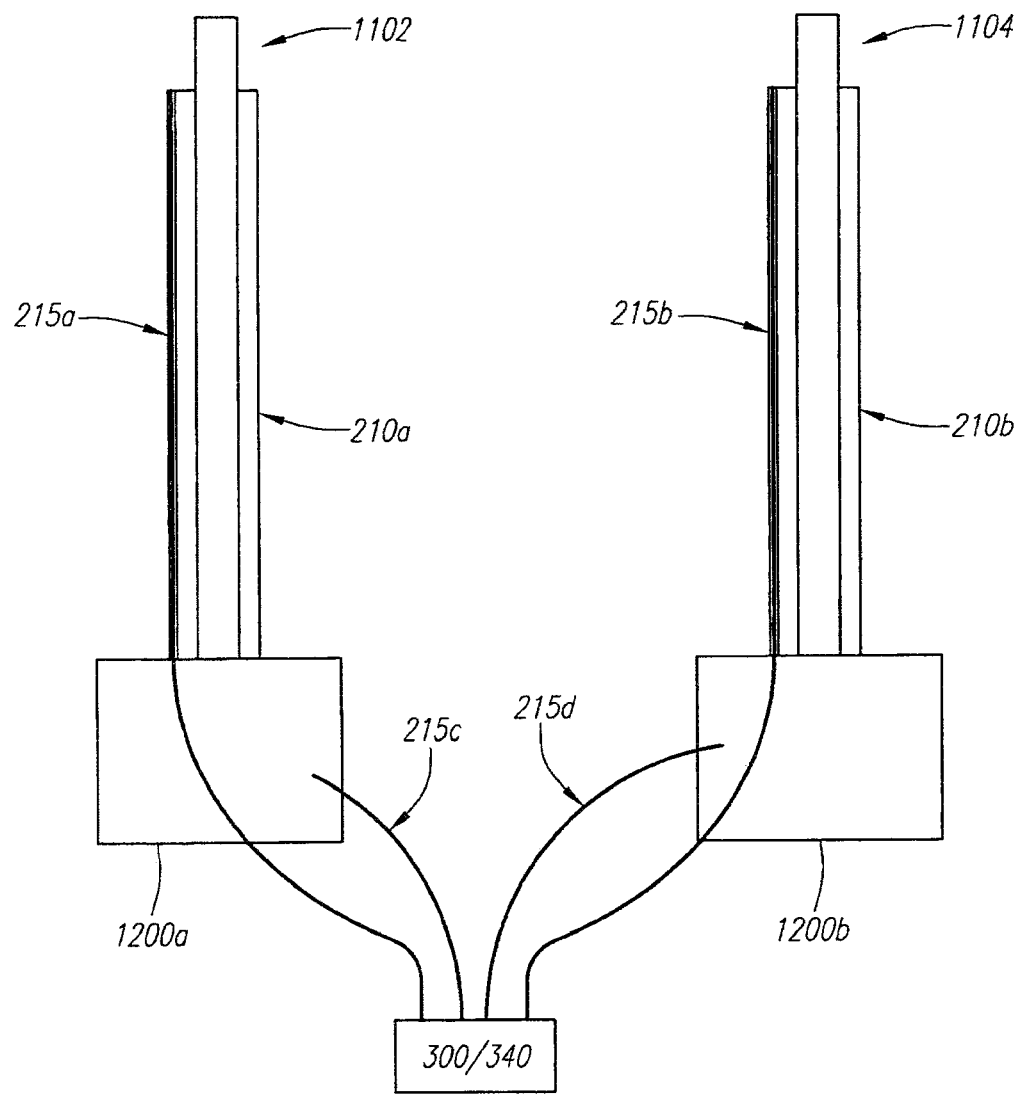
FIG. 13 illustrates an embodiment in which optical fiber sensors are coupled to or integral with respective controllers or instrument drivers of respective robotically controllable catheters and coupled to or integral with respective controllable catheters.
Figure 14:
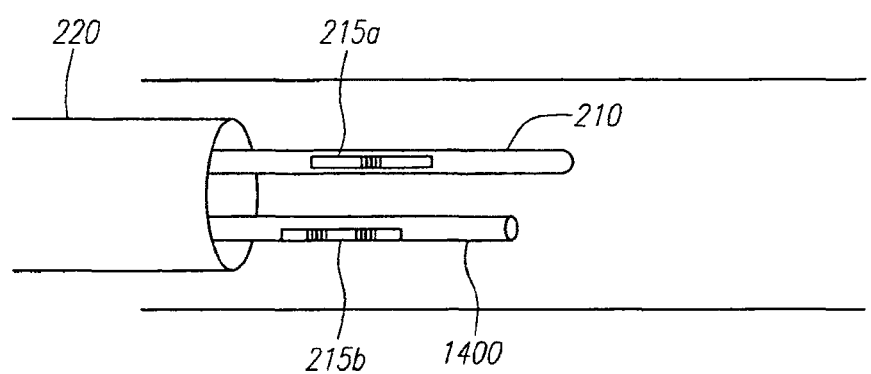
FIG. 14 illustrates another embodiment in which optical fiber sensors are coupled to or integral with elongate instrument bodies such as a catheter and an image capture device.

Referring to FIG. 13, in a further embodiment, optical fiber sensors 215a,b are coupled to respective robotically controlled catheter instruments 210a,b, which may carry or support other devices or catheters such as an imaging device or imaging catheter 1102 and mapping catheter as discussed with reference to FIG. 11. Additionally, in the illustrated embodiment, additional optical fiber sensors 215c,d are coupled to controllers, arms or instrument drivers 1200a,b that are used to control or manipulate the respective catheters 210a,b. The arms, instrument drivers or controllers 1200a,b are typically located outside of the patient's body and, in one embodiment, the fiber sensors 215 are larger than the fiber sensors 215 that are coupled to catheters or elongate instruments 210a,b and advanced into the patient's body. For example, fibers 215c,d that are located outside of a patient can have a diameter of greater than 200 microns, e.g. about 500 microns, whereas fibers 215a,b for use within a patient may have a diameter of about 150 microns. With this configuration, larger diameter fibers 215c,d can then have the individual cores spread further apart Which, may be utilized to increase the accuracy of the measurements by increasing the difference in signal produced by cross-sectionally opposing fibers. The larger diameter fibers 215c,d can accurately measure the location of the arm or driver 1200a,b, and the smaller diameter fibers 215a,b can measure from a point where the larger diameter fiber 215c,d ends.

in another embodiment, referring to FIG. 14, other systems and associated methods are directed to determining one or more position and/or orientation variables of an image capture device 1400 based on light reflected 226 by Bragg gratings 302 on a Bragg sensor optical fibers 215b coupled to or integral with the image capture device 1400. Examples of image capture devices 1400 include a fluoroscope, an optical camera, an infrared camera, an ultrasound imager, a magnetic resonance imager, and a computer tomography imager. In the illustrated embodiment, the catheter 210 and the image capture device 1400 are advanced through an outer Sheath 220 and include respective optical fiber sensors 215a,b, but other system configurations may be utilized. A controller 340 may be configured to determine one or more position and/or orientation variables of the image capture device 1400 based on signals 326 received from Bragg gratings 302 on a fiber 215.

Figure 15:
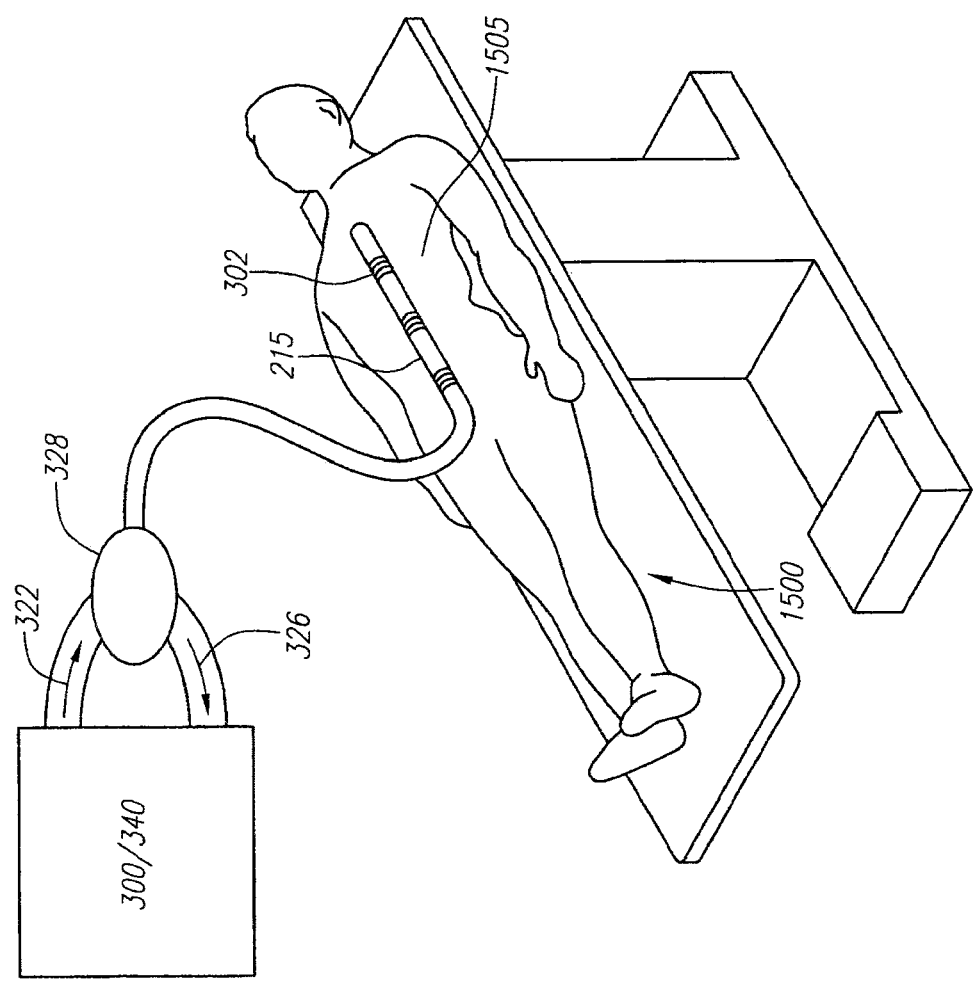
FIG. 15 illustrates another embodiment of a system in which an optical fiber sensor is attached or affixed to a patient.

Referring to FIG. 15, other methods and systems are directed to an optical fiber sensor 215 that is attached to a patient's body 1500, e.g. the chest 1505 of a patient 1500, using a patch or other suitable adhesive. For example, a fiber sensor 215 may be coupled to the patch that is applied to a patient 1502. Such embodiments are useful for determining one or more position and/or orientation variables of the patient's body 1500 to which an optical fiber sensor 215 is attached based on signals reflected 226 by one or more Bragg gratings 302.

This configuration allows for detection of an unexpected movement of a patient 1500 based on signals received from the respective FBGs 302, in response to which an output can be generated for the system operator to allow the system operator to adjust the catheter 210 within the patient 1500 as necessary, temporarily suspend the procedure, or halt the procedure. Further, such embodiments area also useful for generating an image of the patient 1500 or such that an image of a patient's body 1500 that is displayed can be moved or adjusted according to the movement sensed using the optical fiber sensor 215. Other methods may involve coordinating diagnostic and/or therapeutic procedures on the patient with the patient's respiration as determined by light reflected 226 by one or more FBGs 302.

More particularly, as described above, it is desirable to know where the patient 1500 and the anatomy are located in relation to the catheters or elongate instruments 210. For example, if the patient 1500 unexpectedly moves, a warning may be generated to reposition the catheter 210 or other components. Thus an automatic, semi-automatic or a manual feedback loop may be created based on the position of the patient 1500. Embodiments provide for using a shape and location measurement fiber 215 for patient 1500 monitoring. A key advantage of embodiments is that a single technology (in this example a Bragg-grating fiber 215) may be used for locating all the essential components of the environment, although other localization technologies, such as electromagnetic and potential-difference based localization technologies, may also be used, depending upon the capabilities of the particular system employed.

When navigating, or "driving", in static image-based (preoperative or intraoperative) models, such as those created utilizing modalities such as MRI and/or CT, it is advantageous to register the model to the distal tip 211 of the elongate instrument 210; after such registration has been accomplished, if the patient 1500 moves, the registration relationship may be significantly altered, requiring another registration unless embodiments as illustrated in FIG. 15 are utilized. With embodiments, a patient localization device Which in one embodiment is an optical fiber sensor 215 is used to understand the relative geometric/spatial relationships of the instrument 210 components and patient 1500 in real, or near-real, time, in which scenario registration may be updated manually or automatically.

There are several ways to attach the optical fiber sensor 215 to the human body 1500. One method involves wrapping fiber sensor 215 around the chest 1505 of the patient 1500. As discussed above, another technique is to attach the fiber sensor 215 to a patient patch, and applying the patient patch to the chest 1505 of the patient 1500. As the fiber sensors 215 are very thin, the images of the fibers 215 viewed via an image capture device 1400 such as a fluoroscope generally are not objectionable. Further, the fiber sensor 215 may be attached to a radio-opaque marker (not illustrated in FIG. 15) such that it is possible to see the markers and associated fiber sensor 215 clearly in a fluoroscopic image. As the exact location of the marker can also be determined by the location measurement system of the fiber sensor 215, the location of the marker can thus be known in two coordinate systems—the coordinate system of the fluoroscopic imaging system 1400 and the coordinate system of the shape and location measurement fiber sensor 215. This permits a way to spatially associate the coordinate system of the fiber sensor 215 with the coordinate system of the imaging system 1400.

More particularly, in one embodiment, referring again to FIG. 14, a shape and location measurement fiber 215 is coupled to an external imaging device 1400 such as a fluoroscope. The knowledge of the location of the fluoroscope 1400 is advantageous for the combination display of the fluoroscopic image and the virtual catheters and for aligning the coordinate systems of the imaging system 1400, the fiber sensor 215 based device and the robot or other control mechanism 1200. This is particularly true in the embodiment wherein one has a fluoroscopy display driving to be instructive to the operator.

Patient 1500 respiration may also be monitored with the fiber 215 based measurement system. As the patient's chest 1505 moves with breathing, the optical fiber sensor 215 attached thereto also moves. These movements can be monitored, and this information can then be fed back into the robotic navigation system and may be used, for example, to accurately deliver therapy. Elaborating on this example, in the situation in which the catheter 210 holds or supports an ablation catheter, ablation energy can be delivered at the same point in the respiratory cycle or the respiratory and cardiac cycle. This may improve the accuracy and effectiveness of ablations.

Monitoring patient 1500 respiration and movement can lead to yet another advantage. In many electrophysiology procedures, models of the inside of the heart 230 are built by various methods. These models are quite distinct from images as a model is a parametric representation of the heart 230. These models are often stationary in that they do not contain any information about the dynamics of the heart 230 or the dynamics of the patient 1500 such as due to respiration. These models are used for navigation purposes for example to navigate a catheter 210 inside of the heart 320. The availability of patient 1500 movement data (such as via respiration) though the use of a fiber sensor 215 or other localization technique, advantageously enables compensation or adjustment of the model.

Embodiments can also be utilized for purposes of registration, or for spatial association of objects and/or images. Such registration may be continuous or semi-continuous, based on a common reference or connected by a defined relationship. References may also be connected by a defined relationship or associated utilizing other imaging modalities.

As discussed above, in known minimally invasive procedures, an elongate instrument 120 may be inserted within the body and an imaging device such as a fluoroscopic system may be utilized to image, or "visualize", the elongate instrument 120 or a portion thereof, but a drawback of known fluoroscopic imaging systems is that they are projection based—the depth information is lost and therefore true three-dimensional location of objects such as an elongate instrument in the field of view of the fluoroscope is lost. However, with embodiments, an elongate instrument 210 has a shape and location measuring fiber or optical fiber sensor 215 that provides the three-dimensional location of specific locations in a continuous or semi-continuous manner, thus allowing for automatic registration. Locations of interest may be visualized with the fluoroscope and spatially analyzed utilizing techniques such as pattern, geometry, shape, movement, and/or marker recognition (preferably with the help of radioopaque markers positioned upon portions of the subject instrument, beacon transducers placed upon the instrument for ultrasound pinging localization, or other techniques to localize with fluoroscopy); such results then may be processed in conjunction with the location information obtained about these same locations from the fiber sensor 215 based measurement device. Image information from the two techniques may be utilized to make the images produced by each appropriately and accurately associated with the other in three-dimensional space.

A Bragg grating fiber sensor 215 based shape and localization measuring device may be attached to one or more or all of the key elements in an operating room environment including, for example, a catheter 210 or other elongate instrument, to controllers or instrument drivers 1200 that control the location of the catheter 210, to the bed supporting the patient 1500, to the patient 1500, and to an image capture device 1400 such as an external imaging system, one example of which is a fluoroscopic system. It is advantageous if all of the fiber sensors 215 in this embodiment have a single common reference point or reference coordinate system, preferably located as distally as possible without compromising the mechanical behavior of the system (to increase the effectiveness of common-mode error rejection analysis, which may be applied to light or data moving through the system of localization fibers 215). This ensures that the coordinate system for the devices and instruments and objects to which the fiber 215 based system is coupled are all similarly and precisely spatially associated during registration.

Each fiber 215 may have its own reference point, and each reference point may refer to a single coordinate system for coordination. Different instruments may each have a fiber 215, and in this case, and the relationship between different instruments can be determined based on a fixed spatial relationship between instruments, or if there is not a fixed spatial relationship, then each fiber on each instrument may refer to the same coordinate system, and data from the fibers can be used for an necessary adjustments. Thus, with embodiments, the position and/or orientation variables of a plurality of elongate instruments, each of which includes an elongate instrument body having a Bragg sensor optical fiber 215 coupled thereto, may be determined and registered in a single reference coordinate system. The instrument bodies may be coupled to a same or different structure in a known spatial relationship, or coupled to a same or different structure in an unknown spatial relationship. In the latter case, registration of the instrument position and/or orientation variables of respective instruments in as single reference coordinate system is accomplished by maintaining a fixed distance between respective locations on the instrument bodies.

Even if the references for all of the fiber sensors 215 are not the same, in one embodiment there is a defined relationship between the different references such that the relationship between the different coordinate systems is accurately defined and may be utilized to analyze the spatial relationships between coordinate systems. For example, two references may be utilized for two fibers 215 attached to two devices, with the two references connected by a stiff structural rod or member (or another device that prevents relative movement between the reference points, or with other devices to predictably understand the geometric/spatial relationship between the two references) to prevent relative motion between the references.

Other technologies such as an electromagnetic or potential-difference-based localization, lasers or ultrasound (for beaconing, shape/marker/pattern/etc. recognition, and/or time-of-flight analysis to determine relative spatial positioning) may be used to establish the absolute positions of each reference. For example, an electromagnetic localization sensor may be placed on each Bragg fiber 215 to obtain the three-dimensional coordinates relative to a coordinate system established by the electromagnetic localization system. The measurements s provided by each fiber 215 all are consistent with each other as they all are referenced back to a common reference.

Embodiments may also be utilized in procedures for calibration instruments and tools in which the instrument or tool includes an optical fiber sensor 215. While certain techniques for calibration are known, embodiments provide apparatus and methods for calibrating a robotically controlled elongate instrument attached to one or more shape and location measuring fibers 215.

Initial calibration information can be obtained utilizing several techniques. In one method, measurement or observation of properties and/or behaviors of the instrument having an optical fiber sensor 215 and being calibrated are observed. Other methods involve obtaining information from the design of the localization/shape-sensing fiber 215, the elongate instrument 210, or both. Yet other methods involve use of calibration or test fixtures adapted for an instrument that includes an optical fiber sensor 215.

Figure 16:
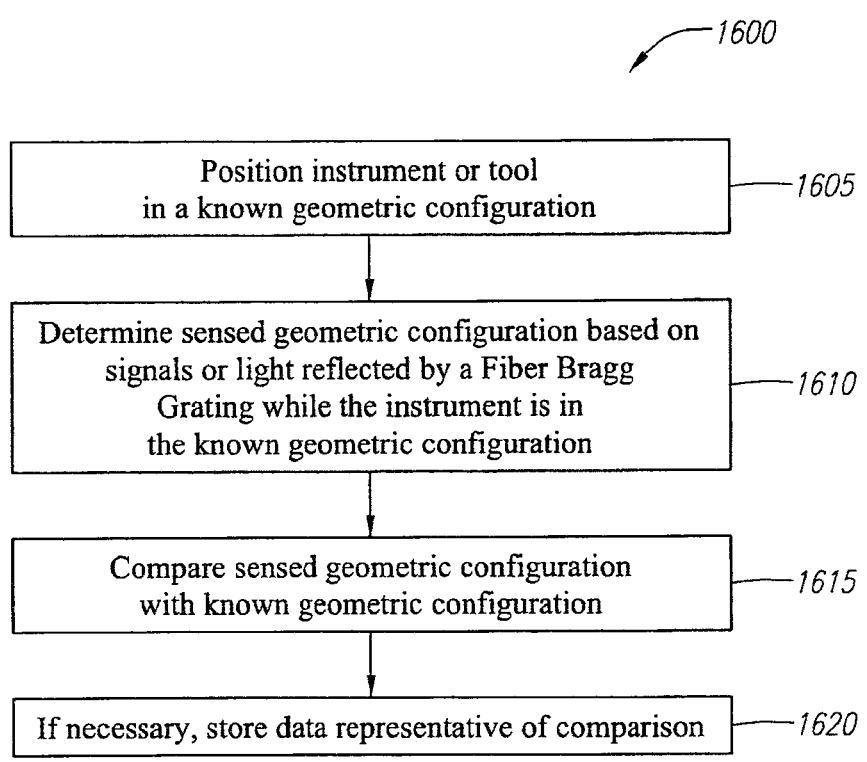
FIG. 16 is a flow chart of a method of performing a calibration procedure utilizing an optical fiber sensor according to one embodiment.

Referring to FIG. 16, a calibration procedure 1600 according to one embodiment includes positioning an instrument or tool in a known geometric configuration at stage 1605. At stage 1610, a sensed geometric configuration is determined based on signals or light 326 received from the one or more Bragg gratings 302 of a fiber sensor 215 while the instrument body 210 is in the known geometric configuration. At stage 1615, the sensed geometric configuration is compared with the known geometric configuration. At stage 1620, if necessary, data representative of the comparison is stored on a storage medium associated with instrument 210. The storage medium may be, for example, a programmable device, a bar code, a "RFID" device, or a memory dongle, which may be positioned within or coupled to the elongate instrument 210, a software of a system component associated with the elongate instrument 210, or an external device such as an external server, in which case retrieval can be performed via a computer network. Thus, in one embodiment, calibration of an instrument 210 that has an optical fiber position sensor 215 includes performing a predetermined task with the instrument 210, acquiring measurements or recording relevant information, storing such information or derived information, and retrieving such information for use in normal operation.

Figure 17:
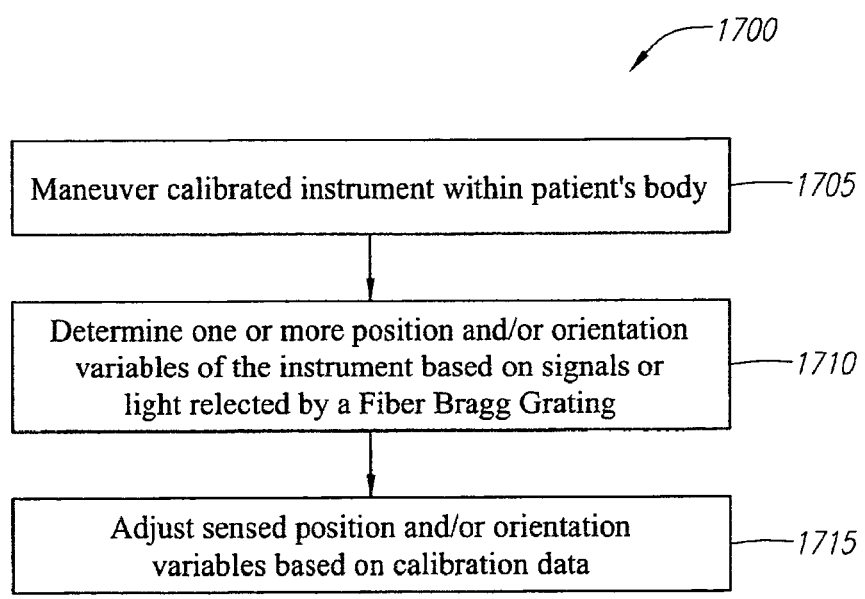
FIG. 17 is a flow chart of a method of performing a diagnostic or therapeutic procedure using an instrument calibrated as shown in FIG. 16.

Referring to FIG. 17, a diagnostic or therapeutic procedure 1700 may be performed using the instrument calibrated as shown in FIG. 16. At stage 1705, the instrument so calibrated is maneuvered within a patient's body. At stage 1710, one or more sensed position and/or orientation variables of the instrument are determined based on signals received from the one or more FBGs 302 while the instrument is in the patient's body. At stage 1715, the sensed position and/or orientation variables are adjusted based on calibration data, which may be stored in a storage medium.

The types of habilitation, that can be stored (for example, upon a memory chip associated with or coupled to the elongate instrument) as part of calibration include but are not limited to, a diameter of a fiber 215 or fiber core 304, a position of a core 304 within a fiber 215, a position of fibers 215 within or coupled to an elongate instrument 210 or other system component, a position of each FBG 302 formed within the core 304, a reflectivity of each FBG 302, thermal characteristics of the fiber 215, mechanical properties of the fiber 215 including stiffness, offsets and gain, and mechanical properties of the combination of the catheter 210 and fiber 215 coupled thereto, such as stiffness and position or orientation dependent properties. Calibration information can be stored in various places and devices including but not limited to, a programmable device within or coupled to the elongate instrument 210, software of a system component associated with the elongate instrument 210, an external device such as an external server in which case retrieval can be via a computer network, a bar code, a "RFID" device, or a memory dongle. p Initial calibration information for use in embodiments can be obtained utilizing several methods. In one embodiment, calibration of an elongate instrument 210 that includes an optical fiber position sensor 215 coupled to a distal portion or tip 211 thereof involves driving the elongate instrument 210 to a known position in a well-defined and characterized geometric fixture or test structure. The operator then compares the reading from the sensor 215 to the known position. The reading can thus be equated to the known position.

Figure 18:
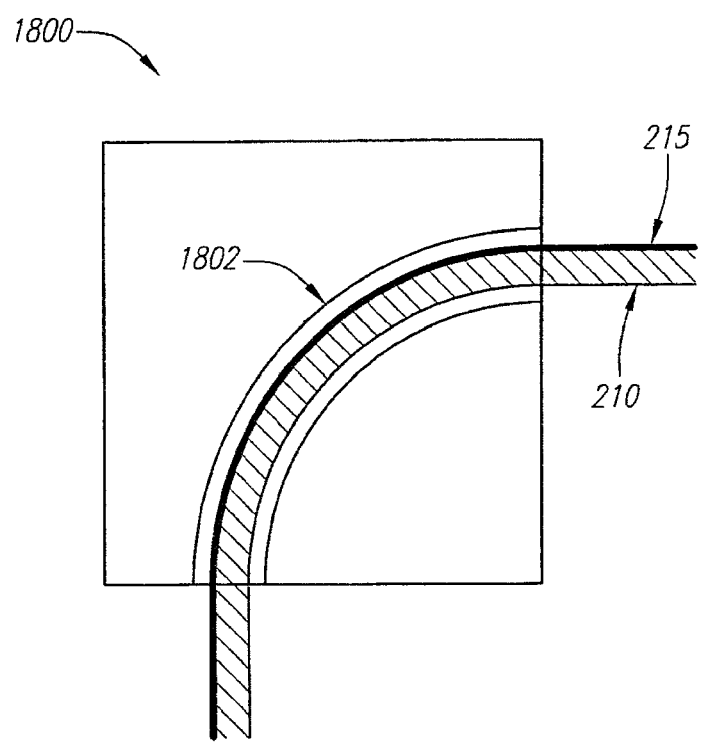
FIG. 18 illustrates one embodiment of a test fixture suitable for calibration procedures involving an optical fiber sensor.

FIG. 18 illustrates one embodiment of a test fixture 1800 and associated method that may be used during calibration procedures. In the illustrated embodiment, the test fixture 1800 is made from a rigid material such as glass, plastic or another material in which a calibration groove 1802 can be formed. In the illustrated embodiment, the groove 1802 spans a quarter of a circle or has a bend of about 90 degrees. The groove 1802 is configured to accommodate a catheter 210 and an optical fiber sensor 215 coupled thereto or integral therewith to ensure that the combination of the catheter 210 and optical fiber sensor 215 can both bend with the groove 1802, e.g., at about 90 degrees. The measurements from the fiber 215 may be read for this section and any error may be calibrated out.

In another embodiment, the rigid structure 1800 may define a linear or straight groove rather than a groove 1802 at about a 90 degree bend as illustrated in FIG. 18. With this configuration, similar to the embodiment described above, the linear groove is configured to accommodate the catheter 210 and the optical fiber sensor 215. During use, the combination of the catheter 210 and fiber sensor 215 is positioned within the linear groove, and readings from each FBG 302 are obtained using a detector or fiber readout unit 330. This establishes a "zero" reading for the combination of the catheter 210 and the optical fiber sensor 215 and corresponds to a linear or straight shape. Any other shape will be measured relative to a zero shape.

However, a zero shape does not have to be a straight shape. A zero shape could be any predefined arbitrary shape. A non-straight zero shape may be desirable if, for example, a fiber is integrated to a pre-bent catheter 210 (i.e., the natural shape or the "home" shape of the catheter is not straight but bent).

Thus, a calibration process may involve placing the catheter 210 and localization/Shape-sensing fiber 215 in a well-defined rigid structure 1800 with a groove, sending light 322 (or other appropriate energy) through the fiber 215, detecting light 226 reflected by one or more FBGs 302 within the fiber core 304, obtaining strain values and calculating shape, storing the strain values or some derived values in a storage device identifying this as a "zero" shape.

Calibration procedures and related data can be based on each individual device or a group of devices. For example, if it is known that a certain group of elongate instruments 210 or fibers 215 has a certain type of property that effected the measurements in certain ways, this information can become part of the calibration information. From group to group, this information may be different. When the catheter 210 is installed, the system can read the serial number of the catheter 210 or some other form of identification and the correct calibration values can be utilized.

Embodiments may also be utilized in force calculation and feedback applications. Various techniques may be utilized to calculate force at the distal tip of the catheter 210 or other instrument. One such method is described in U.S. patent application Ser. No. 11/678,016, "Method of Sensing Forces on a Working Instrument", filed Feb. 22, 2007, previously incorporated by reference herein. A force applied upon an instrument may be calculated by understanding the shape of the instrument with a load applied and utilizing kinematic relationships of the instrument to back out the presumed load applied to the instrument. The calculated load may then be utilized for force feedback to the operator techniques, such as haptics, on-screen displays, warnings to the operator, etc. For example, in one embodiment, if the force exceeds a certain value, then a warning message may be displayed or other actions may be taken to prevent patient injury; yet another alternative to this scheme is that the level when warnings or other actions are initiated may be anatomy specific; for example, in the ventricles where the walls are thicker, higher forces may be applied without triggering an alarm or response.

As described in the incorporated references regarding fiber-based Bragg diffraction localization, the location measurement at the tip of the location measurement fiber 215 depends on component measurements obtained from each grating 302. In practice, each grating 302 will contribute a finite amount of error in measurement. The error at the tip is the sum of all errors, i.e., errors are cumulative. It is thus advantageous to maintain length from the tip to the origin, or the reference, or from where the measurement must be taken, as small as possible. However, the cores 304 of the optical fibers 215 may have numerous gratings 302, and the number of gratings 302 may be more than what is required between the tip and the origin. Thus, in one embodiment, it is not necessary to include all of the gratings 302 for location measurements at the tip.

Figure 19:
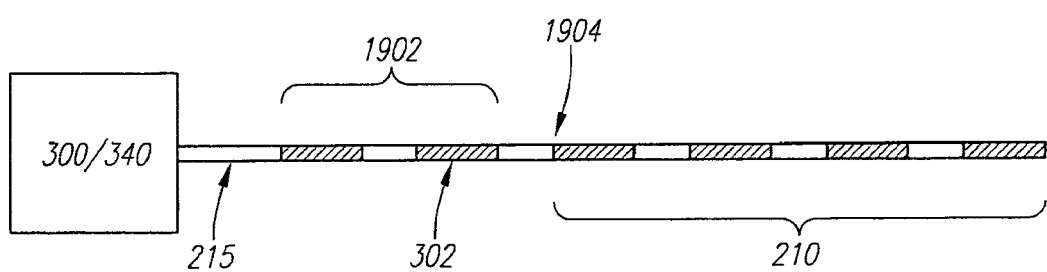
FIG. 19 illustrates one embodiment directed to establishing a reference grating or sensor.

Referring to FIG. 19, in one embodiment, a data acquisition and analysis software, which may, for example, reside in a controller or associated memory of a computer, MID controller, electronics rack or other suitable controller of a robotic instrument system illustrated in FIGS. 22A-C), is configured to pass over, disregard or ignore the first number N gratings 1902, thereby placing the reference 1904 at the location of the N+1$^{th}$ grating 302. In the illustrated embodiment, the first two FBGs 302 are ignored, thereby placing the reference 1904 at the third FBG 302, which is also at the beginning or proximal end of catheter 210. This method will provide shapes and location measurements relative to the location of the reference grating.

In other embodiments, systems and methods are directed to using software executed by a controller 340 to select a reference FBG 302, a measurement FBG 302 and/or a length or window of a FBG 302 to be measured or analyzed. For example, in one embodiment, the location of a reference FBG 302 is fixed at a proximal end of a catheter 210 as described above, and the location where the measurement is to be performed, or the measurement FBG 302 to be selected, is flexibly controlled via software such that the selected measurement FBG 302 may change during the analysis. Further, whichever FBG 302 is selected at a given time for measurement, the controller 340 software can also be executed to select the length of a selected measurement FBG over which the measurement is to be performed. In this regard, the length or window can be the entire length of a selected measurement FBG 302, or the length or window may be a portion or segment thereof. For example, about half of a measurement FBG 302 may be selected for measurement rather than the entire FBG 302. Embodiments may be implemented using continuous, overlapping or partially overlapping gratings 302.

If absolute location of the tip is needed, and if the first N FBGs 1902 sensors are ignored as shown in FIG. 19, then another independent method can be used to obtain the absolute or relative position of the reference 1904. This independent method may be another fiber 215 which has it tip at the location of the N+1$^{th}$ FBG 302 on the first fiber 215 is, or it may be an EM based sensor attached on the location of the N+1$^{th}$ FBG 302 or some other device, in all of these cases, the absolute location of the N+1$^{th}$ FBG 302 is measured or its relative location with another absolute reference is measured.

Various systems and components may be utilized to implement embodiments, and selection of a FBG 302 as a reference grating or a measurement may be performed using hardware, software or a combination thereof. Examples of systems and components thereof that may be used with or to implement embodiments are described in further detail in U.S. Provisional Application Nos. 60/925,449 and 60/925,472, filed on Apr. 20, 2007, and U.S. application Ser. No. 12/106,254, filed on Apr. 18, 2008, the contents of which were previously incorporated herein by reference.

Two fibers may be used for measuring twist, e.g. as described in U.S. Patent Application No. 60/925,449, "Optical Fiber Shape Sensing System", filed Apr. 20, 2007, previously incorporated herein by reference. Two or more fibers 215, each of which has a single core or multiple cores, may also be used to improve location accuracy. If the geometric or spatial relationship between the fibers 215 is known and invariant, then the independent location measurements from each fiber 215 can be averaged together resulting in improved signal to noise ratio and thereby result in improved accuracy. This technique of improving accuracy works if the noise in each measurement is independent of the noise in the other measurements. However, for any measurement system such as the fiber based measurement system, independent noise will exist. Invariance in the location of the two fibers 215 may be obtained through suitable design.

In many minimally invasive interventional systems, such as those made by Hansen Medical, Mountain View, Calif., there exists a disposable component (for example, a catheter) which typically enters a human body, and a non-disposable piece, which may, for example, house the mechanisms to control the disposable component. It may be through these controls that navigation of the disposable component is achieved within the body. As described above, according to one embodiment, the instrument 210 or may be coupled to a shape and location measuring fiber 215. Consequently, the connector(s) between the disposable and non-disposable components are configured to accommodate the catheter 210 and the fiber 215.

Embodiments address mechanical aspects associated with use of an optical fiber sensor 215 in robotic surgical components including at the coupling point or interface prior to the fiber 215 exiting the instrument and allows for movement of a fiber 215 within the instrument. This is achieved by providing slack at the proximal end since the distal end is typically positioned within the body, and the fiber 215 would probably be constrained in some fashion at the distal end. In this manner, embodiments address connection issues involving the catheter or elongate instrument 210 flexing or bending by providing slack to the fiber 215 to prevent breaking or excessive straining of the fiber 215. Such slack or "service loop" can be introduced in various ways.

Figure 20:
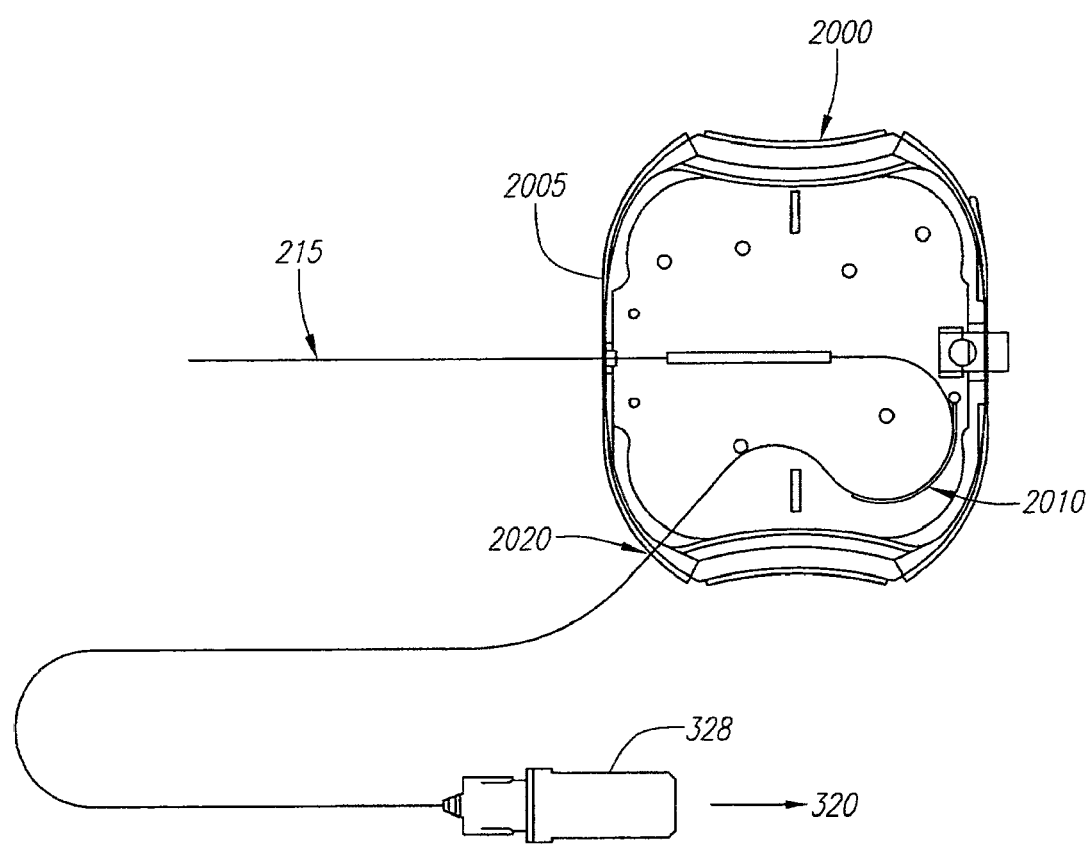
FIG. 20 illustrates one embodiment of a connector for providing slack and a grating or sensor reference.

For example, referring to FIG. 20, in one embodiment, a fiber 215 is shown entering a splayer 2000 through a wall or side 2005 and traversing a path through the splayer 2000 that provides slack 2010. For ease of illustration and explanation, FIG. 20 is a top view of the interior of a splayer 2000, and the catheter 120 is not shown, but would be positioned to the left of the splayer 2000. If the catheter 210 and fiber 215 move outwardly to the left, some of this slack 2010 will be taken up or reduced. Slack 2010 may also be provided in other ways and may be outside of the splayer 2000.

Embodiments address another issue related to the position of the splayer 2000 in relation to the location of a FBG 302 (FBGs are not illustrated in FIG. 20 for ease of illustration), e.g., a first FBG 302(1), although not necessarily the first FBG 302, which serves as a reference FBG 2020. In this embodiment, the reference FBG 2020 is positioned such that its location is precisely known. In this manner, the location of the reference FBG 2020 can be precisely known and is suitable for fiber based location measurement devices that depend on various small measurements that start from or based on the reference. For example, the location of a second grating 302 is measured in relation to the first grating 302, the location of the third grating 302 is measured in relation to the second grating 302, and so on. Thus if the absolute location of the reference grating 2020 is not known in relation to some coordinate system, then the absolute position of a second grating 302 or the position of a third grating 302 or any grating 302 that is beyond the reference grating 2020 is not known.

In some cases, it may not be necessary to know the absolute positions of the gratings 302; it may be only necessary to know the relative location of the second, third and other gratings 302 in relation to the reference grating 2020. In both of these cases where the absolute position or the relative position is required, it still is necessary to ensure that the reference grating 2020 does not move, or if it does move, that some adjustment or accommodation is utilized to know the location of the reference grating 2020.

As shown in FIG. 20, a fiber 215 is attached to a wall of the splayer 2000, and a grating 302, e.g. a first grating, is placed within the fiber 215 at this "reference" location. This ensures that the reference grating 2020, the first grating in this example, does not move relative to the wall of the splayer 2000. Since the splayer 2000 is a rigid component, the location of the reference grating 2020 is precisely known.

Figure 21:
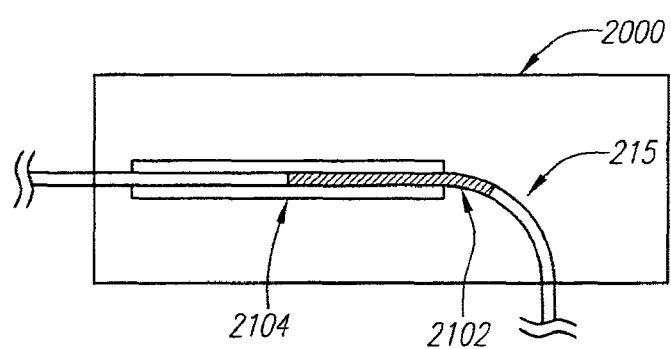
FIG. 21 illustrates an apparatus constructed according to another embodiment that is configured to accommodate a grating having a portion of which that is within a sleeve and a portion of which is outside of the sleeve.

In an alternative embodiment, referring to FIG. 21, a long first grating 2102 is provided. A portion of the grating 2102 is in a rigidly placed sleeve 2104 (which is also rigid). A portion of the grating 2102 is positioned within the sleeve 2104, and a portion is positioned outside of the sleeve 2104. In certain embodiments, a multi-core fiber 215 has multiple cores 304 that are spaced around the neutral axis of the fiber 210. This arrangement ensures that sections of the fiber cores 304 outside of the sleeve 2104 that are bent will experience a different strain compared to sections of the cores 304 that are inside of the sleeve 2104 and that are linear or straight. Reflected light 226 from this grating 2102 contains two peaks. A first peak occurs at a frequency corresponding to the strain experienced by the portion of the grating 2102 that is located outside of the sleeve 2104, and a second peak occurs at a frequency corresponding to the strain experienced by the portions of the grating 2102 that are located inside of the sleeve 2104. The relative locations and the width of the grating 2104 can be used to determine the exact position of the reference sensor 2020.

Yet other embodiments involve apparatus and methods for determining the position of the reference sensor or grating 2020. External sensors, such as precision linear encoders, electromagnetic localization sensors, or potential-difference-based localization sensors may be attached at the location of the reference sensor 2020. These sensors may then be utilized to provide the location of the reference sensor 2020.

As described above, minimally-invasive interventional and/or diagnostic systems often involve both disposable components (such as a splayer 2000) and non-disposable components (such as a light source or instrument driver). In such a system, the integrity of the connection between the disposable component and a non-disposable component should be high. For this purpose, an integrity test can be performed by emitting light or a test signal into the disposable component and analyzing the light reflected there from. For example, the received. signal 226 from each grating 302, particularly the first or reference grating 2020 may be analyzed for various parameters, particularly for intensity. If the intensity is low, then the connector may be bad or the connection may not have been made properly. A warning can then be generated to warn the operator to check the connection.

In a robotic surgical system that controls a minimally invasive elongate instrument or catheter 210, it is important to maintain the structural integrity of the instrument 210. If, for example, mechanisms that control the navigation of the elongate instrument 210 break, then the controllability of the system may be compromised. To address these issues, in one embodiment, a fiber 215 is attached to an elongate instrument or catheter 210 to monitor such mechanical breakages. As the fiber 210 based shape and location measurement device is attached to the elongate instrument or catheter 210, the shape of the instrument or catheter 210 can be monitored. If the shape is anomalous in some way indicating a breakage, then a warning is generated for the operator and the procedure may be stopped manually or automatically.

Having described various apparatus and method embodiments in detail, further details of a robotic surgical systems and components thereof in which embodiments of the invention may be implemented are described with reference to FIGS. 22A-26B, and FIGS. 23A-B and 26A-B illustrate how embodiments of the invention can be implemented and including various components of the robotic surgical system described. A description a system and methods for utilizing localization data for closed-loop control of a robotic catheter system in which embodiments may be implemented is provided with reference to FIGS. 22A-25F.

Referring to FIGS. 22A-F, one example of a robotic surgical system 2200 in which embodiments of the invention that utilize an optical fiber sensor 215 may be implemented includes an operator work or control station 2205, which may be configured as, or include control, processor or computer software and/or hardware, which may perform various data processing functions on data from an optical fiber sensor 215 and execute various processing and control functions in response thereto.

The workstation 2205 is located remotely from an operating table 2207, an electronics rack 2210, a setup joint mounting brace 2215, and motor-driven controller 1200 in the form an instrument driver 2220. A surgeon or operator 2225 seated at the operator workstation 2205 monitors a surgical procedure, patient 1500 vitals, and controls one or more flexible catheter assemblies that may include a coaxially-associated instruments of an outer sheath catheter 220, an inner coaxially-associated catheter 210 such as a guide catheter, and working instrument 240 such as a guidewire, a pusher wire, an ablation catheter, a laser ablation fiber, a grasper, a collapsible basket tool, etc., which is positioned within the working lumen defined by the inner catheter 210.

Although the various components of the system 2200 are illustrated in close proximity to each other, components may also be separated from each other, e.g., in separate rooms. For example, the instrument driver 2220, the operating table 2207 and a bedside electronics box may be located in the surgical area, whereas the operator workstation 2205 and the electronics rack 2210 may be located outside of the surgical area behind a shielded partition. System 2200 components may communicate with other components via a network, thus allowing for remote surgery such that the surgeon 2225 may be in the same or different building or hospital site. For this purpose, a communication link may be provided to transfer signals between the operator control station 2205 and the instrument driver 2220. Components may be coupled together via cables 2230 as necessary for data communication. Wireless communications may also be utilized.

Referring to FIG. 22B, one suitable operator workstation 2205 includes a console having one or more display screens 2232, which may serve as display 340, a master input device (MID) 2234 and other components such as a touchscreen user interface 2236, and data glove input devices 2238. The MID 2234 may be a multi-degree-of-freedom device that includes multiple joints and associated encoders. MID 2234 software may be a proprietary module packaged with an off-the-shelf master input device system, such as the Phantom® from SensAble Technologies, Inc., which is configured to communicate with the Phantom® Haptic Device hardware at a relatively high frequency as prescribed by the manufacturer. Other suitable MIDs 2234 are available from suppliers such as Force Dimension of Lausanne, Switzerland, The MID 2234 may also have haptics capability to facilitate feedback to the operator, and software modules pertinent to such functionality may be operated on the master computer. An example of data glove software 2244 is a device driver or software model such as a driver for the 5DT Data Glove. In other embodiments, software support for the data glove master input device is provided through application drivers such as Kaydara MOCAP, Discreet 3D Studio Max, Alias Maya, and SoftImage|XS1.

The instrument driver 2220 and associated flexible catheter assembly and working instruments may be controlled by an operator 2225 via the manipulation of the MID 2234, data gloves 2238, or a combination of thereof. During use, the operator 2225 manipulates a pendant and MID 2234 to cause the instrument driver 2220 to remotely control flexible catheters that are mounted thereon. Inputs to the operator workstation 2205 to control the flexible catheter assembly can entered using the MID 2223 and one or more data gloves 2238. The MID 2234 and data gloves 2238, which may be wireless, serve as user interfaces through which the operator 2225 may control the operation of the instrument driver 2220 and any instruments attached thereto. It should be understood that while an operator 2225 may robotically control one or more flexible catheter devices via an inputs device, a computer or other controller 340 of the robotic catheter system 2200 may be activated to automatically position a catheter instrument 210 and/or its distal extremity 211 inside of a patient 1500 or to automatically navigate the patient anatomy to a designated surgical site or region of interest.

Referring to FIG. 22C, a system architecture of a robotic catheter system 2200 includes a controller 340 in the form of a master computer 2241 that manages operation of the system 2200. The master computer 2241 is coupled to receive user input from hardware input devices such as a data glove input device 2238 and a haptic MID 2234. The master computer 2241 may execute MID hardware or software 2243, data glove software 2244 and other software such as visualization software, instrument localization software, and software to interface with operator control station buttons and/or switches. Data glove software 2244 processes data from the data glove input device 2238, and MID hardware/software 2243 processes data from the haptic MID 2234. The master computer 2241 or another computer or controller may also receive data from an optical fiber sensor 215.

For example, in one embodiment, in response to the processed inputs, e.g., in response to the data or analysis of such data of detected reflected light signals 326 front the optical fiber sensor 215, the master computer 2241 processes instructions to instrument driver computer 2242 to activate the appropriate mechanical response from the associated motors and mechanical components of the driver 2220 to achieve the desired response from the flexible catheter assembly including a sheath 220 and catheter or elongate instrument 210.

Further, in another embodiment, the master computer 2241 or other suitable computer or controller may control actuation of the at least one servo motor to activate the appropriate mechanical response from the associated motors and mechanical components of the driver 2220 to achieve the desired response from the flexible catheter assembly including a sheath 220 and catheter or elongate instrument 210 based at least in part upon a comparison of an actual position the instrument derived from the localization data to a projected position of the instrument derived from a kinematic model of the instrument.

As a further example, in one embodiment, the master computer 2241 or another suitable computer may be configured to determine patient respiration based on signals 326 received from respective Bragg gratings 302 on the one or more Bragg sensor optical fibers 215. Thus, the master computer 2241 can coordinate control of one or more instruments, such as a catheter, monitor one or more instruments, and/or monitor a patient. For example, a controller or computer 340 may be configured to determine one or more position and/or orientation variables of an instrument driver 2220, an instrument such as a catheter 210, and a patient's body based on detected reflected light signals 326 received from the respective Bragg gratings 302 on the different fibers 215.

In yet another embodiment, in response to the data or analysis of such data of detected reflected light signals 326 from the optical fiber sensor 215, a controller 340 or master computer 2241 may generate and display a graphical representation of an instrument body such as a catheter 210 by depicting one or more position and/or orientation variables thereof based upon reflected light signals 326 received from the one or more Bragg gratings 302.

Figure 22D:
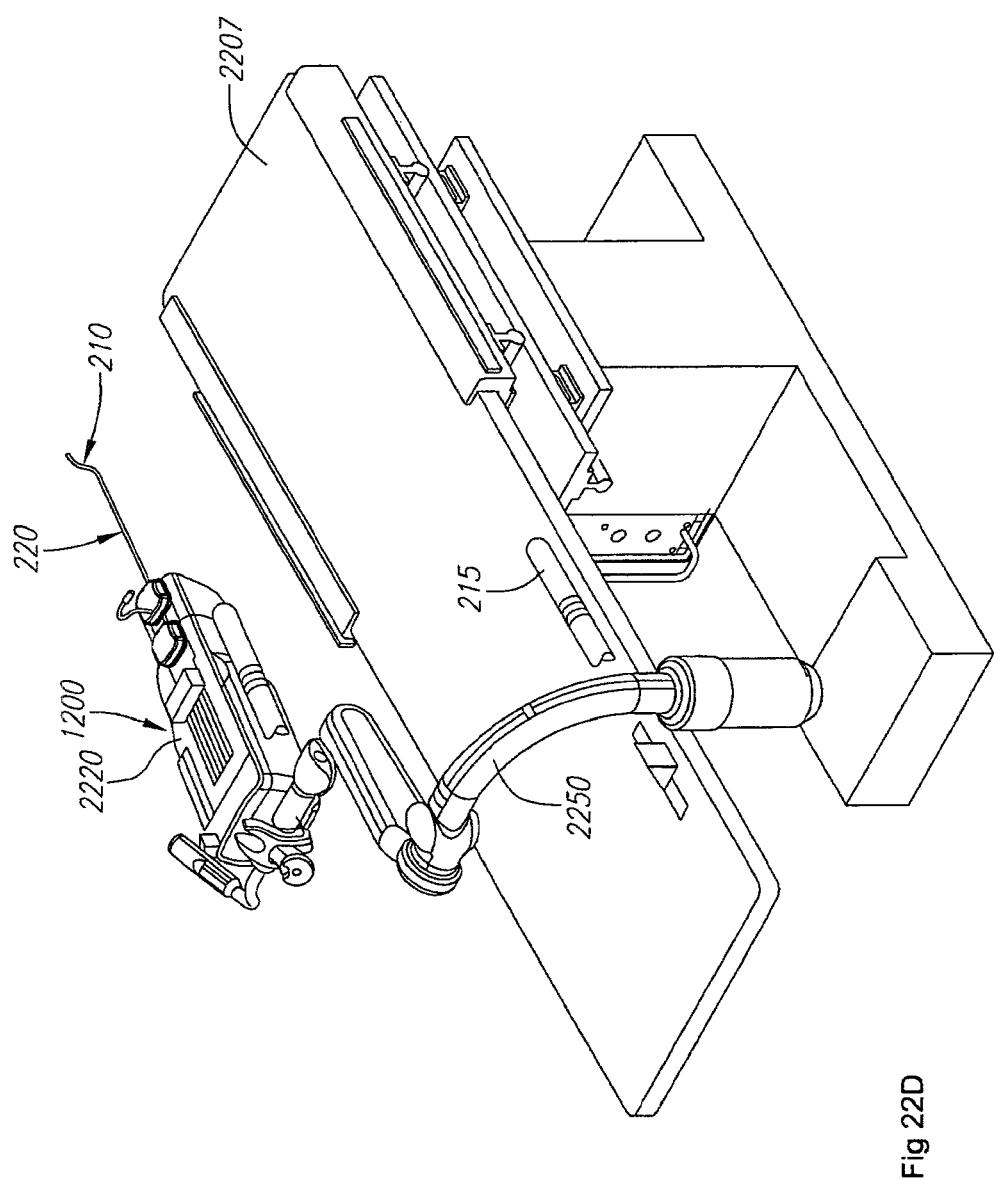
Figure 22F:
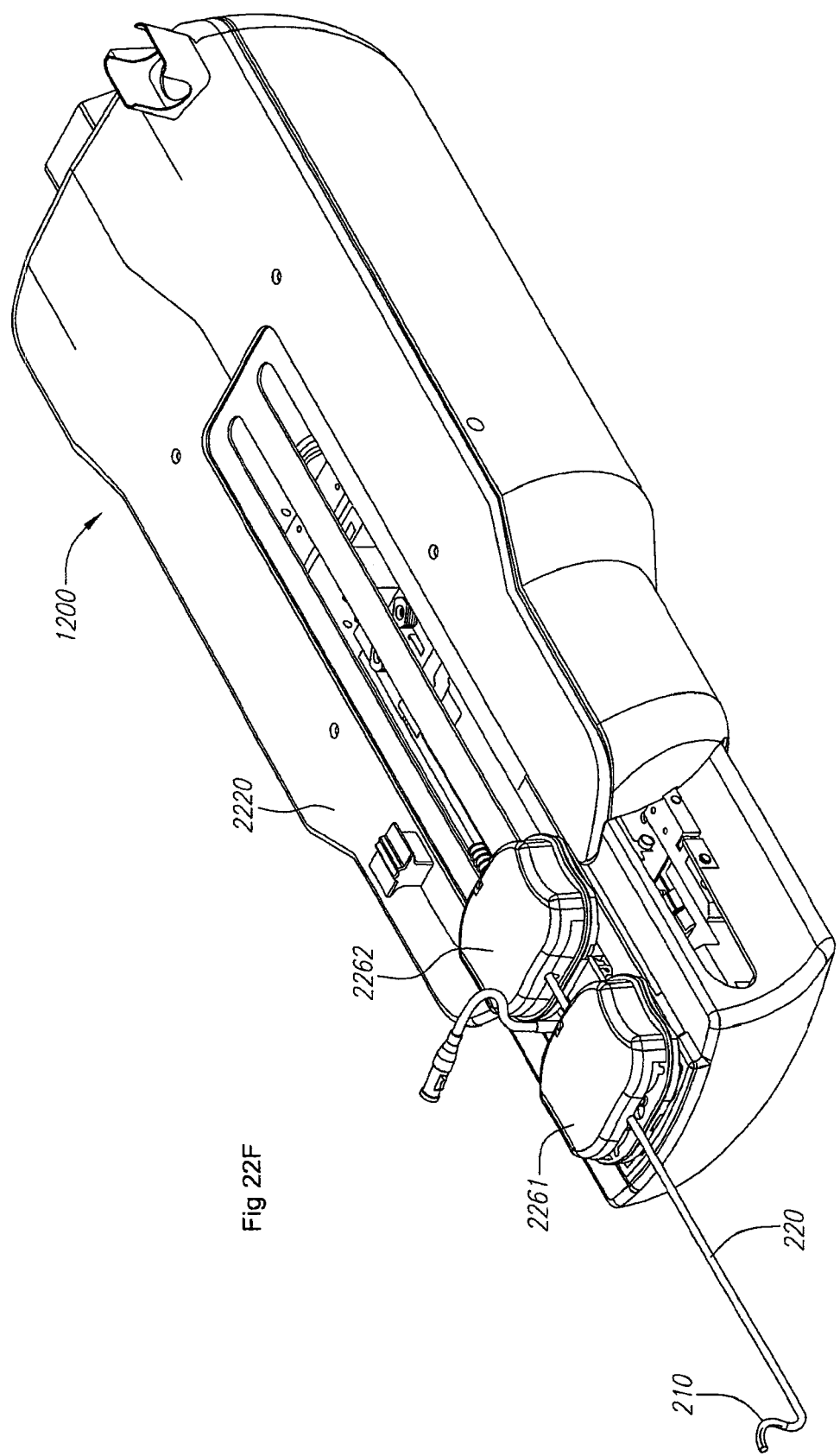

Referring to FIG. 22D, an example of a setup joint, instrument mounting brace or support assembly 2250 (generally referred to as a support assembly 2250) that supports the instrument driver 2220 above the operating table 2207 is an arcuate-shaped structure configured to position the instrument driver 2220 above a patient 1500 lying on the table 2207 for convenient access to desired locations relative to the patient 1500. The support assembly 2250 may also be configured to lock the instrument driver 2220 into position. In this example, the support assembly 2250 is mounted to the edge of a patient bed 2207 such that an assembly including a catheter 210 mounted on the instrument driver 2220 can be positioned for insertion into a patient 1500 and to allow for any necessary movement of the instrument driver 2220 in order to maneuver the catheter assembly during a surgical procedure.

As shown in FIGS. 22A, 22D, 22E and 22F, and as illustrated in FIG. 2A, a flexible catheter assembly for use in embodiments includes three coaxially-associated instruments including an outer sheath catheter 220, an inner coaxially-associated catheter or guide catheter 210, and a working instrument (not illustrated in FIGS. 22A, 22D, 22E-F) such as a guidewire, pusher wire, ablation, catheter, laser ablation fiber, grasper, collapsible basket tool, etc.—a myriad of small working tools may be utilized and localized) positioned through the working lumen formed by the inner catheter 210.

In the illustrated example, a splayer 2261 having one or more control elements or pull wires and a flexible sheath member 220 having a central lumen. Similarly, a splayer 2262 located proximally of the splayer 2261 for the catheter 210 has one or more control elements or pull wires. The catheter instrument 210 has a central lumen configured for passage of a working element or instrument 240. Prior to use, the catheter 210 is inserted into the sheath 220 such that these components are coaxially positioned. Both splayers 2261, 2262 are mounted to respective mounting plates on the instrument driver 2220, and the splayers 2261, 2262 are controlled to manipulate the catheter and sheath instruments 210, 220.

In one embodiment, a system includes an elongate instrument or catheter 210 having one or more control elements or pull wires operatively coupled to at least one servo motor of the instrument driver 2220 (e.g. as generally illustrated in FIGS. 12 and 13) such that the instrument 210 moves in response to actuation of the at least one servo motor. The optical fiber sensor 215 supplies localization data indicative of a spatial position of at least a portion of the instrument 210, and the controller 340 or other system control element controls actuation of the at least one servo motor in order to control movement of the instrument 210 based at least in part upon a comparison of an actual position the instrument 210 derived from the localization data to a projected position of the instrument derived from, for example, a kinematic model of the instrument 210.

As shown in various system figures, optical fiber sensors 215 can be coupled to or integral with various system components. In certain embodiments, an optical fiber sensor 215 is coupled to or integral with a catheter or elongate instrument 210 (e.g., within a lumen 213 or lumen 217), a sheath 220, the instrument driver 2220, the patient's bed 2207, and/or attached to the patient 1500. For example, FIG. 22A illustrates an embodiment in which optical fiber sensors 215 are coupled to two system components (instrument driver 2200 and a bed or table 2207) and the patient 1500, and a catheter or other elongate instrument 210 may also include an optical fiber sensor 215. For ease of illustration, various figures show an optical fiber sensor 215 and its associated system component without associated connectors, etc.

Figure 23B:
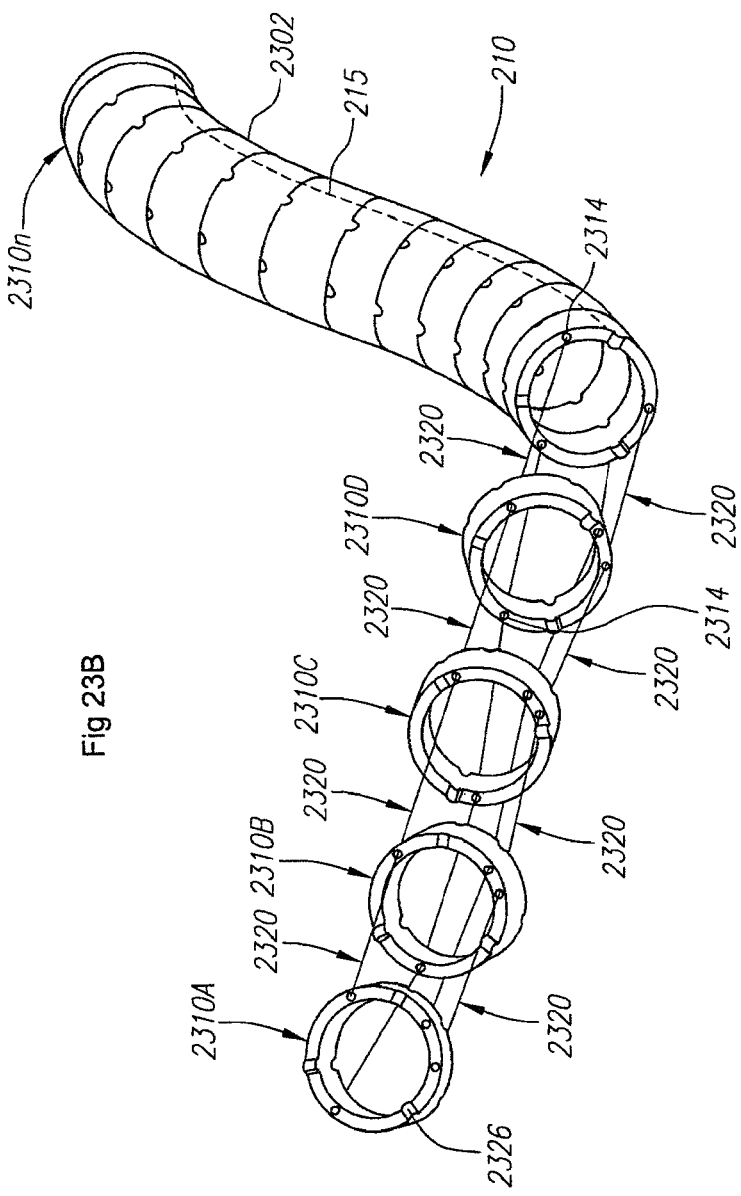
Figure 23C:
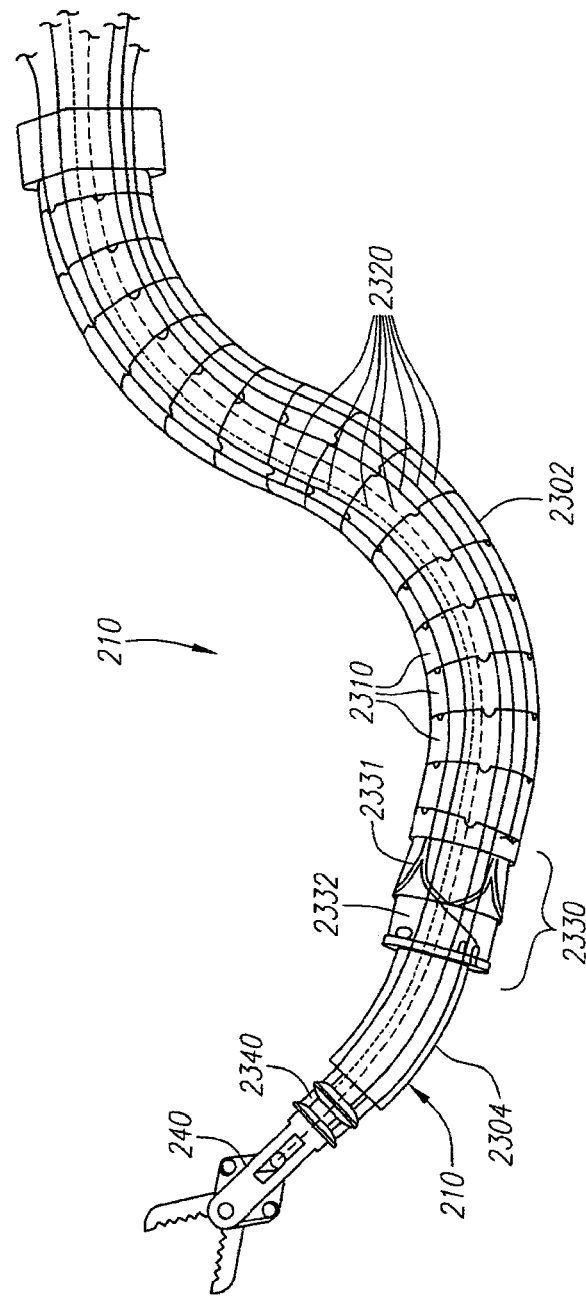

FIGS. 23A-C illustrate an elongate catheter 210 in the form of a sheath catheter 2302 through which another instrument such as a guide catheter 2304 may extend. According to embodiments, optical fiber sensors 215 can be coupled to or integral with the sheath catheter 2302 and/or the guide catheter 2304, e.g., positioned within a suitable lumen or extending through a wall of an instrument. In the illustrated embodiment, the sheath catheter includes multiple segments 2310(a-n) (generally segment 2310). Each segment 2310 may be generally the same shape, e.g. round ring-like structures, but may differ to some degree. Segments 2310 can also be other shapes, e.g., square, rectangular, triangular, pentagonal, hexagonal, octagonal, circular, spherical, elliptical, star, etc. Pull wires 2320 are operably coupled to each segment 2310 and extend through aligned passages, apertures or channels 2314 defined by a wall of each segment 2310. For example, a pull wire 2320 may be coupled to a distal most segment 2310 such that placing the pull wire 2320 in tension also places more proximal segments 2310 in tension. In another embodiment, the pull wires 2320 can be attached to some or all of the segments 2310, e.g., attached to an exterior surface of a segment 2310.

In certain embodiments, the wall of each segment 2310 can also define an aperture 213 (as illustrated in FIG. 2) for an optical fiber sensor 215. In this manner, control elements or pull wires 2320 and optical fiber sensors 215 are advantageously routed through the body or wall of segments 2320 rather than through an inner or central lumen defined by a collection of segments 2320. In this manner, embodiments advantageously reduce the components extending through the inner or central lumen, thereby providing more space through which other instruments and devices, such as a guide catheter 2304 and/or working instrument 240 may be inserted. Instruments can also be advanced through the sheath catheter 2302 more easily since the control elements 2320 and optical fiber sensor 215 do not interfere with these components. In an alternative embodiment, an optical fiber sensor 215 extends through an inner or central lumen defined by the collection of segments 2320.

Individual segments 2320 of a sheath catheter 2302 having shaped, interlocking top and bottom surfaces that allow segment 2320 to matingly engage adjacent segments 2320. In the illustrated embodiment, each segment 2320 includes mating teeth or protrusions 2326 and notches or grooves 2328 that matingly engagement each other such that interlocking segments 2320 are not rotatable relative to each other. In this manner, aligned interlocking segments 2320 collectively define a catheter or elongate body structure 120 that defines a lumen that extends through the plurality of segment 2320 bodies. While the figures illustrate a structural configuration of one embodiment of a segment 2320, other numbers and arrangements of teeth or protrusions 2326, notches or grooves 2328 and apertures 2314, 213 for control elements 2320 and optical fiber sensors 215 may be utilized. Further, individual segments 2320 may have different numbers of teeth or protrusions and notches depending on the need to provide additional stability, support, and rigidity to the sheath catheter 2302 when the sheath catheter 2302 is deployed. p With the sheath 2302 configuration illustrated, segments 2320 and be placed in tension to place the group of segments 2320 in tension or a rigid state, or placed in a relaxed, low tension or flexible state. Thus, one embodiment of a catheter or elongate instrument 120 in the form of a sheath catheter 2302 that may include an optical fiber sensor has controllable rigidity and can form a platform from which other instruments can extend and be controlled and provide rigidity and resistance to twisting or rotational loads on the sheath catheter 2302.

In addition to having an optical fiber sensor 215 as shown in FIG. 23A, a reference sensor may also be coupled to the sheath 2302 proximate the distal end opening. With this configuration, one or more position and/or orientation variables of the distal end portions of the respective instrument bodies are determined relative to the reference sensor.

Figure 24A:
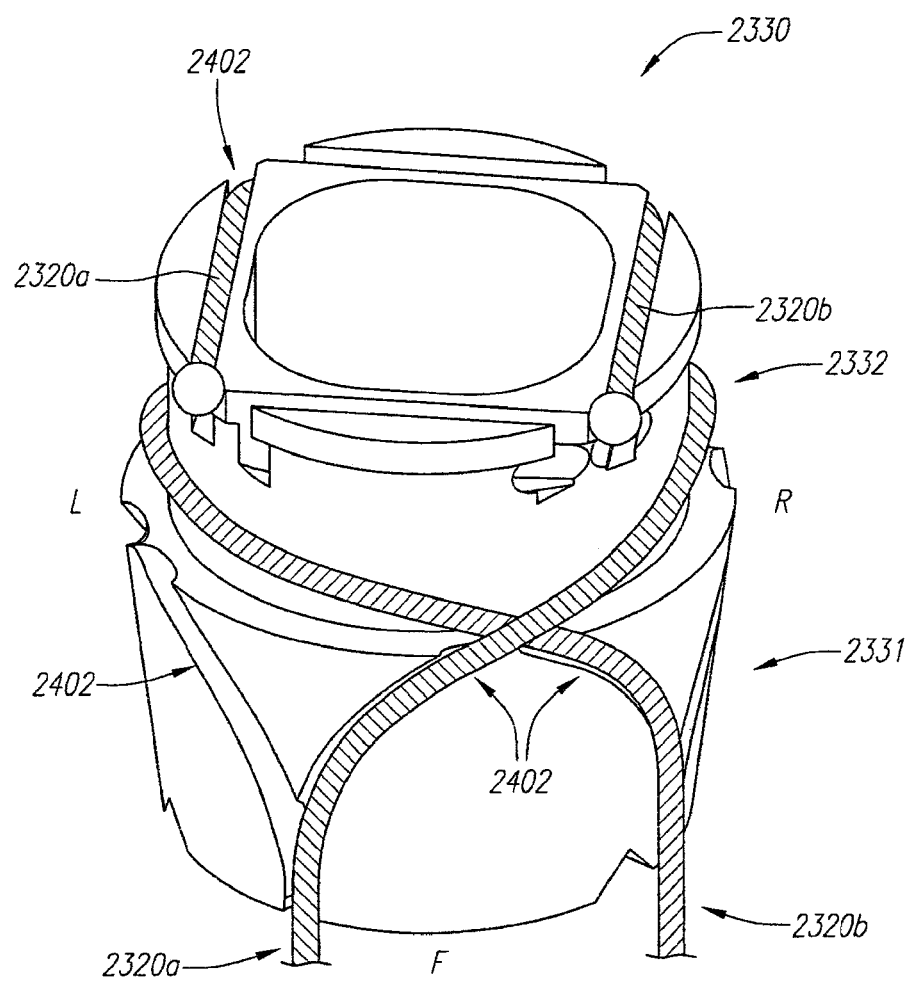
FIGS. 24A-D are different views of a rotatable apparatus that interfaces with the sheath catheter illustrated in FIGS. 23A-C.
Figure 24B:
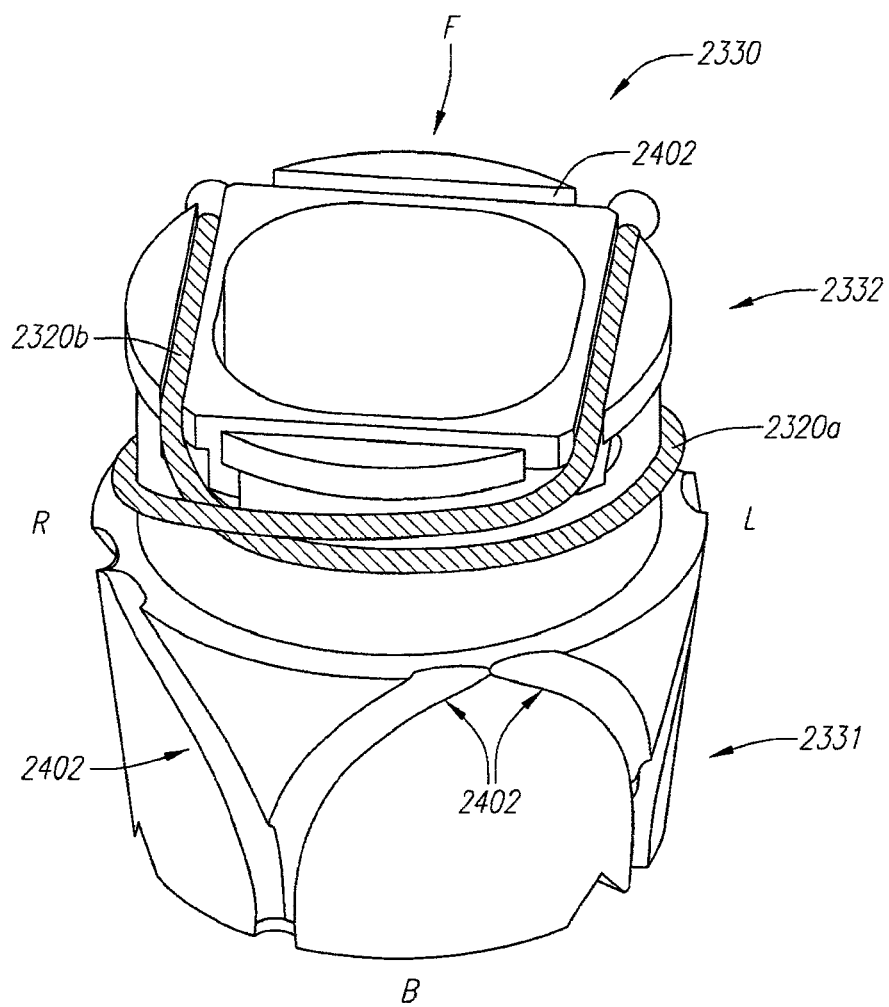
Figure 24C:
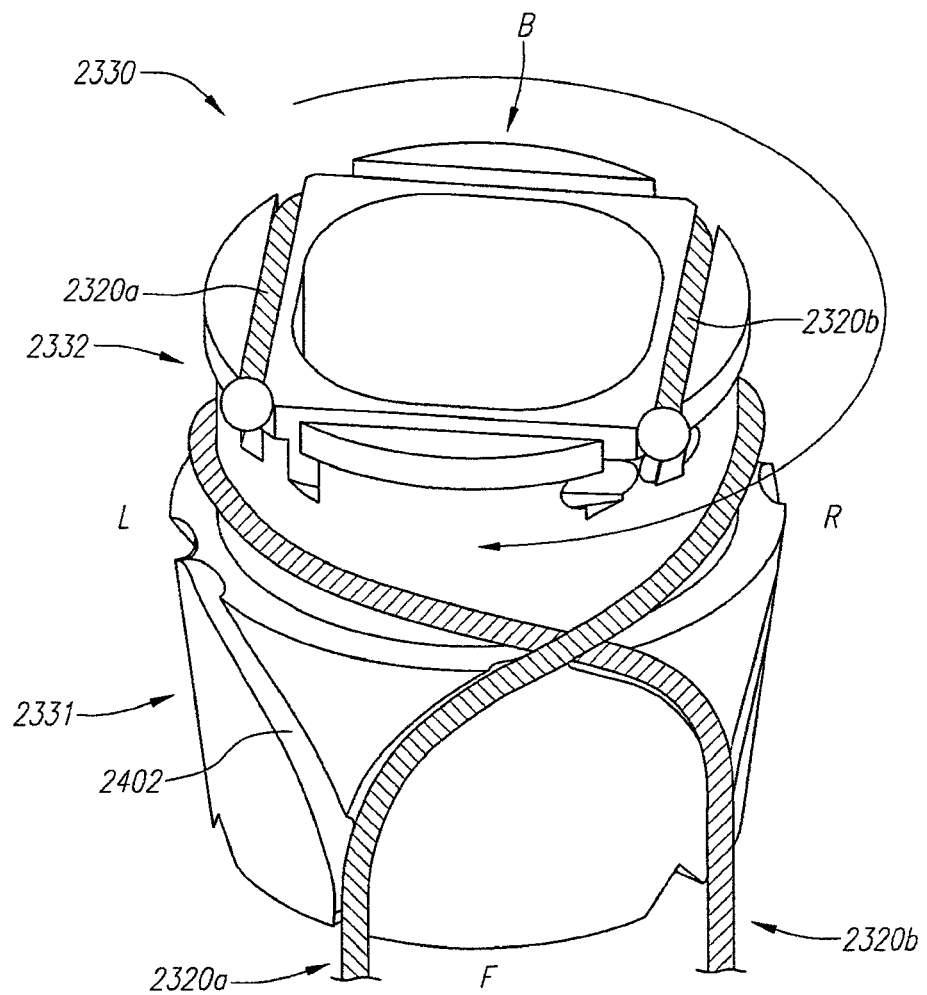
Figure 24D:
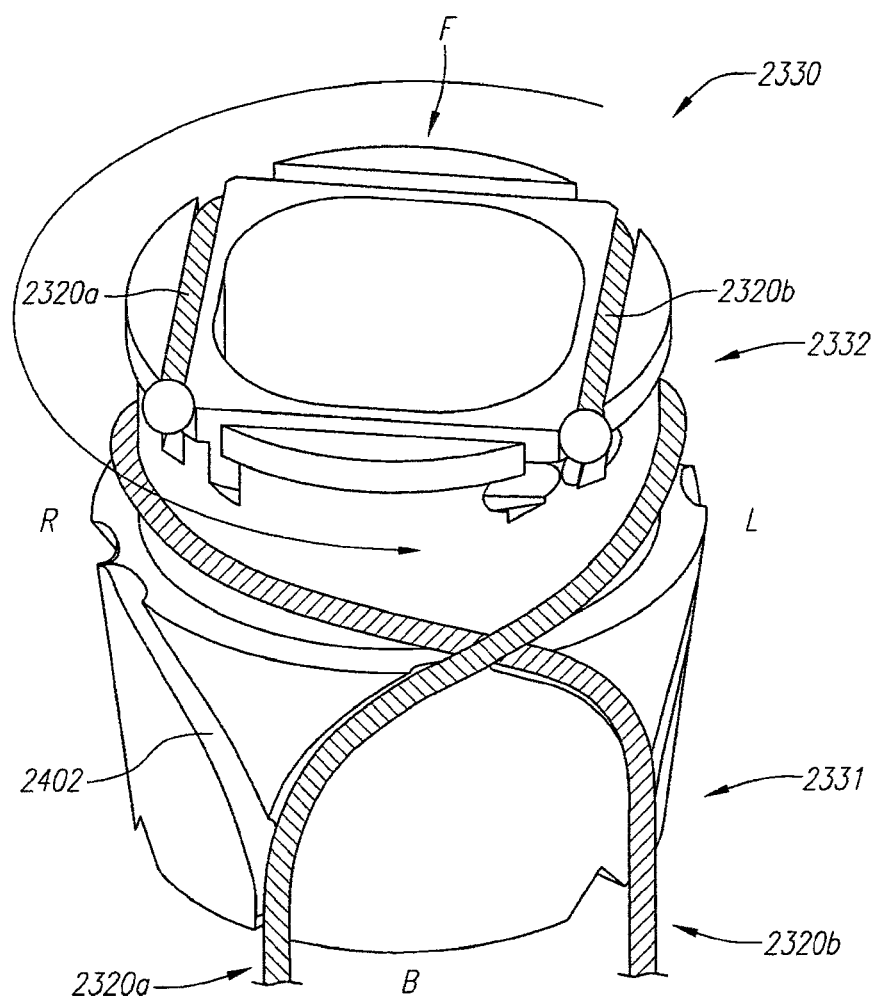
Figures 25A, 25B:
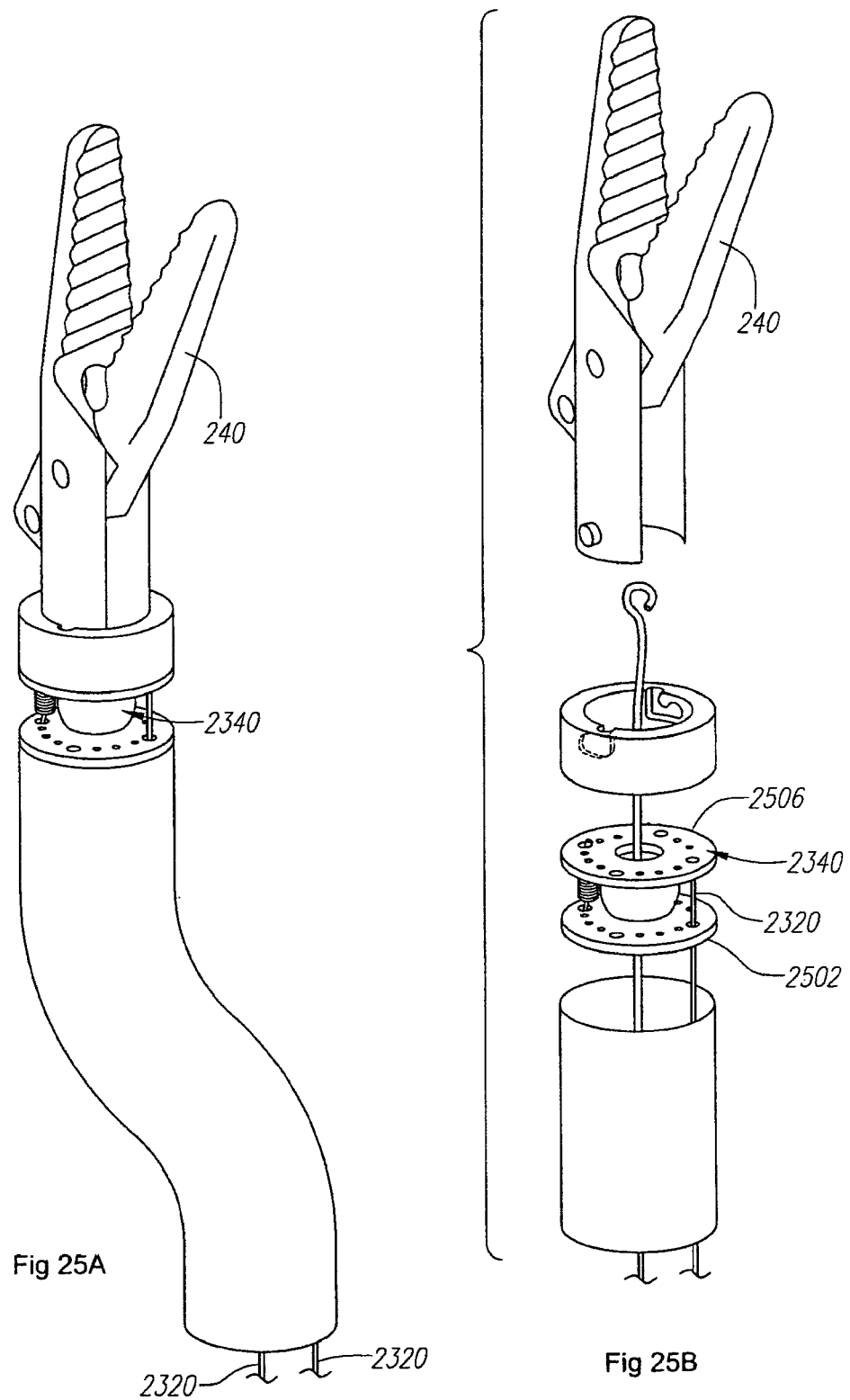

With continuing reference to FIG. 23A, and with further reference to FIGS. 24A-D, a rotatable apparatus 2330 is coupled to the sheath catheter 2302 and provides greater degrees of freedom and movement of a guide catheter 2304, an orientation platform 2340 and/or working instrument 240 coupled thereto or associated therewith. A rotatable apparatus 2330 may include an interface or wire guide apparatus 2331 and a rotatable collar, tool base or wire receive apparatus 2332 which are rotatably coupled together. Thus, a tool or other system component may be rotatably coupled to a distal end portion of a medical instrument, such as a sheath or guide catheter 2302, by manipulation of one or more control elements 207 that extend through grooves formed within rotatable apparatus 2330 to rotate the collar component 2332 clockwise (FIG. 24C) and counter-clockwise (FIG. 24D).

As shown in FIGS. 24A-D, outer surfaces of the interface and collar components 2331, 2332 defines one or more guides, channels or grooves 2402 that serve to guide, direct or route control element 2320 (two control elements 2320*a*,*b* are illustrated). In the illustrated embodiment, control elements 2302 wrap around a substantial portion of the rotatable collar 2331 such that manipulation of control elements 207 results in rotation of the rotatable collar 2332. FIG. 23C further illustrates how various control elements 207 may extend through a sheath catheter 2302 are connected to different components. Thus, pulling or placing tension on the control element 2320 rotates the collar 2332 and associated instruments such as a guide catheter 2304 and working instrument 240, thereby advantageously providing rotational control as well as articulation control of system components.

Referring to FIG. 23A, and with further reference to FIGS. 25A-F, an orientation platform 2340 of a robotic instrument system is configured to control a working instrument 240 (one example of which is illustrated) coupled to a distal end of a catheter instrument 2304 or other instrument of a. robotic medical system, e.g., a sheath 220 covered catheter 210. In the illustrated example, the interface or platform 2340 includes a base member or socket plate 2502 configured for coupling to a distal end of catheter instrument member, a spacer element 2504 and another socket plate or platform member 2506. The spacer element 2504 is retained or interposed between, and separates, the base member 2502 and the platform member 2506. The platform member 2506 is movable relative to the base member 2502 about the spacer element 2504. The interface or platform 2506 also includes a control element 2320, such as a pull wire, that extends through the catheter member, through an aperture defined by the base member 2502, and terminating at the platform member 2506. The platform 2340 may be used to control orientation of the platform member 2506 and an orientation of the working instrument 240 are controllably adjustable by manipulation of the control member 2320.

Further aspects of system components illustrated in FIGS. 23A-25F are described in various applications previously incorporated by reference.

Figure 26A:
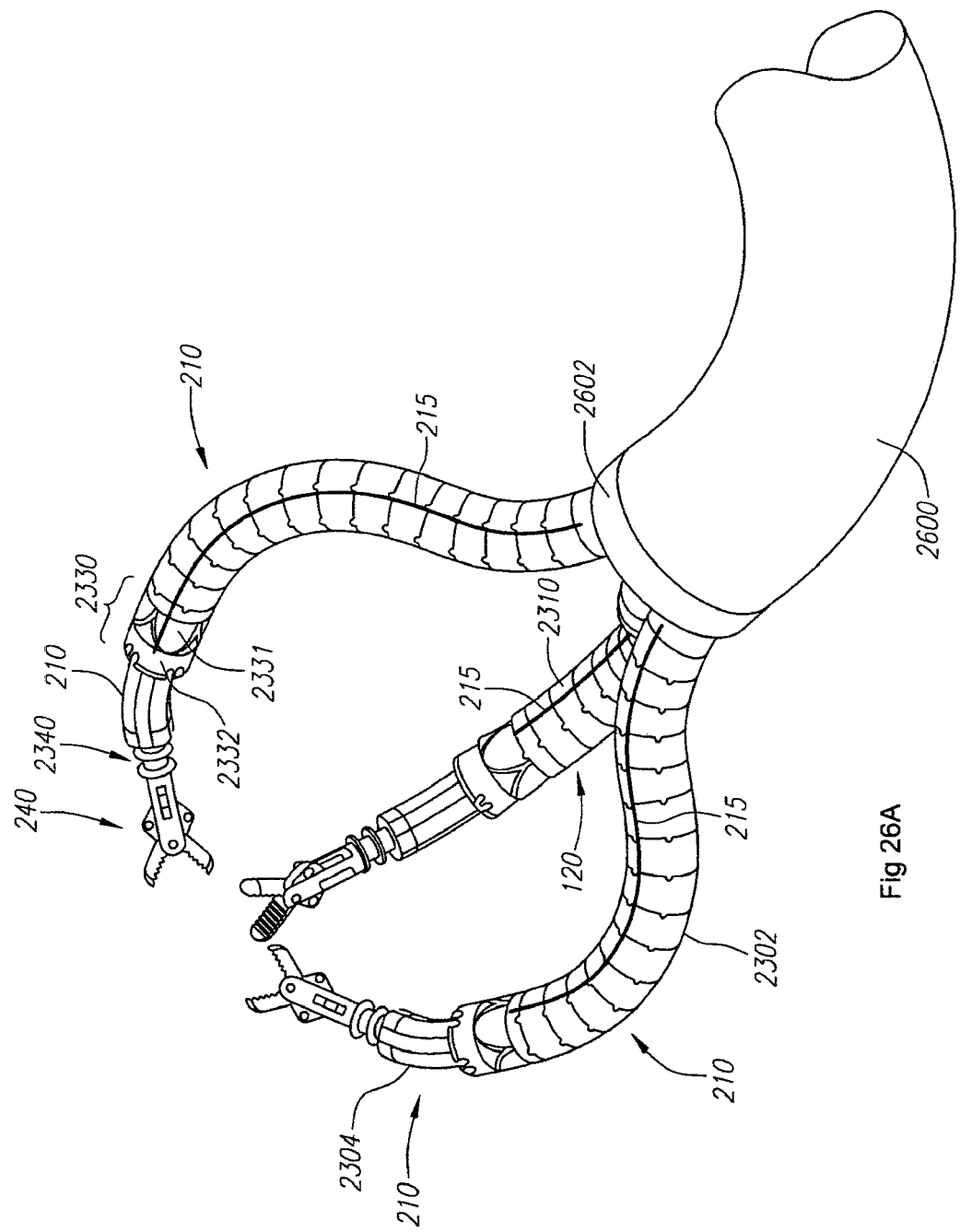

FIG. 26A illustrates another manner in Which embodiments may be implemented in which multiple optical fiber sensors 215 are coupled to or integral with multiple catheters coupled to respective rotatable apparatus and orientation apparatus components described above, and which are advanced through an outer or master sheath 2600.

Figure 26B:
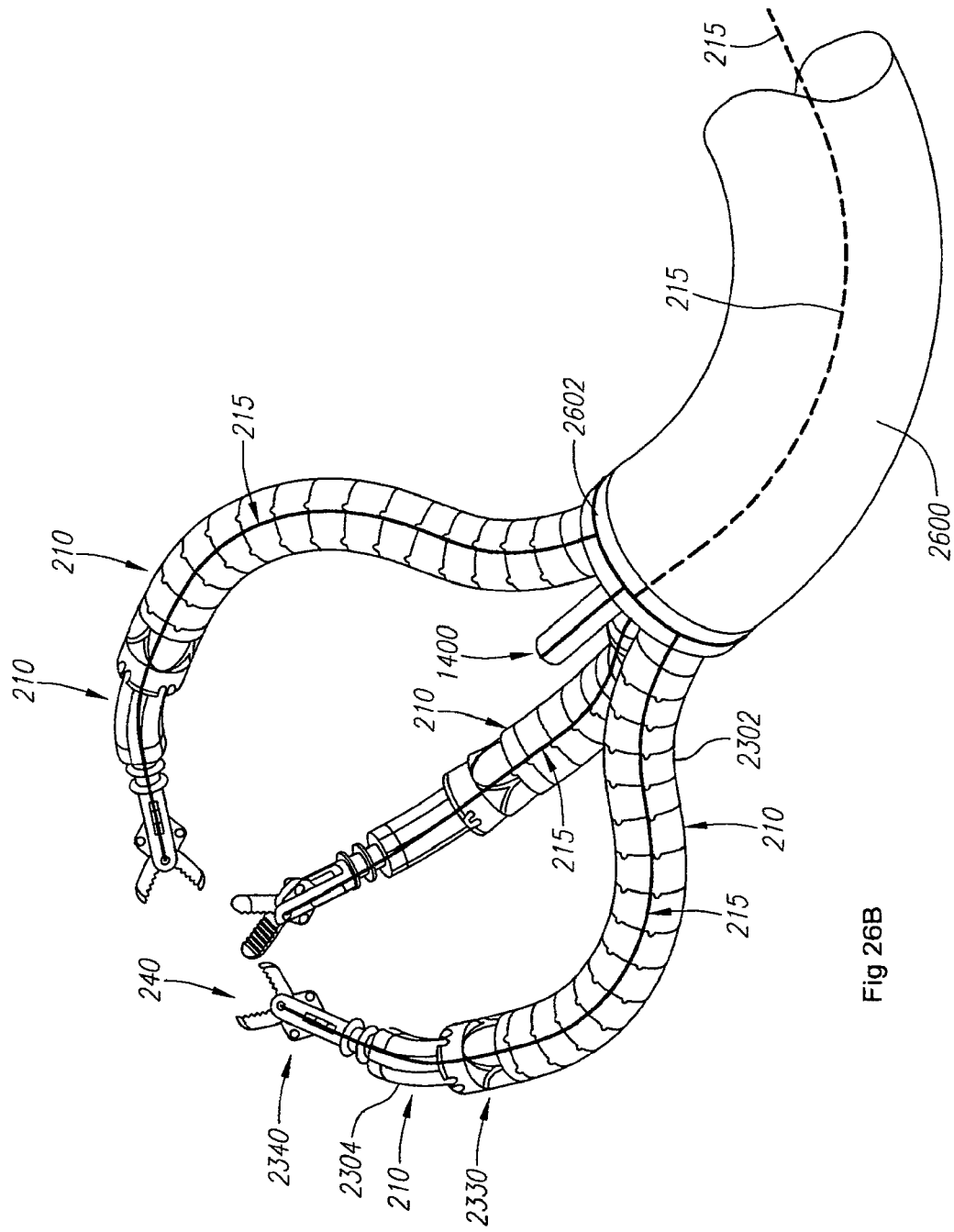

In the illustrated embodiment, each sheath catheter 2302 or a sub-portion thereof is localized utilizing an optical fiber sensor 215 which may be a Fiber Bragg Grating localization sensor. Other system components, such as an image capture device 1400 (as shown in FIG. 26B) may also be localized with an optical fiber sensor 215. Further, similar to other embodiments discussed above, other system components, such as an instrument driver 2220 and patient bed 1500 may also have optical fiber sensors 215. With this configuration, embodiments enable the entire environment (image capture device, each flexible arm, the main proximal arm, etc.) to be well characterized in near-real time, and the images from the image capture device 1400, such as a fluoroscopy device, may be appropriately associated with representations, cartoons and images produced from the depicted devices. Thus, embodiments provide apparatus and methods for combining or fusing a shape and localization measuring fiber 215 and robotic surgical system components.

Additionally, similar to apparatus and method embodiments discussed above, optical fiber sensors 215 coupled to each system component may provide for determining and displaying the orientation and the roll of the tip of the elongate instruments. This is particularly useful when planning surgery or placing leads.

Further, as shown in FIGS. 26A-B, a common reference device, or "control ring" 2602 is provided at the distal end of the master sheath 2600 or sheath like structure that carries the elongate instruments including sheath catheters 2302 and guide catheters 2304. This control ring 2602 can be used as a common reference for all the fibers 215 on elongate instruments, image capture devices, and the like which may extend distally from the control ring 2602 location. This common reference establishes a common coordinate frame for all the fibers 215 such that the shape and location of the fibers 215 may be measured in relation to the control ring 2602. This arrangement is particularly advantageous because the accuracy at the tip will be high due to the short length of the fiber 215 run, the twist and roll of the elongate instruments may result in smaller errors since the distance between the control ring 2602 and the tip is short, and the elongate instruments are all in the same coordinate frame, which also improves accuracy compared to use of different coordinate frames.

The location of the control ring 2602 may be localized in the world coordinate system by a separate fiber 215 (single or multiple core), which is helpful if elongate instruments, such as catheters 2302, 2304, image capture device 1400 platforms, and the like, which extend distally beyond the control ring 2602, are coordinated with other external medical imaging or data processing systems, such as fluoroscopy systems, magnetic resonance imaging systems, or geometric and/or electronic mappings and datasets.

For embodiments in which multiple elongate instruments 2302 and/or 2304 carry single tools, a single elongate instrument carries multiple tools, or multiple elongate instruments each carry multiple tools, fiber based shape and location measurement devices 215 may be mechanically associated with each tool or each elongate instrument or to both. It is not necessary that all tools or elongate instruments have a fiber 215 attached or coupled thereto. Each fiber 215 could be a single core Bragg grating sensor fiber or a multiple core fiber Bragg grating sensor. More than one fiber may be used per tool or per elongate instrument or catheter.

Accordingly, FIGS. 23A-C and 26A-B are provided to illustrate different ways embodiments can be implemented. It should be understood that an instrument may include other numbers of sheath catheters 2302, other numbers of guide catheters 2304, and that each catheter 210 having an optical fiber sensor 215 coupled thereto may have fibers of various lengths, positions and configurations.

Additionally, embodiments described above can be utilized with various manually or robotically steerable instruments, various localization systems and rendering of images to assist an operator, including those systems and methods described in the aforementioned patent application, U.S. application Ser. No. 11/637,951, the contents of which were previously incorporated herein by reference. FIGS. 27-43 are provided for reference and illustrate one example of a localization system that utilizes localization data for closed-loop control of a robotic catheter system in which embodiments of the invention may be implemented, and FIGS. 44-49 are provided for reference and illustrate one example of user interface presentation of captured or "cartoon" rendered images that are used to assist the operator in controlling a robotic catheter system or the like. Additional details regarding these systems are omitted for clarity and described in further detail in application Ser. No. 11/637, 951. Embodiments may also utilize other known localization and user interface presentation systems, and the systems and related methods shown in FIGS. 27-43 are provided as illustrative examples that may be used with embodiments.

FIGS. 27-37 depict various aspects of one embodiment of a SimuLink® software control schema for an embodiment of a physical system, with particular attention to an embodiment of a "master following mode." In this system, an instrument is driven by following instructions from a MID, and a motor servo loop embodiment, which comprises key operational functionality for executing upon commands delivered from the master following mode to actuate the instrument.

Figure 27:
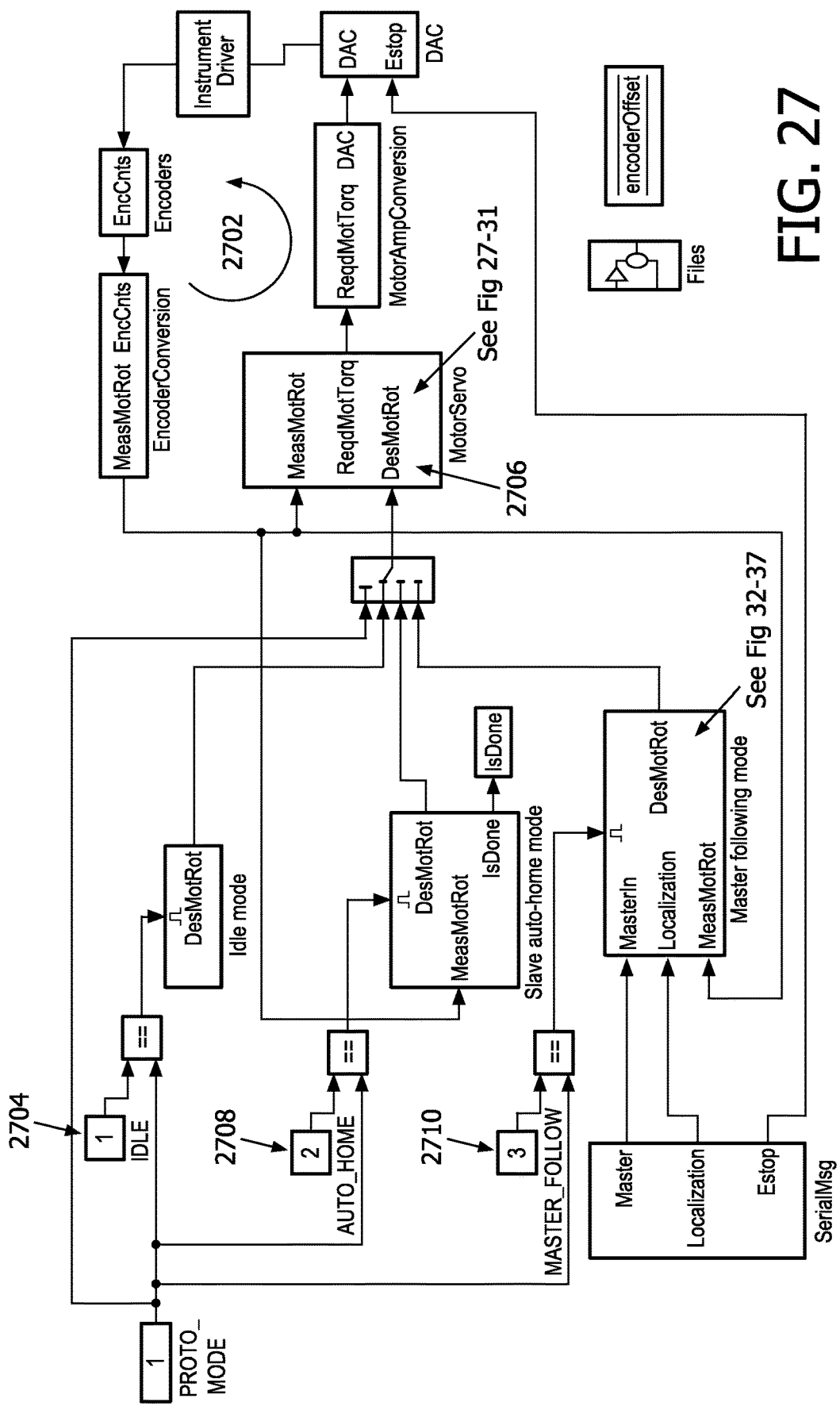

FIG. 27 depicts a high-level view of an embodiment wherein any one of three lodes may be toggled to operate the primary servo loop 2702. In idle mode 2704, the default mode When the system is started up, all of the motors are commanded via the motor servo block 2706 to servo about their current positions, their positions being monitored with digital encoders associated with the motors. In other words, idle mode 2704 deactivates the motors, while the remaining system stays active. Thus, when the operator leaves idle mode, the system knows the position of the relative components. In auto home mode 2708, cable loops within an associated instrument driver, such as the instrument driver 2220, are centered within their cable loop range to ensure substantially equivalent range of motion of an associated instrument, such as a catheter, in both directions for a various degree of freedom, such as + and − directions of pitch or yaw, when loaded upon the instrument driver. This is a setup mode for preparing an instrument driver before an instrument is engaged.

In master following mode 2710, the control system receives signals from the master input device, and in a closed loop embodiment from both a master input device and a localization system, and forwards drive signals to the primary servo loop 2702 to actuate the instrument in accordance with the forwarded commands. Aspects of this embodiment of the master following mode 2710 are depicted in further detail in FIGS. 32-37. Aspects of the primary servo loop and motor servo block 2706 are depicted in further detail in FIGS. 28-31.

Figure 33:
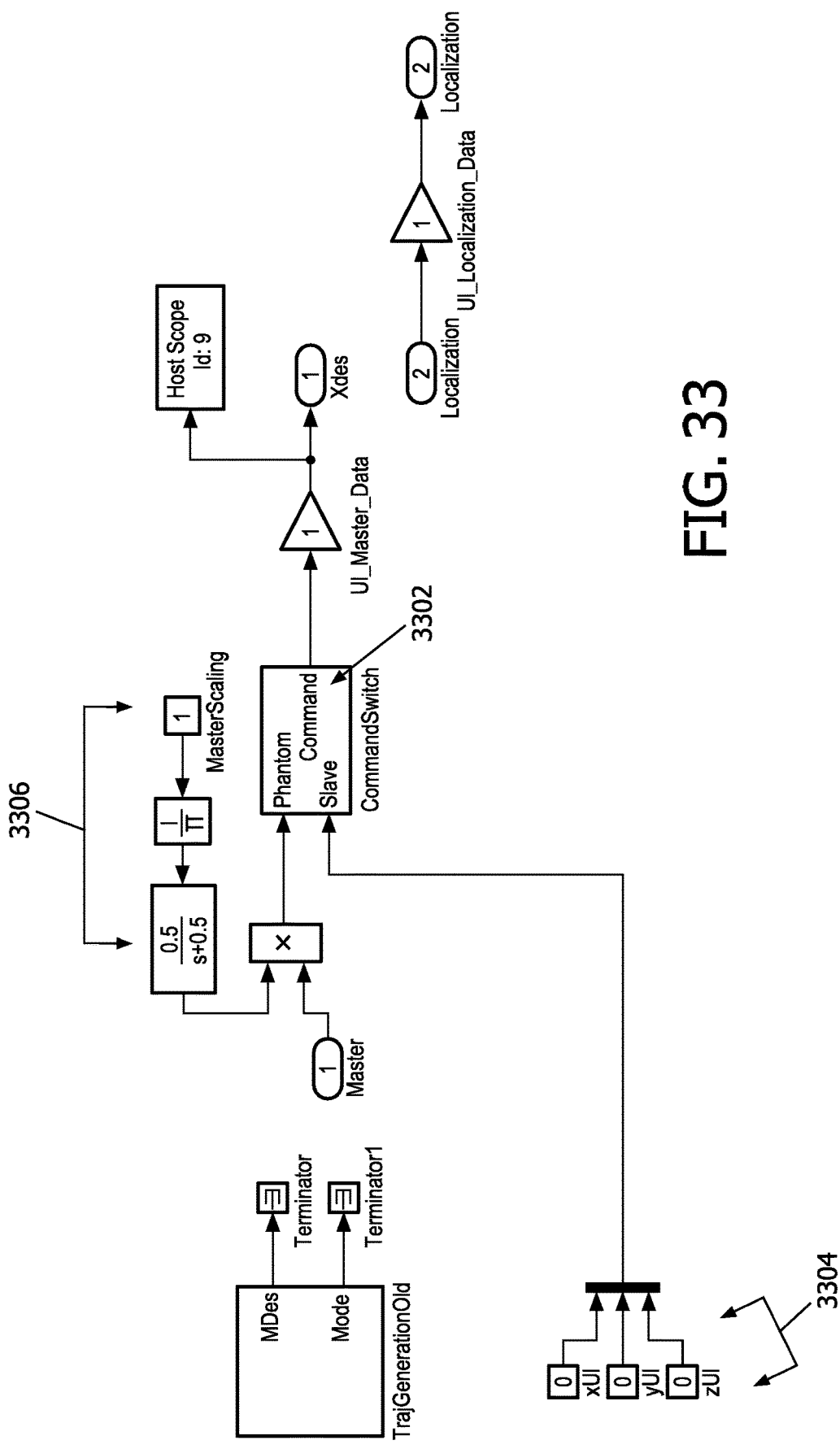

Referring to FIG. 32, a more detailed functional diagram of an embodiment of master following mode 2710 is depicted. As shown in FIG. 32, the inputs to functional block 3202 are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 33, for a more detailed view of functional block. 3202 of FIG. 32, a switch 3302 is provided at block to allow switching between master inputs for desired catheter position, to an input interface 3304 through which an operator may command that the instrument go to a particular XYZ location in space. Various controls features may also utilize this interface to provide an operator with, for example, a menu of destinations to which the system should automatically drive an instrument, etc. Also depicted in FIG. 33 is a master scaling functional block 3306 which is utilized to scale the inputs coming from the master input device with a ratio selectable by the operator. The command switch 3302 functionality includes a low pass filter to weight commands switching between the master input device and the input interface 3304, to ensure a smooth transition between these modes.

Referring back to FIG. 32, desired position data in XYZ terms is passed to the inverse kinematics block 3206 for conversion to pitch, yaw, and extension (or "insertion") terms in accordance with the predicted mechanics of materials relationships inherent in the mechanical design of the instrument.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship t, between actuated inputs and the catheter's end point position as a function of the actuated inputs is referred to as the "kinematics" of the catheter.

Figure 39:
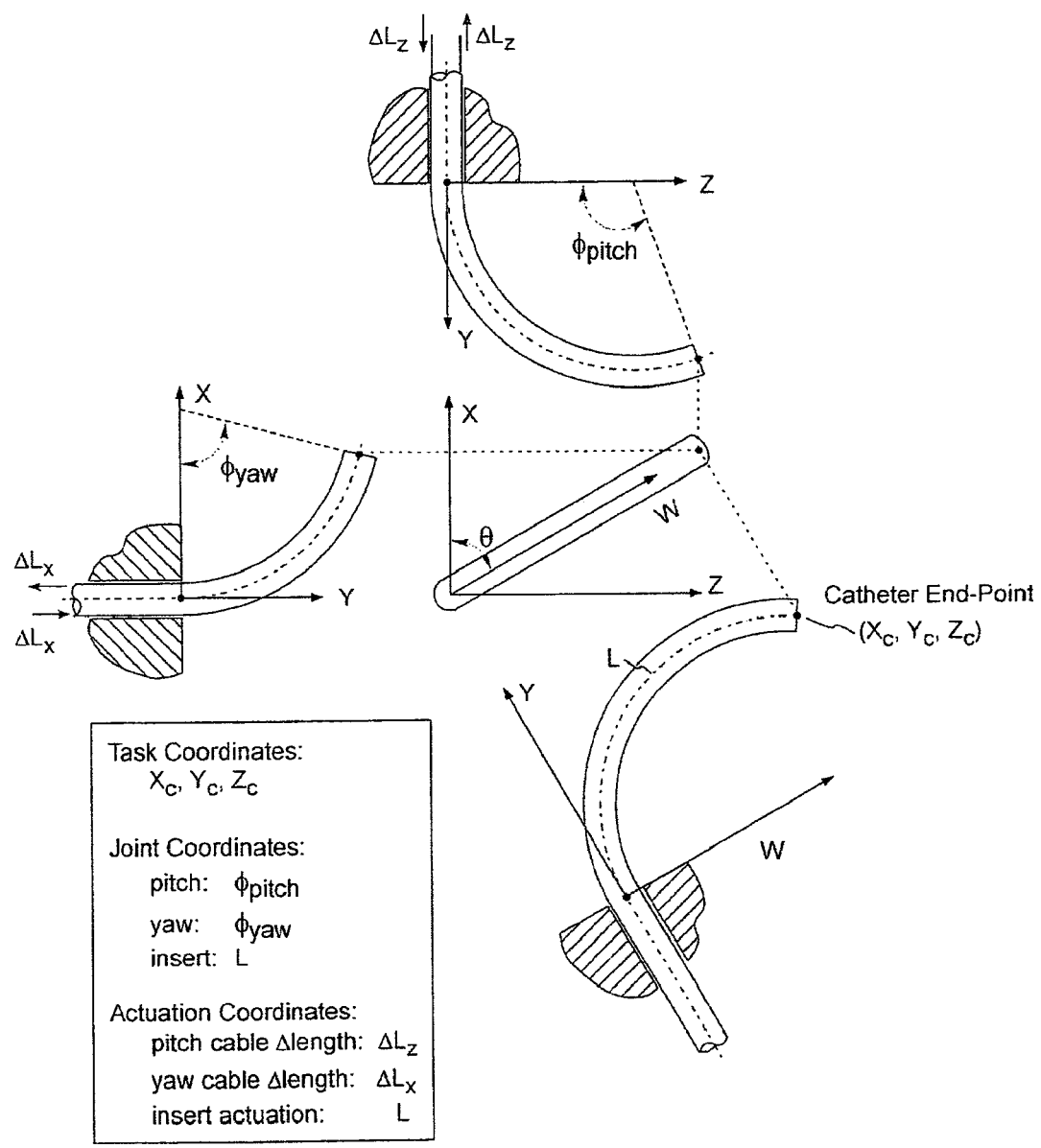

Referring to FIG. 38, the "forward kinematics" expresses the catheter's end-point position as a function of the actuated inputs while the "inverse kinematics" expresses the actuated inputs as a function of the desired end-point position. Accurate mathematical models of the forward and inverse kinematics are essential for the control of a robotically controlled catheter system. For clarity, the kinematics equations are further refined to separate out common elements, as shown in FIG. 38. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 39. By describing the kinematics in this way we can separate out the kinematics associated with the catheter structure, namely the basic kinematics, from those associated with the actuation methodology.

The development of the catheter's kinematics model is derived using a few essential assumptions. Included are assumptions that the catheter structure is approximated as a simple beam in bending from a mechanics perspective, and that control elements, such as thin tension wires, remain at a fixed distance from the neutral axis and thus impart a uniform moment along the length of the catheter.

Figure 40:
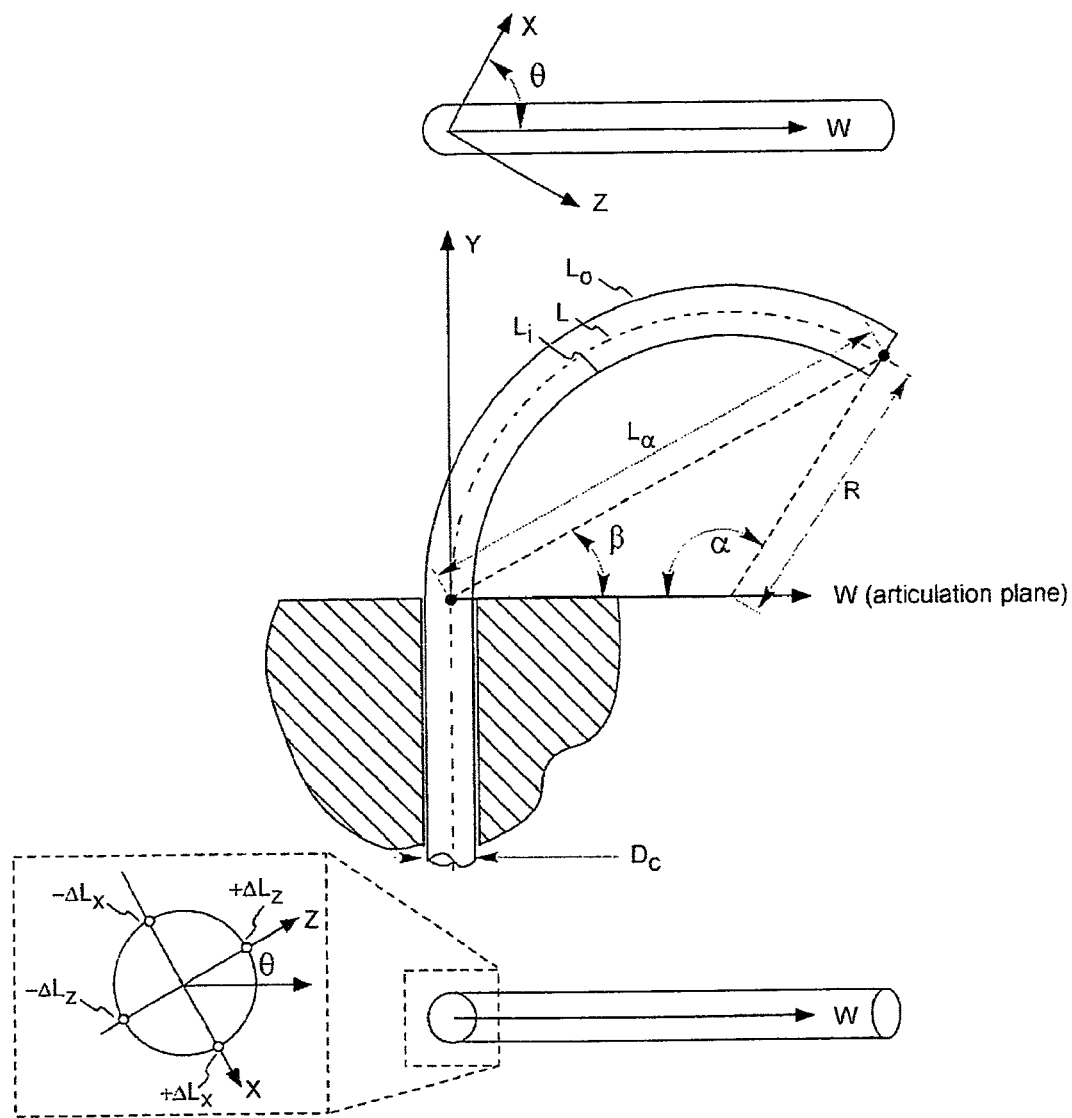
Figure 41:
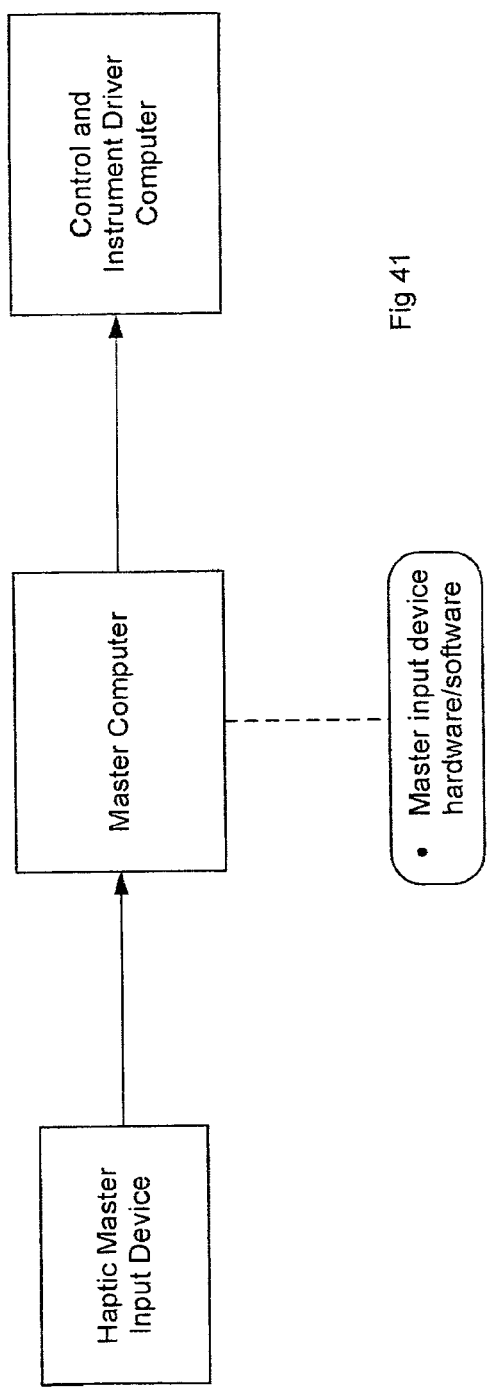

In addition to the above assumptions, the geometry and variables shown in FIG. 40 are used in the derivation of the forward and inverse kinematics. The basic forward kinematics relates catheter task coordinates to joint coordinates, as expressed in further detail in U.S. application Ser. No. 11/637,951. The actuator forward kinematics, relating the joint coordinates to the actuator coordinates are also expressed in application Ser. No. 11/637,951

As illustrated in FIG. 38, the catheter's end-point position can be predicted given the joint or actuation coordinates by using the forward kinematics equations described above. Calculation of the catheter's actuated inputs as a function of end-point position, referred to as the inverse kinematics, can be performed numerically, using a nonlinear equation solver such as Newton-Raphson. A more desirable approach, and the one used in this illustrative embodiment, is to develop a closed-form solution which can be used to calculate the required actuated inputs directly from the desired end-point positions.

As with the forward kinematics, we separate the inverse kinematics into the basic inverse kinematics, which relates joint coordinates to the task coordinates, and the actuation inverse kinematics, which relates the actuation coordinates to the joint coordinates. The basic inverse kinematics, relating the joint coordinates to the catheter task coordinates is expressed in application Ser. No. 11/637,951. The actuator inverse kinematics, relating the actuator coordinates to the joint coordinates is also expressed in application Ser. No. 11/637,951.

Figure 37:
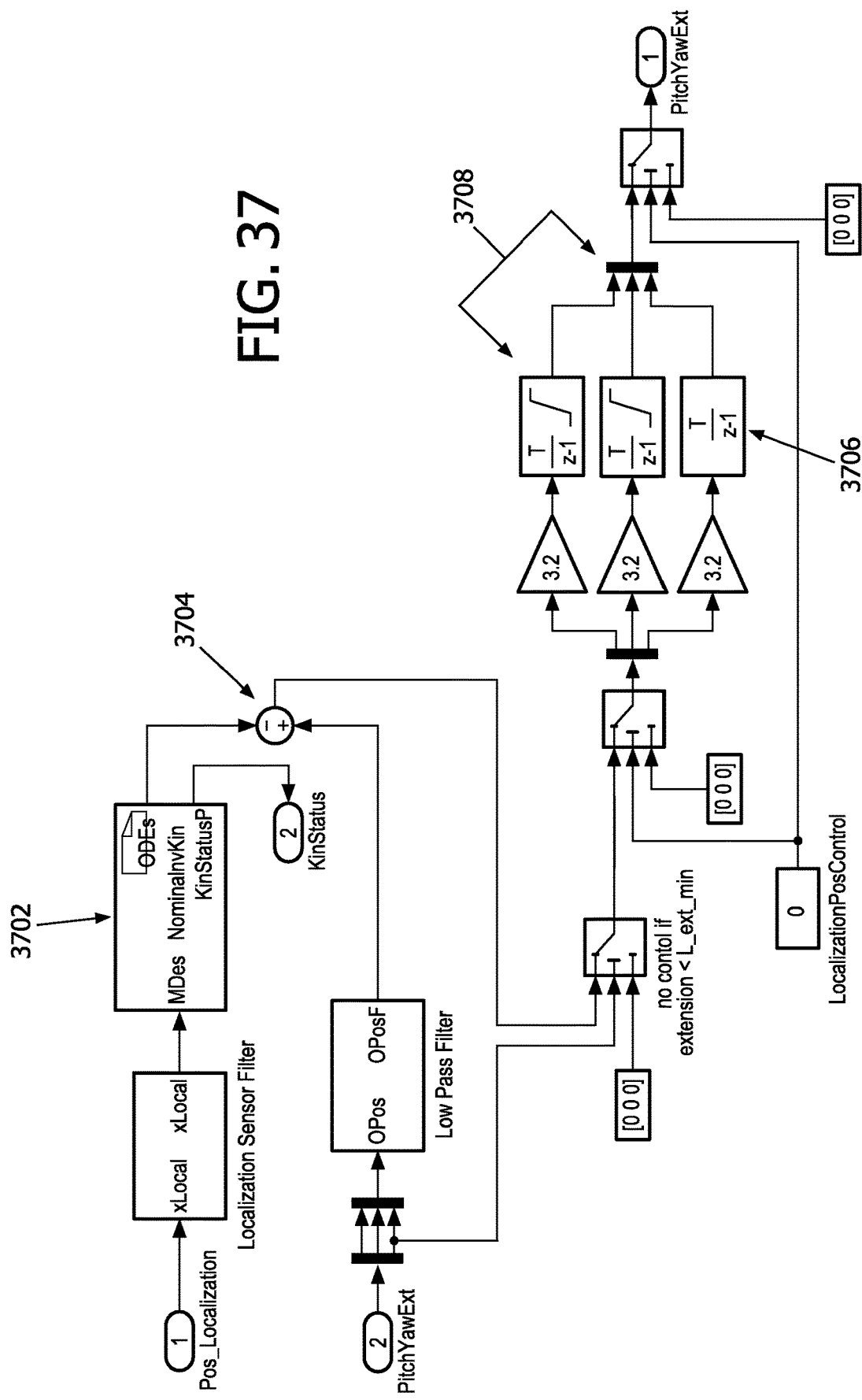

Referring back to FIG. 32, pitch, yaw, and extension commands are passed from the inverse kinematics block 3206 to a position control block 3204 along with measured localization data. FIG. 37 provides a more detailed view of the position control block 3204. After measured XYZ position data comes in from the localization system, it goes through an inverse kinematics block 3702 to calculate the pitch, yaw, and extension the instrument needs to have in order to travel to where it needs to be. Comparing 3704 these values with filtered desired pitch, yaw, and extension data from the master input device, integral compensation is then conducted with limits on pitch and yaw to integrate away the error. In this embodiment, the extension variable does not have the same limits 3706, as do pitch and yaw 3708. As will be apparent to those skilled in the art, having an integrator in a negative feedback loop forces the error to zero. Desired pitch, yaw, and extension commands are next passed through a catheter workspace limitation block 3208, which may be a function of the experimentally determined physical limits of the instrument beyond which componentry may fail, deform undesirably, or perform unpredictably or undesirably. This workspace limitation essentially defines a volume similar to a cardioid-shaped volume about the distal end of the instrument. Desired pitch, yaw, and extension commands, limited by the workspace limitation block, are then passed to a catheter roll correction block 3210.

Figure 34:
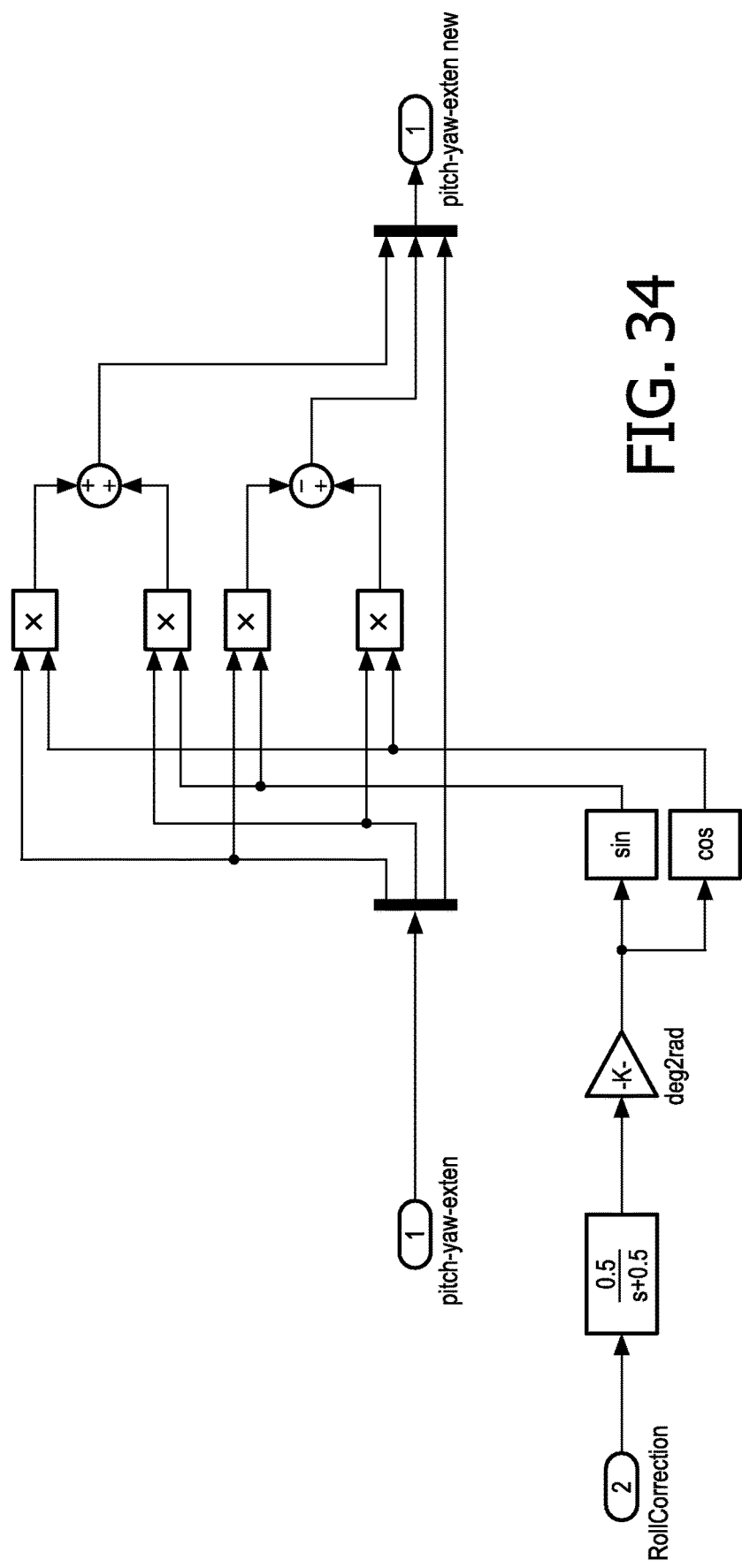

This functional block is depicted in further detail in FIG. 34, and essentially comprises a rotation matrix for transforming the pitch, yaw, and extension commands about the longitudinal, or "roll", axis of the instrument—to calibrate the control system for rotational deflection at the distal tip of the catheter that may change the control element steering dynamics For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 34 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the defection actually went—to simply determine the in-situ roll correction angle.

Figure 35:
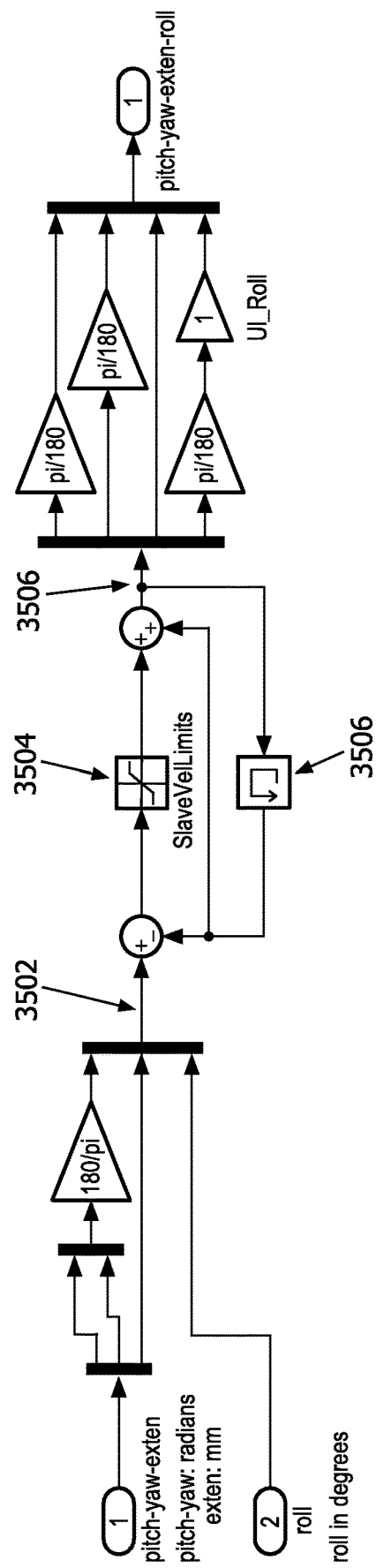

Referring briefly back to FIG. 32, roll corrected pitch and yaw commands, as well as unaffected extension commands, are output from the catheter roll correction block 3210 and may optionally be passed to a conventional velocity limitation block 3212. Referring to FIG. 35, pitch and yaw commands are converted from radians to degrees, and automatically controlled roll may enter the controls picture to complete the current desired position 3502 from the last servo cycle. Velocity is calculated by comparing the desired position from the previous servo cycle, as calculated with a conventional memory block calculation 3506, with that of the incoming commanded cycle. A conventional saturation block 3504 keeps the calculated velocity within specified values, and the velocity-limited command 3506 is converted back to radians and passed to a tension control block 3514.

Figure 36:
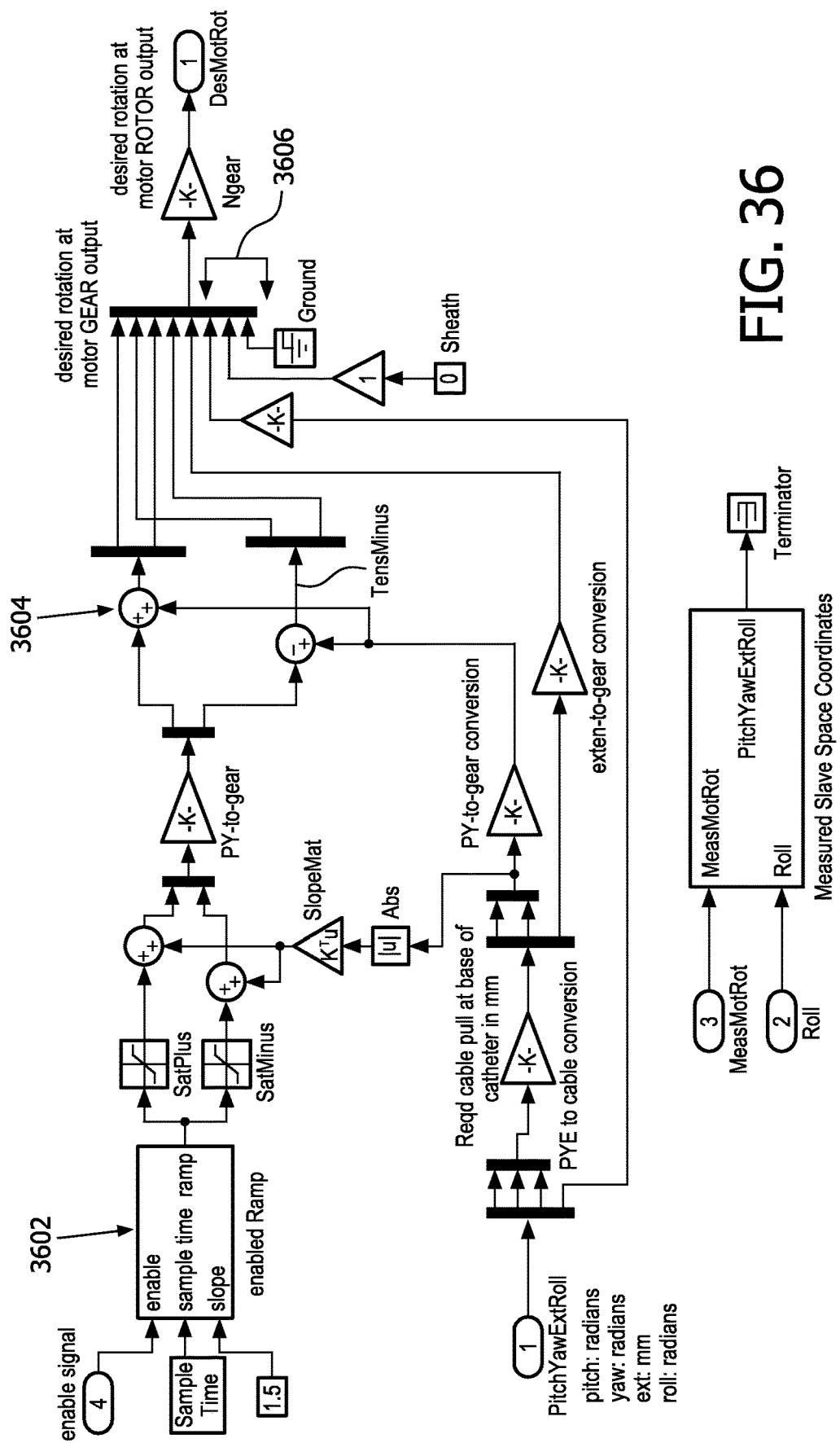

Tension within control elements may be managed depending upon the particular instrument embodiment, as described above in reference to the various instrument embodiments and tension control mechanisms. As an example, FIG. 36 depicts a pre-tensioning block 3602 with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added 3604 to the original signal for output, via gear ratio adjustment, to calculate desired motor rotation commands for the various motors involved with the instrument movement. In this embodiment, extension, roll, and sheath instrument actuation 3606 have no pre-tensioning algorithms associated with their control. The output is then complete from the master following mode functionality, and this output is passed to the primary servo loop 2702.

Referring back to FIG. 27, incoming desired motor rotation commands from either the master following mode 2710, auto home mode 2708, or idle mode 2704 in the depicted embodiment are fed into a motor servo block 2706, which is depicted in greater detail in FIGS. 28-31.

Figure 28:
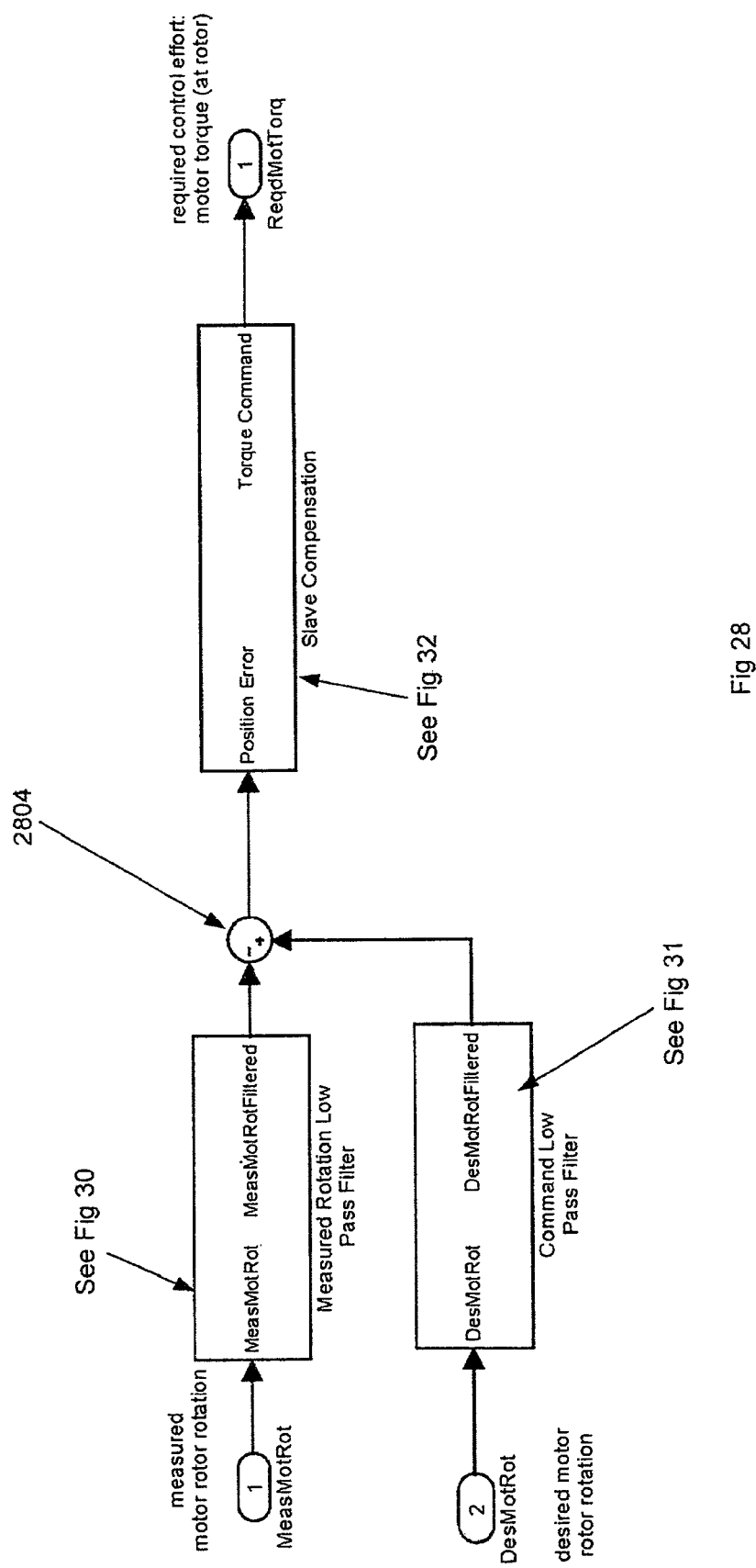
Figure 30:
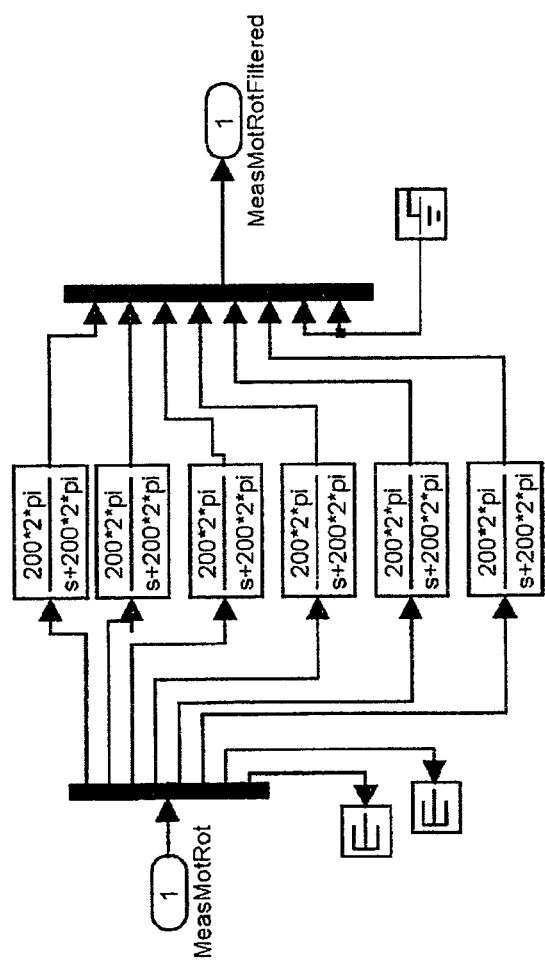
Figure 31:
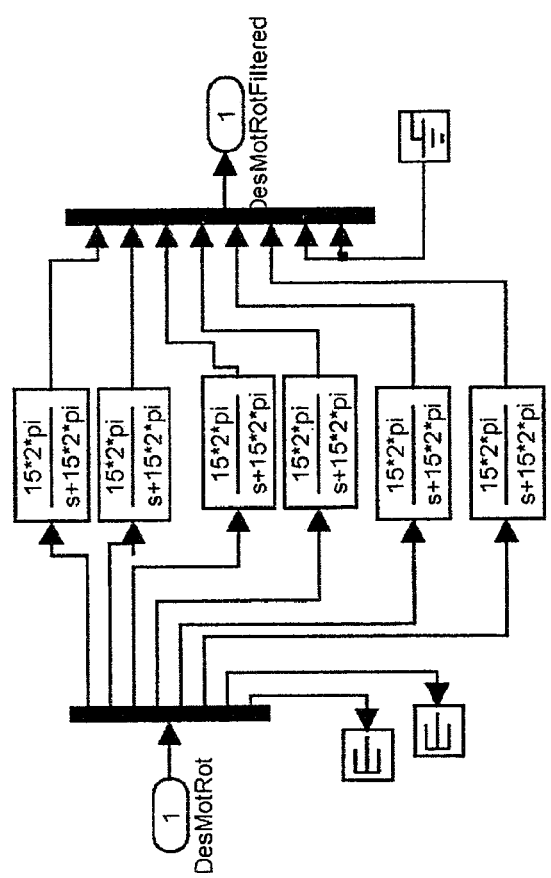

Referring to FIG. 28, incoming measured motor rotation data from digital encoders and incoming desired motor rotation commands are filtered using conventional quantization noise filtration at frequencies selected for each of the incoming data streams to reduce noise While not adding undue delays which may affect the stability of the control system. As shown in FIGS. 30-31, conventional quantization filtration is utilized on the measured motor rotation signals at about 200 hertz in this embodiment, and on the desired motor rotation command at about 15 hertz. The difference 2804 between the quantization filtered values forms the position error which may be passed through a lead filter, the functional equivalent of a proportional derivative ("PD")+ low pass filter. In another embodiment, conventional PID, lead/lag, or state space representation filter may be utilized. The lead filter of the depicted embodiment is shown in further detail in FIG. 29.

Figure 29:
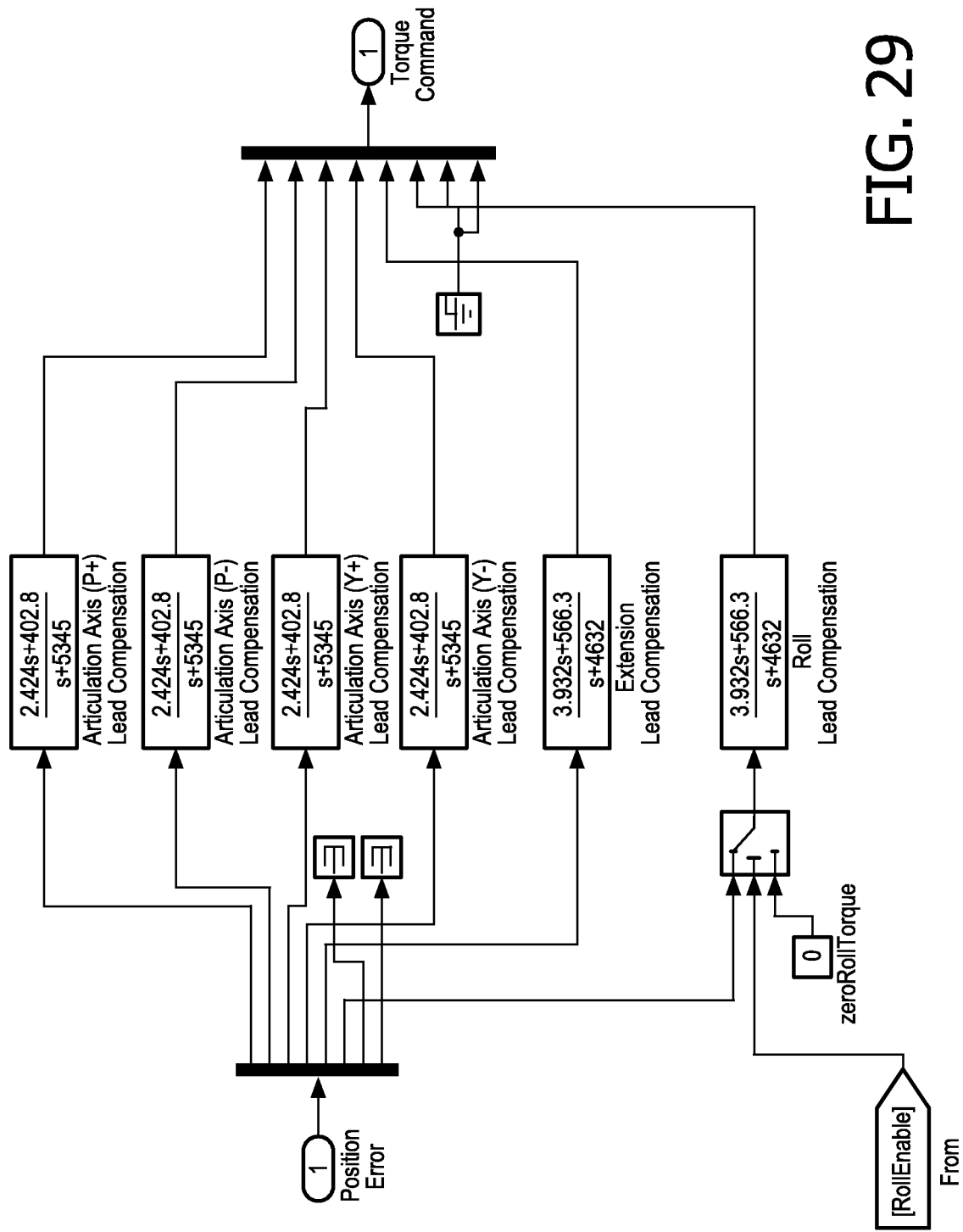

In particular, the lead filter embodiment in FIG. 29 comprises a variety of constants selected to tune the system to achieve desired performance. The depicted filter addresses the needs of one embodiment of a 4-control element guide catheter instrument with independent control of each of four control element interface assemblies for +/−pitch and +/−yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

Referring to FIG. 39, in one embodiment, the master input device may be a haptic master input device, such as those available from SensAble Technologies, Inc., under the trade name Phantoms® Haptic Devices, and the hardware and software required for operating such a device may at least partially reside on the master computer. The master XYZ positions measured from the master joint rotations and forward kinematics are generally passed to the master computer via a parallel port or similar link and may subsequently be passed to a control and instrument driver computer. With such an embodiment, an internal servo loop for a Phantoms® Haptic Device generally runs at a much higher frequency in the range of 1,000 Hz, or greater, to accurately create forces and torques at the joints of the master.

Figure 42:
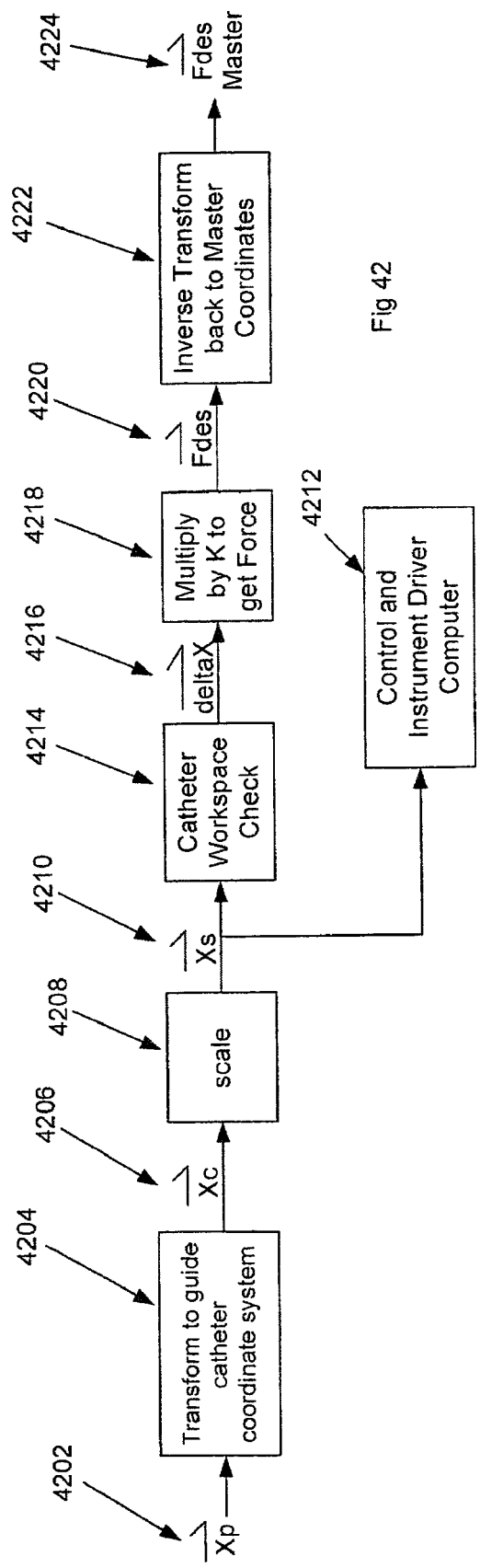

Referring to FIG. 42, a sample flowchart of a series of operations leading from a position vector applied at the master input device to a haptic signal applied back at the operator is depicted. A vector 4202 associated with a master input device move by an operator may be transformed into an instrument coordinate system, and in particular to a catheter instrument tip coordinate system, using a simple matrix transformation 4204. The transformed vector 4206 may then be scaled 4208 per the preferences of the operator, to produce a scaled-transformed vector 4210. The scaled-transformed vector may be sent to both the control and instrument driver computer 4212 preferably via a serial wired connection, and to the master computer for a catheter workspace check 4214 and any associated vector modification 4216. This is followed by a feedback constant multiplication 4218 chosen to produce preferred levels of feedback, such as force, in order to produce a desired force vector 4220, and an inverse transform 4222 back to a force vector 4224 in the master input device coordinate system for associated haptic signaling to the operator in that coordinate system.

A conventional Jacobian may be utilized to convert a desired force vector 4220 to torques desirably applied at the various motors comprising the master input device, to give the operator a desired signal pattern at the master input device. Given this embodiment of a suitable signal and execution pathway, feedback to the operator in the form of haptics, or touch sensations, may be utilized in various ways to provide added safety and instinctiveness to the navigation features of the system, as discussed in further detail below.

Figure 43:
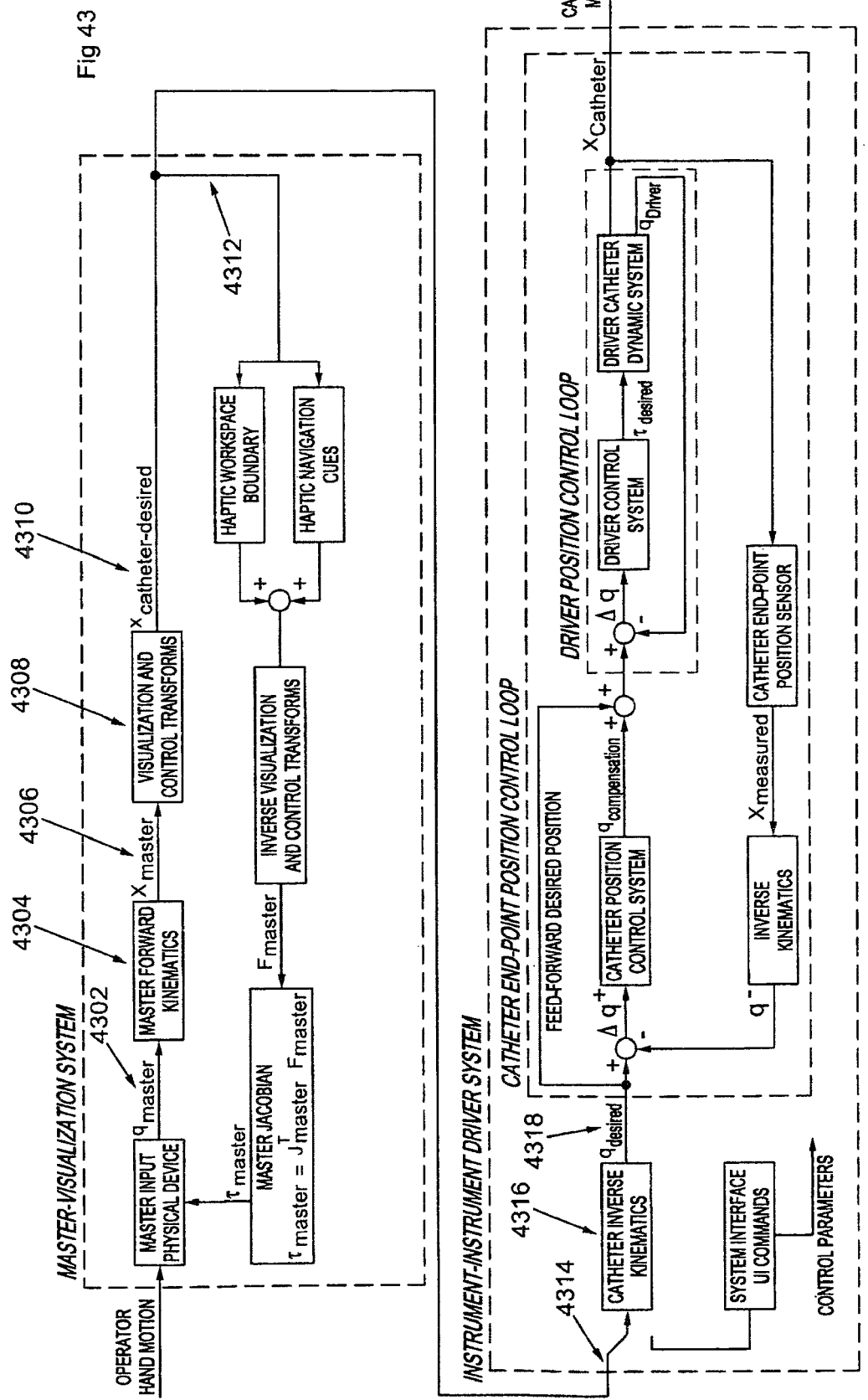

FIG. 43 is a system block diagram including haptics capability. As shown in summary form in FIG. 43, encoder positions on the master input device, changing in response to motion at the master input device, are measured 4302, sent through forward kinematics calculations 4304 pertinent to the master input device to get XYZ spatial positions of the device in the master input device coordinate system 4306, then transformed 4308 to switch into the catheter coordinate system and (perhaps) transform for visualization orientation and preferred controls orientation, to facilitate "instinctive driving".

The transformed desired instrument position 4310 may then be sent down one or more controls pathways to, for example, provide haptic feedback 4312 regarding workspace boundaries or navigation issues, and provide a catheter instrument position control loop 4314 with requisite catheter desired position values, as transformed utilizing catheter inverse 4316 kinematics relationships for the particular instrument into yaw, pitch, and extension, or insertion, terms 4318 pertinent to operating the particular catheter instrument with open or closed loop control.

Figure 44:
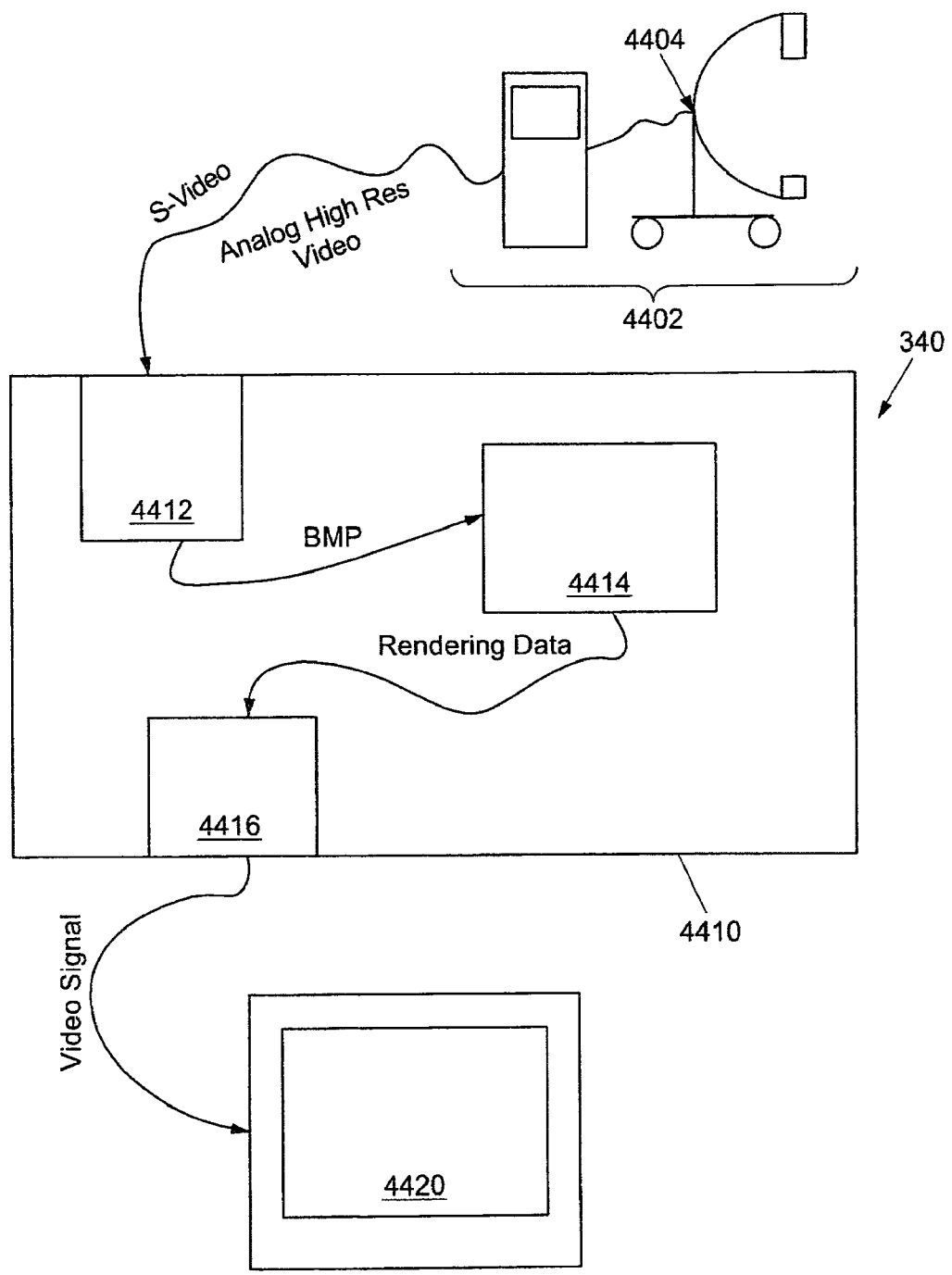
FIGS. 44-49 illustrate a system and system configuration for visualization of tissue by overlaying images, a schematic for overlaying objects to the display, a distributed system architecture and hardware and software interfaces of robotic surgical systems in which embodiments may be implemented.

As further reference, referring to FIG. 44, a systemic view configured to produce an overlaid image is depicted. A known fluoroscopy system 4402 outputs an electronic image in formats such as those known as "S-video" or "analog high-resolution video". In image output interface 4404 of a fluoroscopy system 4402 may be connected to an input interface of a computer 4410 based image acquisition device, such as those known as "frame grabber" 4412 image acquisition cards, to facilitate intake of the video signal from the fluoroscopy system 4402 into the frame grabber 4412, which may be configured to produce bitmap ("BMP") digital image data, generally comprising a series of Cartesian pixel coordinates and associated grayscale or color values which together may be depicted as an image. The bitmap data may then be processed utilizing computer graphics rendering algorithms, such as those available in conventional OpenGL graphics libraries 4414. In summary, conventional OpenGL functionality enables a programmer or operator to define object positions, textures, sizes, lights, and cameras to produce three-dimensional renderings on a two-dimensional display. The process of building a scene, describing objects, lights, and camera position, and using OpenGL functionality to turn such a configuration into a two-dimensional image for display is known in computer graphics as rendering. The description of objects may be handled by forming a mesh of triangles, which conventional graphics cards are configured to interpret and output displayable two-dimensional images for a conventional display or computer monitor, as would be apparent to one skilled in the art. Thus the OpenGL software 4414 may be configured to send rendering data to the graphics card 4416, which may then be output to a conventional display 4420.

A triangular mesh generated with OpenGL software may be used to form a cartoon-like rendering of an elongate instrument moving in space according to movements from, for example, a master following mode operational state, may be directed to a computer graphics card, along with frame grabber and OpenGL processed fluoroscopic video data. Thus a moving cartoon-like image of an elongate instrument would be displayable. To project updated fluoroscopic image data onto a flat-appearing surface in the same display, a plane object, conventionally rendered by defining two triangles, may be created, and the updated fluoroscopic image data may be texture mapped onto the plane. Thus the cartoon-like image of the elongate instrument may be overlaid with the plane object upon which the updated fluoroscopic image data is texture mapped. Camera and light source positioning may be pre-selected, or selectable by the operator through the mouse or other input device, for example, to enable the operator to select desired image perspectives for his two-dimensional computer display. The perspectives, which may be defined as origin position and vector position of the camera, may be selected to match with standard views coming from a fluoroscopy system, such as anterior/posterior and lateral views of a patient lying on an operating table. When the elongate instrument is visible in the fluoroscopy images, the fluoroscopy plane object and cartoon instrument object may be registered with each other by ensuring that the instrument depicted in the fluoroscopy plane lines up with the cartoon version of the instrument. In one embodiment, several perspectives are viewed while the cartoon object is moved using an input device such as a mouse, until the cartoon instrument object is registered with the fluoroscopic plane image of the instrument. Because both the position of the cartoon object and fluoroscopic image object may be updated in real time, an operator, or the system automatically through image processing of the overlaid image, may interpret significant depicted mismatch between the position of the instrument cartoon and the instrument fluoroscopic image as contact with a structure that is inhibiting the normal predicted motion of the instrument, error or malfunction in the instrument, or error or malfunction in the predictive controls software underlying the depicted position of the instrument cartoon.

Referring back to FIG. 44, other video signals (not shown) may be directed to the image grabber 4412, besides that of a fluoroscopy system 4402, simultaneously. For example, images from an intracardiac echo ultrasound ("ICE") system, intravascular ultrasound ("IVUS"), or other system may be overlaid onto the same displayed image simultaneously. Further, additional objects besides a plane for texture mapping fluoroscopy or an elongate instrument cartoon object may be processed using OpenGL or other rendering software to add additional objects to the final display.

Figure 45A:
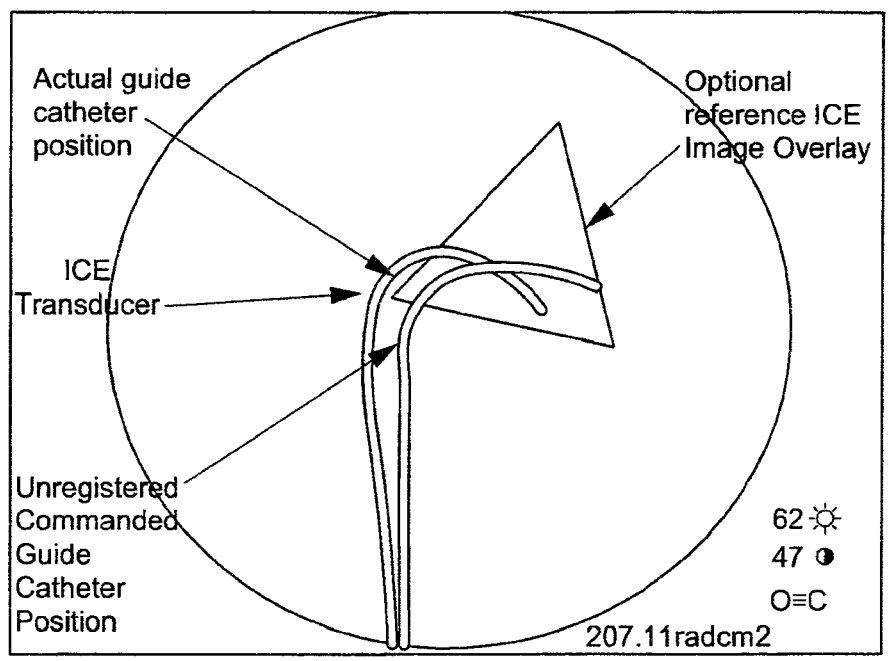
Figure 45B:
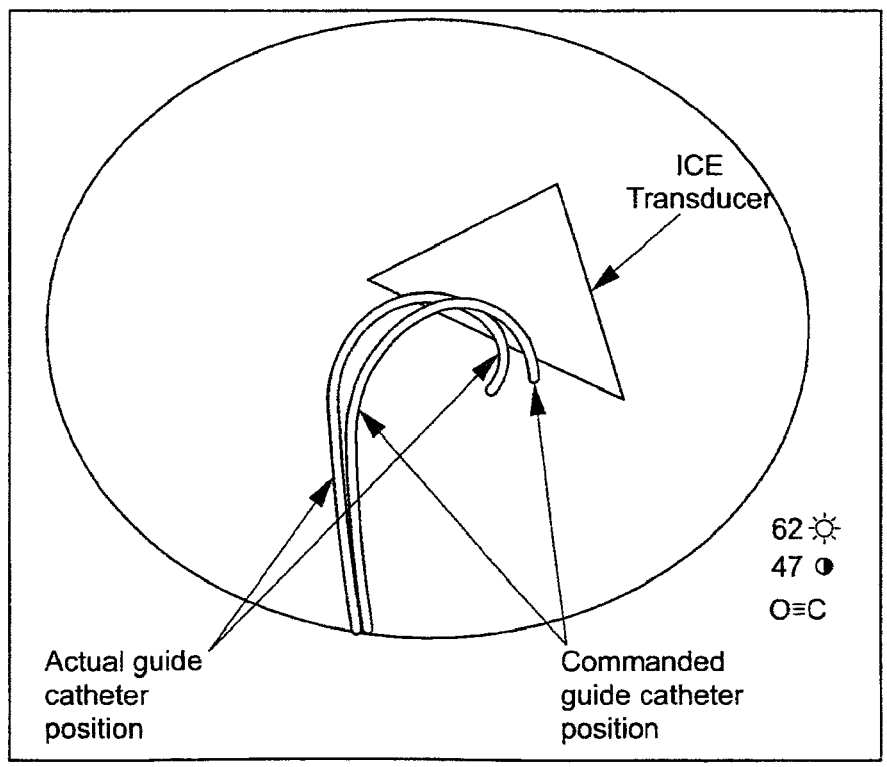
Figure 46:
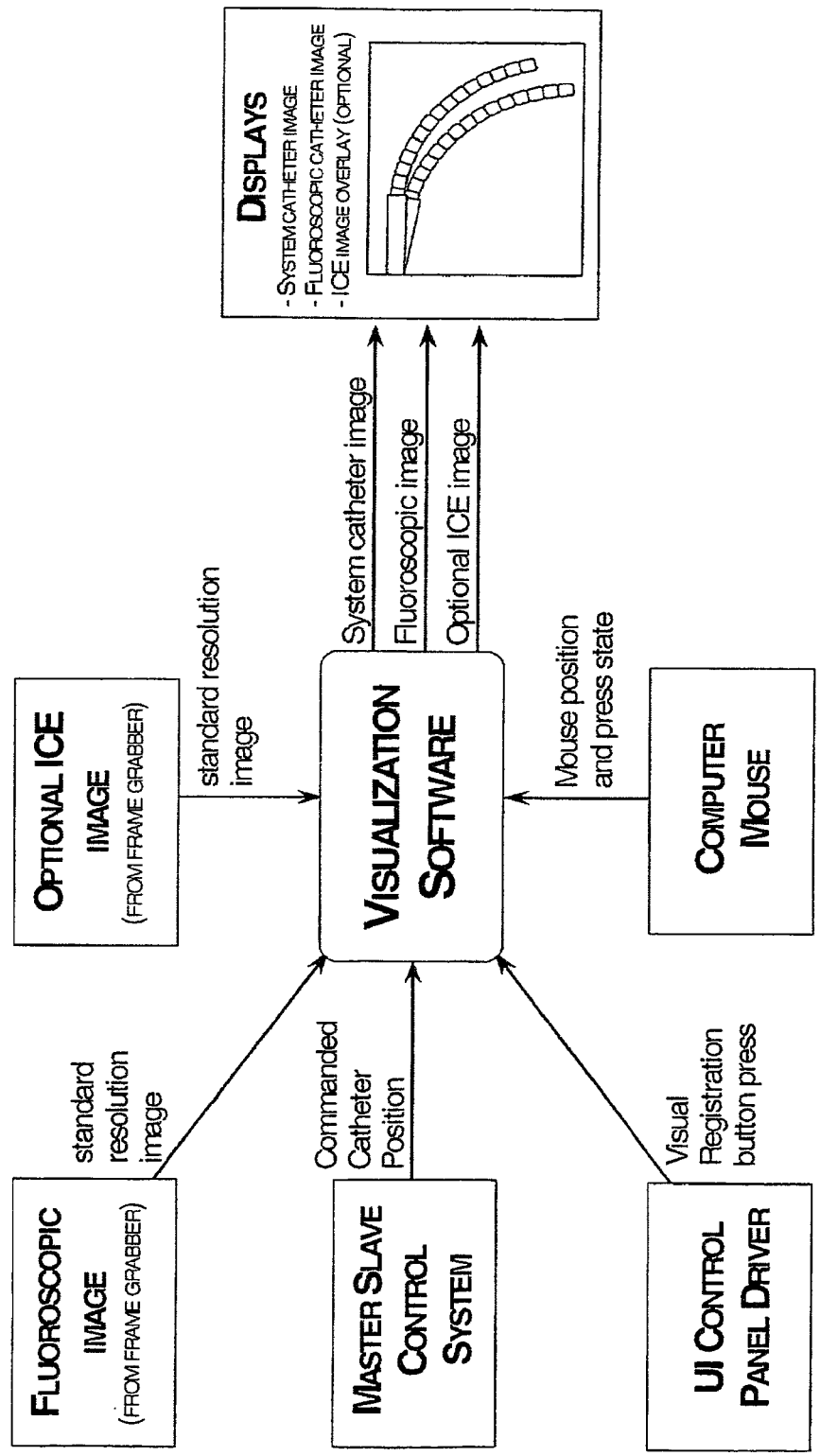

Referring to FIGS. 45A-B and 46, an elongate instrument is a robotic guide catheter, and fluoroscopy and ICE are utilized to visualize the cardiac and other surrounding tissues, and instrument objects. Referring to FIG. 45A, a fluoroscopy image has been texture mapped upon a plane configured to occupy nearly the entire display area in the background. Visible in the fluoroscopy image as a dark elongate shadow is the actual position, from fluoroscopy, of the guide catheter instrument relative to the surrounding tissues. Overlaid in front of the fluoroscopy plane is a cartoon rendering (white in color in FIGS. 45A-B) of the predicted, or "commanded", guide catheter instrument position. Further overlaid in from of the fluoroscopy plane is a small cartoon object representing the position of the ICE transducer, as well as another plane object adjacent the ICE transducer cartoon object onto which the ICE image data is texture mapped by a technique similar to that with which the fluoroscopic images are texture mapped upon the background plane object. Further, mouse objects, software menu objects, and many other objects may be overlaid. FIG. 45A shows a similar view with the instrument in a different position. For illustrative purposes, FIGS. 45A-B depict misalignment of the instrument position from the fluoroscopy object, as compared with the instrument position from the cartoon object. As described above, the various objects may be registered to each other by manually aligning cartoon objects with captured image objects in multiple views until the various objects are aligned as desired. Image processing of markers and shapes of various objects may be utilized to automate portions of such a registration process.

Referring to FIG. 46, a schematic is depicted to illustrate how various objects, originating from actual medical images processed by frame grabber, originating from commanded instrument position control outputs, or originating from computer operating system visual objects, such as mouse, menu, or control panel objects, may be overlaid into the same display.

Further, a pre-acquired image of pertinent tissue, such as a three-dimensional image of a heart, may be overlaid and registered to updated images from real-time medical imaging modalities as well. For example, in one embodiment, a beating heart may be preoperatively imaged using gated computed tomography (CT). The result of CT imaging may be a stack of CT data slices. Utilizing either manual or automated thresholding techniques, along with interpolation, smoothing, and/or other conventional image processing techniques available in software packages such as that sold under the tradename Amira® product available from Mercury Computer Systems of Chelmsford, Mass., a triangular mesh may be constructed to represent a three-dimensional cartoon-like object of the heart, saved, for example, as an object (".obj") file, and added to the rendering as a heart object. The heart object may then be registered as discussed above to other depicted images, such as fluoroscopy images, utilizing known tissue landmarks in multiple views, and contrast agent techniques to particularly see show certain tissue landmarks, such as the outline of an aorta, ventricle, or left atrium. The cartoon heart object may be moved around, by mouse, for example, until it is appropriately registered in various views, such as anterior/posterior and lateral, with the other overlaid objects.

Figure 47:
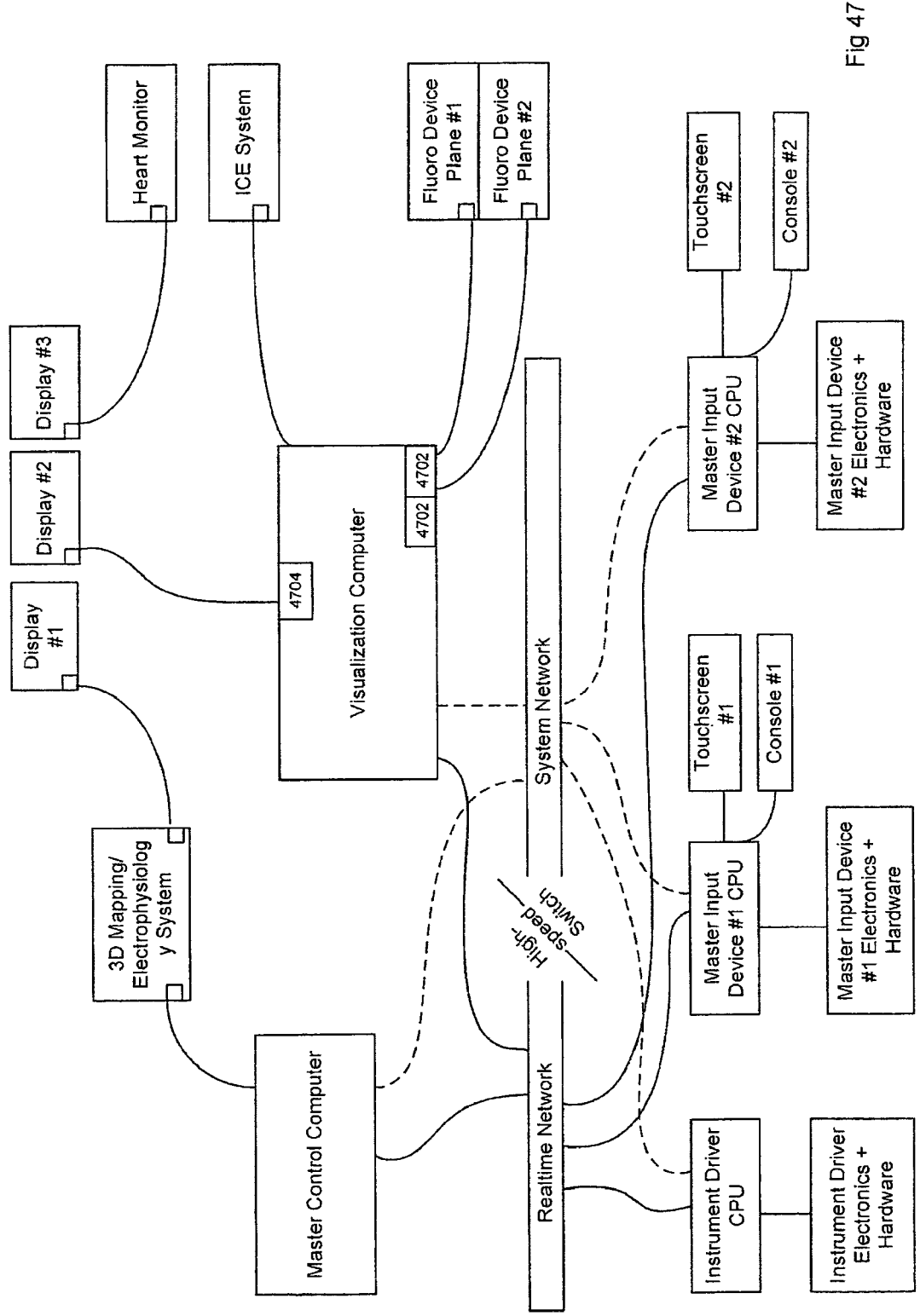

Referring to FIG. 47, a distributed system architecture embodiment is depicted. A master control computer running a real-time operating system, such as QNX, is connected to each of the other computers in the system by a 1 gigabit Ethernet "Real-time Network", and also by a 100 megabit Ethernet "System Network", using a conventional high-speed switch. This enables localized custom computing for various devices to be pushed locally near the device, without the need for large cabling or a central computing machine. In one embodiment, the master control computer may be powered by an Intel® Xeon® processor available from Intel Corporation of Santa Clara, Calif., the visualization computer powered by a personal computer (PC) with a high-end microprocessor based on the Intel architecture running Windows XP and having multiple video cards and frame grabbers, the instrument driver and master input device CPUs being PC or "EPIC" standard boards with two Ethernet connections for the two networks. An additional master input device, touchscreen, and console may be configured into an addition operator workstation in a different location relative to the patient. The system is very expandable—new devices may be plugged into the switch and placed onto either of the two networks.

Referring to FIG. 47, two high resolution frame grabber boards 4702 acquire images from two fluoro devices (or one in the case of single plane fluoro), which a nominal resolution frame grabber board 4702 acquires images from an intracardiac echo system. Such image data may be utilized for overlaying, etc., as described in reference to FIGS. 44-46, and displayed on a display, such as the #2 display, using a video card 4704 of the visualization computer, as depicted. Heart monitor data, from a system such as the Prucka CardioLab EP System distributed by GE Healthcare of Waukesha, Wis., may be directly channeled from video out ports on the heart monitor device to one of the displays. Such data may also be acquired by a frame grabber. Similarly, electrophysiological mapping and treatment data and images from systems available from distributors such as Endocardial Solutions, Biosense Webster, Inc., etc., may be directed as video to a monitor, or data to a data acquisition board, data bus, or frame grabber. Preferably the master control computer has some interface connectivity with the electrophysiology system as well to enable single master input device driving of such device, etc.

Figure 48:
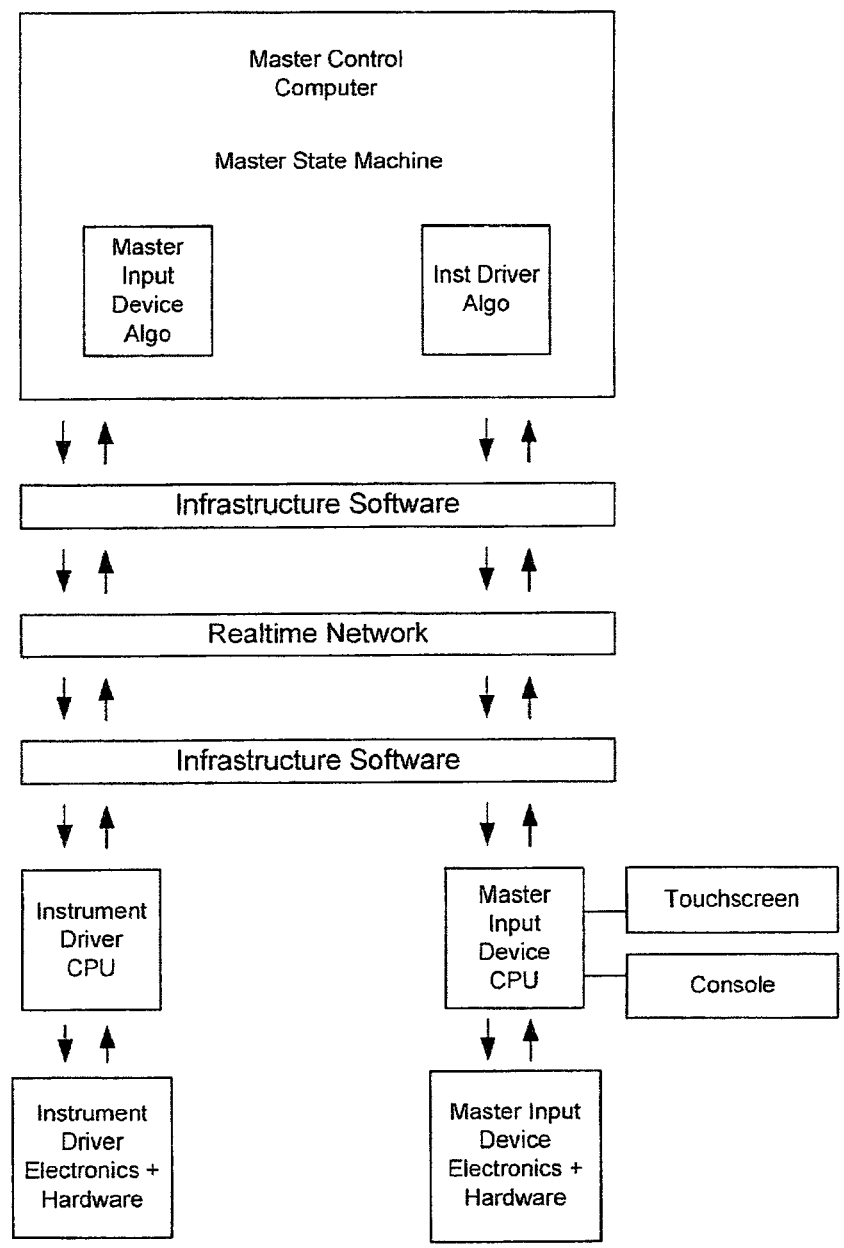
Figure 49:
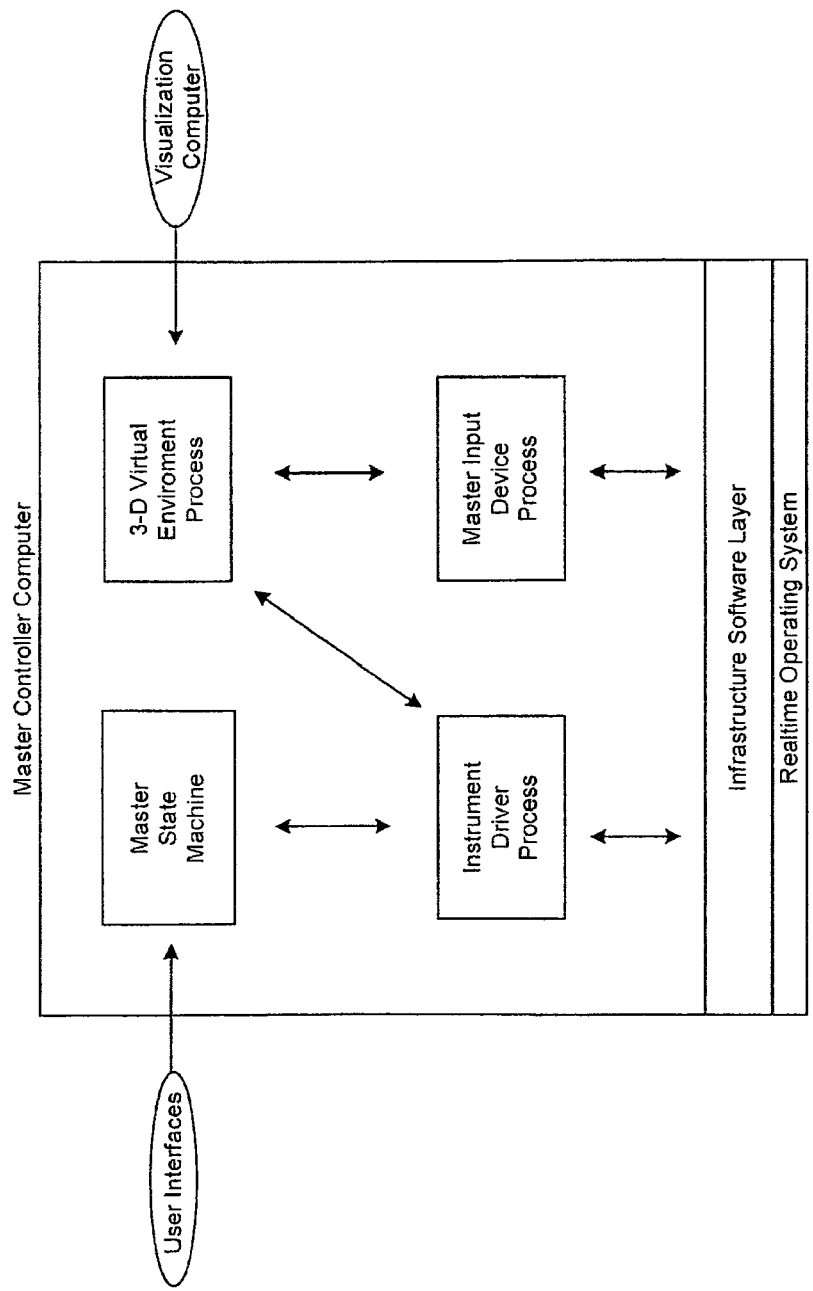

Referring to FIG. 48, a depiction of the software and hardware interaction is depicted. Essentially, the master state machine functionality of the master control system real-time operating system allows for very low latency control of processes used to operate master input device algorithms and instrument driver algorithms, such as those described in reference to the control systems description above. Indeed, XPC may be utilized to develop algorithm code, but preferably a universal modeling language such as IBM Rational Rose from IBM Corporation of Armonk, N.Y., or Rhapsody of I-Logix of Andover, Mass., is utilized to build code and documentation using a graphical interface. With the gigabit real-time network, in a matter of 200-300 microseconds, the master input device or instrument driver algorithms are able to communicate with FPGA driver code in the electronics and hardware near the pertinent device to exchange new values, etc., and confirm that all is well from a safety perspective. This leaves approximately 700 microseconds for processing if a 1 millisecond motor shutoff time is required if all is not well—and this is easily achievable with the described architecture. The visualization PC may be configured to cycle data from the master control computer at a lower frequency, about 20 milliseconds. FIG. 49 illustrates the software interaction of one embodiment.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Many combinations and permutations of the disclosed embodiments are useful in minimally invasive surgery, and the system is configured to be flexible for use with other system components and in other applications. Thus, various changes and modifications may be made without departing from the scope of the claims.

For example, although embodiment are described with reference to a telemanipulation system or robotic control system, embodiments may also be manually controlled by a surgeon, e.g., near the proximal section of the sheath catheter. Embodiments are advantageously suited for minimally invasive procedures, they may also be utilized in other, more invasive procedures that utilize extension tools and may be used in surgical procedures other than treatment of arrhythmias such as atrial fibrillation.

Further, although embodiments are described with reference to a fiber or fiber sensor coupled to or integral with a catheter, embodiments may also involve a fiber or fiber sensor coupled to or integral with a sheath, multiple catheters or other elongate instruments, e.g., that extend through a sheath, a working instrument, and other system components such as an a localization sensor, an instrument driver, a patient's bed, a patient, and combinations thereof. Further, such fibers may be positioned within an elongate instrument or coupled to or integral with an outer surface thereof.

Moreover, depending on the configuration of a system and system components, a "controller" may be or include a unit coupled to a fiber, may be, or include, a computer or processor of a robotic instrument system (e.g., in an electronics rack or at a user workstation), or a combination thereof. Further, a unit that sends and/or receives light may be a separate component or integrated within a controller component of a robotic instrument system. Thus, a "controller" may be a standalone or integrated component or include multiple components that are operably coupled together.

Further, it should be understood that embodiments of an optical fiber sensor and apparatus, system and methods including or involving the same may be used in various applications and be configured in various different ways. For example, they may be coupled to or integral with various system components intended for insertion, into a patent and that are intended for external use. Optical fiber sensors may also include various numbers of FBGs, which may be of the same or different wavelengths, and may be arranged in different ways. Further, various optical systems can be used with embodiments, and the exemplary components and read out system are provided as one example of how embodiments may be implemented.

Because one or more components of embodiments may be used in minimally invasive surgical procedures, the distal portions of these instruments may not be easily visible to the naked eye. As such, embodiments of the invention may be utilized with various imaging modalities such as magnetic resonance (MR), ultrasound, computer tomography (CT), X-ray, fluoroscopy, etc. may be used to visualize the surgical procedure and progress of these instruments. It may also be desirable to know the precise location of any given catheter instrument and/or tool device at any given moment to avoid undesirable contacts or movements. Thus, embodiments may be utilized with localization techniques that are presently available may be applied to any of the apparatuses and methods disclosed above. Further, a plurality of sensors, including those for sensing patient vitals, temperature, pressure, fluid flow, force, etc., may be combined with the various embodiments of flexible catheters and distal orientation platforms.

Various system components including catheter components may be made with materials and techniques similar to those described in detail in U.S. patent application Ser. No. 11/176,598, incorporated by reference herein in its entirety. Further, various materials may be used to fabricate and manufacture sheath catheter segment, rotatable apparatus and orientation platform devices. For example, it is contemplated that in addition to that disclosed above, materials including, but not limited to, stainless steel, copper, aluminum, nickel-titanium alloy (Nitinol), Flexinol® (available from Toki of Japan), titanium, platinum, iridium, tungsten, nickel-chromium, silver, gold, and combinations thereof, may be used to manufacture components such as control elements, control cables, segments, gears, plates, hall units, wires, springs, electrodes, thermocouples, etc. Similarly, non-metallic materials including, but not limited to, polypropylene, polyurethane (Pebax®), nylon, polyethylene, polycarbonate, Delrin®, polyester, Kevlar®, carbon, ceramic, silicone, Kapton® polyimide, Teflon® coating, polytetrafluoroethylene (PTFE), plastic (non-porous or porous), latex, polymer, etc. may be used to make the various parts of a catheter, orientation platform, tool, etc.

Additionally, certain system components are described as having lumens that are configured for carrying or passage of control elements, control cables, wires, and other catheter instruments. Such lumens may also be used to deliver fluids such as saline, water, carbon dioxide, nitrogen, helium, for example, in a gaseous or liquid state, to the distal tip. Further, some embodiments may be implemented with an open loop or closed loop cooling system wherein a fluid is passed through one or more lumens in the sidewall of the catheter instrument to cool the catheter or a tool at the distal tip.

Further, embodiments may be utilized with various working instruments including end effectors including, for example, a Kittner dissector, a multi-fire coil tacker, a clip applier, a cautery probe, a shovel cautery instrument, serrated graspers, tethered graspers, helical retraction probe, scalpel, basket capture device, irrigation tool, needle holders, fixation device, transducer, and various other graspers. A number of other catheter type instruments may also be utilized together with certain embodiments including, but not limited to, a mapping catheter, an ablation catheter, an ultrasound catheter, a laser fiber, an illumination fiber, a wire, transmission line, antenna, a dilator, an electrode, a microwave catheter, a cryo-ablation catheter, a balloon catheter, a stent delivery catheter, a fluid/drug delivery tube, a suction tube, an optical fiber, an image capture device, an endoscope, a Foley catheter, Swan-Ganz catheter, fiberscope, etc. Thus, it is contemplated that one or more catheter instruments may be inserted through one or more lumens of a flexible catheter instrument, flexible sheath instrument, or any catheter instrument to reach a surgical site at the distal tip. Similarly, it is contemplated that one or more catheter instruments may be passed through an orientation platform to a region of interest.

While multiple embodiments and variations of the many aspects of the present disclosure have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the present disclosure are susceptible to various modifications and alternative forms, and it should be understood that the present disclosure generally, as well as the specific embodiments described herein, are not limited to the particular forms or methods disclosed, but also cover all modifications, equivalents and alternatives. Further, the various features and aspects of the illustrated embodiments may be incorporated into other embodiments, even if no so described herein, as will be apparent to those skilled in the art.

What is claimed is:

1. An instrument system, comprising:
   an elongate sheath having a lumen;
   a plurality of working instruments positioned in the sheath lumen, each working instrument comprising an elongate instrument body positioned in the sheath lumen and having a distal end portion that extends out of a distal end opening of the sheath in communication with the lumen, each instrument body distal end portion being coupled to an optical fiber;
   a reference sensor positioned on the elongate sheath proximate to the distal end opening, the reference sensor positioned on the elongate sheath being independent from the optical fibers coupled to the respective instrument bodies; and
   a controller configured to determine one or more position and/or orientation variables of the distal end portions of the respective instrument bodies based upon signals received from their associated optical fibers,
   wherein the one or more position and/or orientation variables of the distal end portions of the respective instrument bodies are determined relative to the reference sensor positioned on the elongate sheath.

2. The system of claim 1, wherein the controller is further configured to generate and display a graphical representation of the respective instrument bodies relative to the distal end opening of the sheath.

3. The system of claim 1, wherein the reference sensor comprises an optical fiber having a fiber core with one or more Bragg gratings.

4. The system of claim 1, wherein the controller is configured to determine a position and/or orientation of the distal end of the sheath in a reference coordinate system based on signals received from the reference sensor.

* * * * *